United States Patent [19]
Guarente et al.

[11] Patent Number: 5,919,618
[45] Date of Patent: Jul. 6, 1999

[54] GENES DETERMINING CELLULAR SENESCENCE IN YEAST

[75] Inventors: Leonard P. Guarente, Chestnut Hill; Nicanor Austriaco, Jr., Somerville; Brian Kennedy, Arlington, all of Mass.

[73] Assignee: Massachusetts Institute of Technology, Cambridge, Mass.

[21] Appl. No.: 08/396,001

[22] Filed: Feb. 28, 1995

Related U.S. Application Data

[63] Continuation-in-part of application No. PCT/US94/09351, Aug. 15, 1994, which is a continuation-in-part of application No. 08/107,408, Aug. 16, 1993, abandoned.

[51] Int. Cl.$^6$ .............................. C12Q 1/68; C12N 15/00; C12N 1/19; C07H 21/04
[52] U.S. Cl. ........................ 435/6; 435/172.3; 435/254.2; 536/23.74
[58] Field of Search ........................... 435/172.1, 254.11, 435/255.2, 254.2, 6, 172.3; 536/23.74

[56] References Cited

PUBLICATIONS

Hamlyn et al. EMBL/GenBank/DDBJ databases Accession No. Z46833, 1994.

Urrestarazu et al. EMBL/GenBank/DDBJ databases Accession No. Z28267, 1994.

Hirsch, H.R., "Accumulation of a Senescence Factor in Yeast Cells," *Experimental Gerontology*, 28(2):195–204 (1993).

Jazwinski, S.M., et al., "Replication Control and Differential Gene Expression in Aging Yeast," *Molecular Biology of Aging*, pp. 189–203 (1990).

Jazqinski, S.M., "Aging and Senescence of the Budding Yeast *Saccharomyces Cerevisiae*," *Molecular Microbiology*, 4(3):337–343.

Egilmez and Jazwinski, "Evidence for the Involvement of a Cytoplasmic Factor in the Aging of the Yeast *Saccharomyces cerevisiae*," *Journal of Bacteriology*, 171(1):37–42 (1989).

Sainsard–Chanet and Begel, "Transformation of Yeast and Podospora: Innocuity of Senescence–Specific DNAs," *Mol Gen Genet*, 204:443–451 (1986).

Miura and Sato, "Cellular Senescence in Yeast Caused by Carbon–Source Starvation," *J. Biochem.*, 76(3):593–601 (1974).

Miura and Yanagita, "Cellular Senescence in Yeast Caused by Carbon–Source Starvation," *J. Biochem.*, 72(1):141–148 (1972).

Longtine, Mark S. et al., "Telomere–Mediated Plasmid Segregation in *Saccharomyces cerevisiae* Involves Gene Products Required for Transcriptional Repression at Silencers and Telomeres," *Genetics*, 133:171–182 (1993).

Lee and Gross, "Conditional Silencing: The HMRE Mating–Type Silencer Exerts a Rapidly Reversible Position Effect on the Yeast HSP82 Heat Shock Gene," *Molecular and Cellular Biology* 13(2):727–738 (1993).

Sussel and Shore, "Separation of Transcriptional Activation and Silencing Functions of the RAP1–Encoded Repressor/Activator Protein 1: Isolation of Viable Mutants Affecting Both Silencing and Telomere Length," *Proc. Natl. Acad. Sci. USA*, 88:7749–7753 (1991).

Schnell, Rogene et al., "Genetic and Molecular Characterizations of Suppressors of SIR4 Mutations in *Saccharomyces cerevisiae*," *Genetics* 122:29–46 (1989).

Marshall, Mark et al., "Functional Domains of SIR4, a Gene Required for Position Effect Regulation in *Saccharomyces cerevisiae*," *Molecular and Cellular Biology*, 7(12):4441–4452 (1987).

Ivy, John M. et al., "Map Positions of Yeast Genes SIR1, SIR3 and SIR4," *Genetics III*, pp. 735–744 (1985).

Aparicio, Oscar M. et al., "Modifiers of Position Effect Are Shared Between Telomeric and Silent Mating–Type Loci in *S. cerevisiae*," *Cell*, 66:1279–1287 (1991).

Lundblad and Szostak, "A Mutant With a Defect in Telomere Elongation Leads to Senescence in Yeast," *Cell*, 57:633–643 (1989).

Jazwinski, S. Michael, "Genes of Youth: Genetics of Aging in Baker's Yeast," *ASM News*, 59(4):172–178 (1993).

D'Mello, N.P. et al., "Molecular Analysis of a Young–Specific Gene in the Yeast *Saccharomyces cerevisiae*," *Abstracts of the 92nd General Meeting of the American Society for Microbiology*, H–284, p. 230 (May 26–30, 1992).

Egilmez, Nejat K. et al., "Specific Alterations in Transcript Prevalence During the Yeast Life Span," *The Journal of Biological Chemistry*, 264(24):14312–14317 (1989).

Jazwinski, S. Michael et al., "Replication Control and Differential Gene Expression in Aging Yeast," *Molecular Biology of Aging*, pp. 189–203 (Mar. 1989).

Müller, Ilse et al., "Calendar Life Span Versus Budding Life Span of *Saccharomyces cerevisiae*," *Mechanisms of Aging and Development*, 12(1):47–52 (1980).

Urrestarazu et al., Protein Sequence Database, Accession No. S38114 (May 3, 1994).

*Primary Examiner*—James Ketter
*Assistant Examiner*—John S. Brusca
*Attorney, Agent, or Firm*—Hamilton, Brook, Smith & Reynolds, P.C.

[57] ABSTRACT

Methods of isolating mutant yeast cells with increased life span, as well as mutant yeast cells isolated by the methods, are disclosed. Also described are methods of identifying agents which increase life span of yeast cells, and methods of isolating genes which affect senescence in organisms.

19 Claims, 63 Drawing Sheets

```
1/1                                                              31/11
AAG CTT TAA CGG GAT CTT CTA ACA AAT AGC ATA ATA ACC AAA AAC CAG CTT CAG TGG
 K   L   *   R   G   D   L   L   T   N   I   *   N   T   P   K   N   Q   L   S   V   G
 S   F       *   I   S   F   S   T   Q   K   *       I       N       Q   A       W   G
 A   L       T       H       Y   N   K           Q       N   T   P   S   A   F   Q   W

61/21                                                            91/31
GAT CAG CCT ATC GAC ACG CCT ATC TTT TTA ACA GCG ATA CAA AAC CCG TTT ATG TCG TAT GGA
 D   Q   P   I   D   T   P   I   F   L   T   A   I   Q   N   P   F   M   S   Y   G
 I   S   A   Y   R   H   L   S   F   *   Q   R   S   N   T   P   F   C   V   M   E
 S       L       T           Y   F   N   R   A   H   K   T   P   L   Y   V   W   N

121/41                                                           151/51
ATT TCT ATA CTT GAC CCT ACC TTA TTT CTC GTC TAA CAA TAT GCC TAT TCT CCG TTT AAG GAT
 I   S   I   L   D   P   T   L   F   L   V   *   Q   Y   A   Y   S   P   F   K   D
 F   L   Y   L   *   P   Y   L   F   F   V       N   I   A   Y   L   R   V   K   I
     I   Y   T       R   T       Y   S   S       T   M   P   I   S       L   R   G

181/61                                                           211/71
AGG GCT TCG GGA AAG AGG CGC CTC AGG CAA GTC CTC GAA TAT GCC ATA GCA AAA AAA AGA
 R   A   S   G   K   R   R   L   R   Q   V   L   E   Y   A   I   A   K   K   R
 G   L   R   E   E   G   A   P   G   K   C   F   S   M   P   L   Q   K   K   K
     F       K       A       Q       N   I   R   N   E       K   R

241/81                                                           271/91
GAT TCG AAG ATC TAT GAA AAA TTT ATG CAG ATT CGT TGA GAG TTA GGA TTT GTC TTC CTC TTT
 D   S   K   I   Y   E   K   F   M   Q   I   R   *   E   L   G   F   V   F   L   F
 I   R   R   S   M   K   N   L   C   R   F   V   E   S   *   D   L   S   S   L   F
 F   E   D   L   *   K   I   Y   A   D   F   C   R   V   I   R   C   L   P   L

301/101                                                          331/111
TTA TGG TTA TAG GTT TCA TTC TAA AAT CAA ATT TTG TGT TTT GGA TAA AGA AAA TTC TTT
 L   W   L   *   V   S   F   *   N   Q   I   L   C   F   G   *   R   K   F   F
 Y   G   Y   R   F   H   S   K   I   K   F   C   V   L   D   K   E   K   L   F
 M   V       L       I   L       S       N   F   V   F   W   I   R   K   I   L
```

```
1621/541
TTC AAA AGT GTA TTT TCA AAT TCT CGC CAT CAA AAT TTG GTT TCA TCA TAG ATG CTA TTG
 F   K   S   V   F   S   N   S   R   H   Q   N   L   V   S   S   *   M   L   C   V
1651/551
                                                              CAA AAT TTG GTT TCA TCA TAG ATG CTA TTG
                                                               Q   N   L   V   S   H   I   D   A   C   V
1681/561
TAG AAC AAA ATA ATA TCA TTA CCA TTT CTA CTA AAC ATA AAC TTT GTT GTT GCG TAC AAA
 *   N   K   I   I   S   L   Y   F   L   L   N   I   N   F   V   V   A   Y   K
1711/571
                CCC ATA AAC TTT CTA TAC AAA ATA AAC TTT GTT GTT GCG TAC AAA
                 P   I   N   F   L   Y   K   I   N   F   V   V   A   Y   K
1741/581
AAT TAC TAA GCG TTT GTA CTC TAC AAC AAA TTT TCA AAA CTG TGA TTC TGC AGT
 N   Y   *   A   F   V   L   Y   N   K   F   S   K   L   *   F   C   S
1771/591
            TTT TCA AAA CTG TGA TTC TGC AGT
             F   S   K   L   *   F   C   S   V   F
1801/601
TCC TTC CTG GAT TAA CTG ATC AGT TCG ATT ATA TCA AAT TTC TAT CCA TTA AAA AAT TAT
 S   F   L   D   *   L   I   S   S   I   I   S   N   F   Y   P   L   K   N   Y
1831/611
                        GTA ATT ATA TCA AAT TTC TAT CCA TTA AAA AAT TAT
                         V   I   I   Y   I   S   N   F   S   L   *   K   L   F
1861/621
TCA AAG AAT TGG ACT TTT ACT TAT TGG CTG AAA TAT TTA ACC GTT TAT TGT CCA ATG GGG
 S   K   N   W   T   F   T   Y   W   L   K   Y   L   T   V   Y   C   P   M   G
1891/631
                                            AGT TAT TGG CTG AAA TAT TTA
                                             S   Y   I   L   *   N   F   L   *   E
1921/641
GTC AAC TAT CTT GTT TGA AGT TCT CCT CAA CTG TGG AAA AAT TCA CCT CCC AAA GGA CTG CAG
 V   N   Y   L   V   *   S   S   P   Q   L   W   K   N   S   P   P   K   G   L   Q
1951/651
                                ATG GGG GTG CCT CCC AAA GGA CTG CAG
                                 M   G   V   P   L   S   K   R   T   A
1981/661
TTA GAA TCA TTA ATA CTG GAT TTA TTG TTA ATA TTT CCT CAA AAA GGA CTG CAG
 L   E   S   L   I   L   D   L   L   L   *   I   *   N   K   R   T   A
2011/671
                ACA ATG GGG GTG CCT CCC AAA GGA CTG CAG
                 T   M   G   V   P   P   Q   *   N   G   S   V
```

FIG. 16E

```
2041/681                                                   2071/691
TTG CTT CTG ATG ACG TGA TTA ATG CTT CTA TGA ACA TTC TTT TGA CTA CCA TTG ATA TAT
 L   L   L   M   T   *   L   M   L   L   *   T   F   F   *   L   P   L   I   Y
 C   F   *   R   D   V   I   N   A   S   M   N   I   L   L   T   I   *   Y   I
 A   S   D   D   V   L   *   C   F   Y   E   H   S   F   L   D   T   H   D   F
2101/701                                              2131/711
TCA CAG TCA ATT TAA ATG TGC TAA TCA GGG ATA ATT TTG GTA ATT ATG CGT TAC AAA CGC
 S   Q   S   I   *   M   C   *   S   G   I   I   L   V   I   M   R   Y   K   R
 H   S   Q   F   K   C   A   N   Q   G   *   F   W   *   L   C   V   T   N   A
 T   V   N   L   N   V   L   I   R   D   N   F   G   N   Y   A   L   Q   T   L
2161/721
TAT TAG ACG TTA AGA ATT ATT CTC TGC TTG CTT ACA AAA ACA ATA GTA ACG CAA TTG
 Y   *   T   L   R   I   I   L   C   L   L   T   K   T   I   V   T   Q   L
 I   R   R   *   K   N   Y   S   A   C   L   Q   K   N   *   R   N   N   W
 L   D   V   L   E   L   F   L   A   Y   N   K   N   S   N   A   I   G
2221/741
GGC AAA ACA GCT CTA GTA CAT TGA ATT ACG GTA ACT TTT GTA ACA TTT TTT CAT TGA AAA
 G   K   T   A   L   V   H   *   I   T   V   T   F   V   T   F   F   H   *   K
 A   K   Q   L   *   Y   I   E   L   R   *   L   L   *   R   F   F   I   E   N
 Q   N   S   S   T   L   N   Y   G   N   F   C   N   D   F   S   L   K   I
2281/761
TTG GTA ACT TGA TTG TCC TTA CAA AAG AAT TAC TTC CAA GTA TTA AAA CTA CAT CCT ATG
 L   V   T   *   L   S   L   Q   K   N   Y   F   Q   V   L   K   L   H   P   M
 W   *   L   D   C   P   Y   K   R   I   T   S   K   Y   *   N   Y   I   L   C
 G   N   L   I   V   L   T   K   E   L   L   P   S   I   K   T   T   S   Y   A
2341/781
CAA AGA AAA TTA AGT TGA AAG CTT ATG CAG AAG CCA AAG CAG GTA TAC CAT TCA CTG
 Q   R   K   L   S   *   K   L   M   Q   K   P   K   Q   V   Y   H   S   L
 K   E   N   *   V   E   S   L   C   R   S   H   R   S   G   I   P   F   T   D
 K   K   I   K   V   K   L   Y   A   E   A   T   G   V   Y   T   I   H   H   *
2401/801                                              2431/811
ACA TAT CTC CTC AAG TCA CTG CAA TGA GTC ATA ACA ATC TTC AAA CGA TTA ACA ACG AAA
 T   Y   L   L   K   S   L   Q   *   V   I   T   I   F   K   R   L   T   T   K
 H   I   S   S   S   H   C   N   E   S   *   Q   S   S   N   D   *   Q   R   K
 T   Y   L   K   S   H   C   T   A   M   S   H   N   N   L   Q   T   I   N   E   N

```
2881/961
GAT TTA AGC AGC CTG GAT TTA TGA TGA ATG AAA CCG ACA AAA TTA ATG CTA ATC ACT TCT
 D   L   S   S   L   D   L   *   *   M   K   P   T   K   L   M   L   I   T   S
 I   *   A   A   W   I   Y   D   M   *   N   R   Q   N   *   C   *   S   L   L
 F   K   Q   P   G   F   M   M   E   T   D   K   I   N   A   N   H   F   S
2941/981
CGC CAT ACT CTA ATG CAA GTC AAA ACT TCA ATG AAT CTT TTG TGC CTC GTA TGC AAT
 R   H   T   L   M   Q   V   K   T   S   M   N   L   L   C   L   V   C   N
 A   I   L   *   C   K   *   S   L   Q   *   I   F   C   A   S   Y   A   I
 P   Y   S   N   A   N   S   Q   N   F   N   E   S   F   V   P   R   M   Q   Y
3001/1001
ATC AAA CGG AAG GTG CAA ACT GGG ATT CAA GTT TGT CAA TGA AGT CGC AGC ATA TTG GTC
 I   K   R   K   V   Q   T   G   I   Q   V   C   Q   *   S   R   S   I   L   V
 S   N   G   R   C   K   L   G   F   K   F   V   N   E   V   A   A   Y   W   S
 Q   T   E   A   N   W   D   S   S   L   S   M   K   S   Q   H   I   G   Q
3061/1021
AAG GCC CAT ATA ATC AAG TTA ATA TGA ACG GCA ACG CTA GTA TTT CCA ATA TGC CTG CCA
 K   A   H   I   I   K   L   I   *   T   A   T   L   V   F   P   I   C   L   P
 R   P   I   *   S   *   Y   N   M   S   R   *   Y   *   F   Q   Y   A   C   H
 G   P   Y   N   Q   V   N   M   S   R   N   A   S   I   S   N   M   P   A   M
3121/1041
TGA ATA CCG CTA GAA CAT CTG ATG AAC TTC AAT TCA CTT TGC CAT AAT ACT TTT TTT TCT
 *   I   P   L   E   H   L   M   N   F   N   S   L   C   H   N   T   F   F   S
 E   Y   R   *   N   I   *   *   T   S   I   H   F   A   I   I   L   F   F   L
 N   T   A   R   T   S   D   E   L   Q   F   T   L   P   *   Y   F   F   F
3181/1061
TTC TTT TTC TTT CCT TCT TAC TGT ACA AAT ATT TTA CGC AGA AAT CAA AGA CAA AAG AAA
 F   F   F   F   P   S   Y   C   T   N   I   L   R   R   N   Q   R   Q   K   K
 S   F   S   F   L   L   T   V   Q   K   Y   *   A   E   I   K   D   K   R   K
 L   F   L   S   F   L   L   Y   K   N   I   F   Y   T   K   S   K   T   K   E
3241/1081
AAT AAA AAA TAA AAA ATA AAA ATC AAG TCA ACT AAG CAA TGA CGT CCT AAA GTC CCA AAA
 N   K   K   *   K   I   K   I   K   S   T   K   Q   *   R   P   K   V   P   K
 *   K   N   K   N   K   K   N   *   A   L   S   N   D   V   L   K   S   Q   K   I
3271/1091
```

FIG. 16H

```
3301/1101                          3331/1111
TTT GAG CCG GAA AAA AAT GGT AAA GCA AAC TAT TGC CAT CTT TAT ATT TTG TAT TCT GTT
 F   E   P   E   K   N   G   K   A   N   Y   C   H   L   Y   I   L   Y   S   V
 L   *   S   R   K   M   V   *   S   K   L   P   S   L   Y   F   V   F   C   F
    A   G   K   K   W       Q   T   I   A   I   F   F   C   I   L   F
              3361/1121                          3391/1131
TCC GAA CAC GTA TCC AAA ATC CTC CCA CTG CCT TTG CAG GGT TAG CAT TGC TCC CTA CCA
 S   E   H   V   S   K   I   L   P   L   P   L   Q   G   *   H   C   S   L   P
 P   N   T   Y   P   K   S   S   H   C   L   C   R   V   S   I   A   L   P   Y   Q
    R   T   R   I   Q   N   P   P   T   A   F   A   G   L   A   L   L   P   T   K
3421/1141                          3451/1151
AAA TGA TCT AAT TTT TTT TTG AAT CGT TTT TTG TC
 K   *   S   N   F   F   L   N   R   F   L
 N   D   L   I   F   F   F   E   S   F   F   V
    M   I   *   F   F   F   *   I   V   F   C
```

FIG. 16I

```
1/1
GTG TCT TCC ATG GAG TGA ATT GTG ATT TGT GAA TTA TAT CTG TCC AAT ACC GTT GCC TTG
 V   S   S   M   E   *   I   V   I   C   E   L   Y   L   S   N   T   V   A   L
61/21                                                       31/11
 V   F   H   G   V   N   C   D   L   *   F   V   *   I   I   S   V   Q   Y   I
TTG GGA GCT CAG ATA GAA AAG ACA TCT TAA TTC CAG ACA GTC TAT TCT CTG TCT ATT TCT
 L   G   A   Q   I   E   K   T   S   *   F   Q   T   V   Y   S   L   S   I   S
                                    91/31
 W   E   L   R   *   K   R   D   I   L   I   P   D   S   L   F   S   V   F   L
                                                            151/51
CTT TGT GAC TGC AAA TTT TAA TTT GTG ACG CCT TTT CTT ATT ACT CAT GTA TTT GTC ACT
 L   C   D   C   K   F   *   F   V   T   P   F   L   I   T   H   V   F   V   T
 F   V   *   L   Q   I   L   I   C   D   A   F   S   Y   Y   I   L   M   Y   L
181/61                                                      211/71
CTT GAC GAT TGT TTT TTT TCT ATA TTT TTT TTT TGG GGT CCT CCA GAG AAT AAA AAA AAA
 L   D   D   C   F   F   S   I   F   F   F   W   G   P   P   E   N   K   K   K
 L   *   R   L   V   F   F   L   Y   I   F   F   F   L   G   V   L   Q   R   I   K   N
241/81                                                      271/91
TAA TGA TCA ATA TAG TAG ATA GTA TAG TTA TAT TCT TAT TCG TTG CAC CTT GTT TAA CAA
 *   *   S   I   *   *   I   V   *   L   Y   S   Y   S   L   H   L   V   *   Q
 N   D   Q   Y   R   *   D   S   I   V   Y   I   L   F   V   A   P   C   L   T   N
301/101                                                     331/111
ATC ACT CAG ACT CAA AGA GAA TAT CGG TTG GTT ATC TCT CTC CGA AGG TGA ACA GCA AAC
 I   T   Q   T   Q   R   E   Y   R   L   V   I   S   L   R   R   *   T   A   N
 S   L   R   L   K   E   N   I   G   W   L   S   P   K   V   E   G   E   Q   T
361/121                                                     391/131
AGT ACC TCA CGT TTT CTT TTT GAA TAG TTT TTT TTG AAA CAG TGA ACA GCA AAC TTT
 S   T   S   R   F   L   F   E   *   F   F   L   K   Q   *   N   R   K   L   S
 V   P   H   V   F   L   F   *   I   V   F   F   C   F   F   L   K   N   F
```

FIG. 17A

```
421/141
CTT CCG TAT ATT ACA TTG TAC ATT ATT TTT ATT GTA TTT TAG TTT CCA ACG TTA GGA TTT
 L   P   Y   I   T   L   Y   I   I   F   I   V   F   *   F   P   T   L   G   F
 F   R   I   Y   H   C   T   L   Y   Y   L   F   Y   C   I   L   Y   F   Q   R   *   D   L
 S   V                                                                                 N   R   I   *
                          451/151
481/161
GAG CCG TCA TTA ATA TTA TTC GTT TTT GTA CAC TAT TCC AGA CGA TTT ATT TTT AGT ACA
 E   P   S   L   I   L   F   V   F   V   H   Y   S   R   R   F   I   F   S   T
 S   R   H   *   Y   Y   S   F   L   *   T   I   P   D   D   L   Y   F   L   V   H
 A   V   I   N   I   I   R   F   C   L   F   Q   T   I   F   *   Y   T
                          511/171
541/181
CTT AAA ATT CCT GTT GAT ATT GTC CAC TAG TTC TCT TTT CAT ATT TTA TTT TCG CTT ATT
 L   K   I   P   V   D   I   V   H   *   F   S   F   H   I   L   F   S   L   I
 L   K   F   L   L   *   Y   C   P   L   V   L   F   S   Y   F   I   F   R   L   F
 *   N   S   C   *   Y   I   L   S   T   L   F   I   F   A   Y   S
                          571/191                          631/211
601/201
CTT TAG GTT CTT TTA AGA GTC TCT GTT CAT TTT CCG TTC TTA CTG TTT CTT TGT CCT CGA
 L   *   V   L   L   R   V   S   V   H   F   P   F   L   L   F   L   C   P   R
 F   R   F   F   *   E   S   L   C   S   F   S   R   Y   C   F   F   V   L   D
 L   G   S   F   K   R   V   L   F   P   F   L   L   F   S   L   S   I
661/221
TAT CTT TTA AGA AAG AGA GAA CTA AGC GCT GTA ACA TTT TTA AGT GGA CCT ACG TTA TGT
 Y   L   L   R   K   R   E   L   S   A   V   T   F   L   S   G   P   T   L   C
 I   F   *   E   K   E   R   T   K   R   C   *   H   F   *   V   D   L   R   Y   V
 S   F   K   K   E   R   N   *   K   S   A   L   N   I   F   K   W   T   Y   V   M   S
                          691/231                          751/251
721/241
CTA CAA AAG GTT TGA AAG AAA TCG ATG ATG TAC CAT CAG TAG ACC CTG TCG TTT CAG
 L   Q   K   V   *   K   K   S   M   M   Y   H   Q   *   T   L   S   F   Q
 Y   K   R   F   E   R   N   R   *   C   T   I   S   R   P   C   R   F   R
 T   K   G   L   K   E   I   D   D   V   P   S   V   D   P   V   V   S   E
```

FIG. 17B

```
781/261
AAA CAG TCA ATT CTG CTT TAG AGC AGT TGC AAC TAG ATG ATC CAG AGG AAA ACG CCA CCT
 K   Q   S   I   L   L   *   S   S   C   N   *   M   I   Q   R   K   T   P   P
     N   S   Q   F   C   F   R   A   V   A   T   R   *   S   R   E   E   N   A   T   H   L
         T   V   N   S   A   L   E   Q   L   Q   L   D   D   P   E   E   N   A   T   S
                                                            811/271
841/281
CTA ATG CAT TTG CGA ATA AAG TTT CTC AAG ATT CTC AAT TCG CTA ATG GCC CTC CGT CGC
 L   M   H   L   R   I   K   F   L   K   I   L   N   S   L   M   A   L   R   R
 *   C   I   C   E   *   S   F   S   Q   D   S   Q   F   A   N   G   P   S   V   A
     N   A   F   A   N   K   V   S   Q   D   S   Q   F   A   N   G   P   P   S   Q
901/301                                             871/291
AAA TGT TTC CAC ATC CAC AAA TGA TGG GTG GAA TGG GCT TCA TGC CCT ACT CTC AAA TGA
 K   C   F   H   I   H   K   *   W   V   E   W   A   S   C   P   T   L   K   *
     N   V   S   T   S   T   N   D   G   W   N   G   L   H   A   L   L   S   N   D
         M   F   P   H   P   Q   M   M   G   G   M   G   F   M   P   Y   S   Q   M   M
961/331                                             931/311
TGC AGG TTC CTC ATA ATC CTT GTC CAT TTT TTC CGC CCC CTG ATT TTA ATG ATC CAA CAG
 C   R   F   L   I   I   L   V   H   F   F   R   P   L   I   L   M   I   Q   Q
     A   G   S   S   *   S   L   S   I   F   F   S   A   P   *   F   *   N   S
         Q   V   P   H   N   P   C   P   F   F   L   P   P   D   F   N   D   P   T   A
1021/341                                            991/331
CAC CAT TGA GTA GCT CGC CCT TGA ATG CAG GCG GTC CAC CAA GCG CGG TAG CAA TCG CAT
 H   H   *   V   A   R   P   *   M   Q   A   V   H   Q   A   R   *   Q   S   H
     T   I   E   *   L   A   L   E   C   R   R   S   T   N   V   L   F   K   N   D
         P   L   S   S   P   *   N   P   C   P   G   P   P   M   L   F   K   N   D   S
1081/361                                            1051/351
CAC TTC CAT TTC AAA TGC TGT CTT CGG GTG CTG CGG TAG CAA CTC CAA AAG GTG GAC AAA ATC
 H   F   H   F   K   C   C   L   R   V   L   R   *   Q   L   Q   K   V   D   K   I
     T   S   I   S   N   A   V   F   G   C   C   G   S   N   S   R   W   T   K   S
         L   P   F   Q   M   L   S   G   A   A   V   A   T   Q   G   G   Q   N   L
1141/381                                            1111/371
TAA ACC CAT TGA TAA ATG ACA ATT CAA TGA AGG TAT TGC CAA TCG CAT CGG CTG ATC CGT
 *   T   H   *   *   M   T   I   Q   *   R   Y   C   Q   S   H   R   L   I   R
     N   P   I   D   K   *   Q   F   N   E   G   I   A   N   R   I   G   *   S   V
         K   P   L   I   N   D   N   S   M   K   V   L   P   I   A   S   A   D   P   L
                                                    1171/391
FIG. 17C
```

```
1201/401
TAT GGA CTC ATT CAA ACG TAC CAG GAT CAG CAT CTG TAG CCA TTG AAG AAA CCA CCG CTA
 Y   G   L   I   Q   T   Y   Q   D   Q   H   L   *   P   L   K   K   P   P   L
 M   D   S   F   K   R   T   T   R   I   S   I   C   S   H   *   R   N   H   R   Y
 W   T   H   S   N   V   P   G   S   A   S   V   A   I   E   E   T   T   A   T
1261/421
CTC TAC AAG AAA GCC TAC CAT CTA AGG GCA GGG AGT CTA ATA ATA AGG CTA GTT CGT TCA
 L   Y   K   K   A   Y   H   L   R   A   G   S   L   I   I   R   L   V   R   S
 S   T   R   K   P   T   I   *   G   Q   G   V   *   *   *   G   *   F   V   Q
 L   Q   E   S   L   P   S   K   G   R   E   S   N   N   K   A   S   F   R   R
1321/441
GAA GAC AAA CTT TTC ATG CTT TAT CAC CAA CTG ACC TTA TCA ATG CGG CCA ACA ATG TAA
 E   D   K   L   F   M   L   Y   H   Q   L   T   L   S   M   R   P   T   M   *
 K   T   N   F   S   C   F   I   T   N   *   P   Y   Q   C   G   Q   Q   C   N
 R   Q   T   F   H   A   L   S   P   T   D   L   I   N   A   A   N   N   V   T
1381/461
CCT TGT CAA AGG ACT TCC AAT CTG ACA TGC AGA ATT TTT CTA AGG CTA AGA AAC CGT CTG
 P   C   Q   R   T   S   N   L   T   C   R   I   F   L   R   L   R   N   R   L
 L   V   K   G   L   P   I   *   H   A   E   F   F   *   G   *   E   T   V   C
 S   K   D   F   Q   S   D   M   Q   M   Q   N   F   S   K   A   K   K   P   S   V
1441/481
TAG GAG CTA ACA ATA CTG CAA AAA CCA CTC AAT CCA TAT CTT TTG ATA ATA CTC CCT
 *   E   L   T   I   L   Q   K   P   L   N   P   Y   L   L   I   I   L   P
 R   S   *   Q   Y   C   K   N   Q   *   T   H   I   F   *   *   Y   S   L
 G   A   N   N   T   A   K   T   R   L   I   S   I   H   I   S   F   D   N   T   P   S
1501/501
CCT CAA CGT CAT TTA TAC CCC CAA CCA ATA GTG TTT CTG AGA AAT TAT CCG ATT TCA AAA
 P   Q   R   H   L   Y   P   Q   P   I   V   F   L   R   N   Y   P   I   S   K
 L   N   V   I   Y   T   P   N   Q   *   C   F   *   E   I   I   R   F   Q   N
 S   T   S   F   I   P   P   T   N   S   V   S   E   K   L   S   D   F   K   I
1561/521
TAG AAA CCT CGA AGG AGG ATT TGA TTA ATA AAA CTG CAC CAG CTA AAA AAG AGA GTC CTA
 *   K   P   R   R   R   I   *   L   I   K   L   H   Q   L   K   K   R   V   L
 R   N   L   E   G   G   F   *   L   *   K   N   C   T   S   *   K   R   E   S   Y
 E   T   S   K   E   D   L   I   N   K   T   A   P   A   K   K   K   S   P   T
```

FIG. 17D

```
1621/541
CAA CTT ATG GTG CAG CAT ATC CAT ATG GGG GAC CTT TAC TTC AAC CAA ATC CTA TTA TGC
 Q   L   M   V   Q   H   I   H   M   G   D   L   Y   F   N   Q   I   L   L   C
 N   L   W   C   S   I   W   Y   T   F   S   T   K   S   Y   Y   A
 T   Y   G   A   A   Y   P   V   G   G   P   L   L   Q   P   N   P   I   M   P
                                                1651/551
1681/561
CAG GCC ACC CAC ATA TAT CCT CCC CTA TCT ATG GTA TTA GAT CAC CTT TTC CTA ATT
 Q   A   T   H   I   Y   P   P   L   S   M   V   L   D   H   L   F   L   I
 R   P   P   T   H   I   *   Y   I   L   P   Y   I   W   Y   *   I   T   F   S   *   F
 G   H   P   H   N   I   S   P   I   Y   G   I   R   S   P   F   P   N   S
                    1711/571                    1771/591
1741/581
CTT ATG AAA TGG GCG CGC AAT TTC AAC CTT TCT CTC CGA TTT TAA ATC CTA CGA GTC ATT
 L   M   K   W   A   R   N   F   N   L   S   L   R   F   *   I   L   R   V   I
 L   *   N   G   A   Q   F   Q   P   F   L   S   D   F   L   K   S   Y   E   S   F
 Y   E   M   G   R   A   I   S   T   F   *   I   N   P   T   S   H   S
1801/601
CAC TAA ATG CAA ATT CTC CAA TTC CTC TAA CCC AAT CGC CAA TTC ATC TTG CAC CAG TTT
 H   *   M   Q   I   L   Q   F   L   *   P   N   R   Q   F   I   L   H   Q   F
 T   K   C   K   F   S   N   S   P   L   T   Q   S   P   I   H   L   A   P   V   L
 L   N   A   N   P   I   P   L   P   K   P   I   A   N   S   S   C   T   S   F
1861/621
TAA ACC CTA GTT CAA ATT CTG TTG CCT TTT CAG ATA TGA AGA ATG ATG MTG GTA AGC CCA
 *   T   L   V   Q   I   L   L   P   F   Q   I   *   R   M   M   M   V   S   P
 K   P   *   F   K   I   L   C   L   F   S   R   Y   E   E   *   W   *   A   H
 N   P   S   S   N   S   V   A   F   S   D   M   K   N   D   G   K   P   T
1921/641
CCA CCG ATA ACG ACA AGG CGG GTC CAA ATG TTA GGA TGG ATT TAA TAA ATC CTA ATC TTG
 P   P   I   T   T   R   R   V   Q   M   L   G   W   I   *   *   I   L   I   L
 H   R   *   R   Q   G   G   S   K   C   *   D   G   F   N   K   S   *   S   W
 T   D   N   D   K   A   G   P   N   V   R   M   D   L   I   N   P   N   L   G
1981/661
GGC CAT CAA TGC AAC CTT TCC ACA TAT TAC CTC CCC AGC AAA ACA CCC CTC CTC CCT
 G   H   Q   C   N   L   S   T   Y   Y   L   P   S   K   T   P   L   L   P
 A   I   N   A   T   F   P   H   I   I   L   P   P   Q   N   T   P   S   S   L
 P   S   M   Q   P   F   H   I   L   P   P   Q   Q   K   H   P   P   P   P   W
                                                2011/671
                               FIG. 17E
```

```
2041/681
GGC TTT ATA GCA CTC CAC CTC CCT TCA ACG CAA TGG TTC CGC CTC ATT TGT TGG CTC AAA
 G   F   I   A   L   H   L   P   S   T   Q   W   F   R   L   I   C   W   L   K
 A   L   Y   *   S   T   P   P   P   F   N   A   S   F   V   G   S   K
                                              2071/691
2101/701
ATC ATA TGC CGT TAA TGA ATA GCG CCA ATA ATA AAC ATG GTC GTA ATA ACA ATA GCA
 I   I   C   R   *   *   I   A   P   I   I   N   M   V   V   I   T   I   A
 S   Y   A   V   N   E   *   R   Q   *   *   T   W   S   *   *   Q   *   H
 H   M   P   L   M   N   S   A   N   N   K   H   H   G   R   N   N   N   S   M
                                              2131/711                2161/721
TGT CAA GTC ATA ATG ACA ATG ACA ATT CTA GTA ATT TTG GTA AAA ACA ATA AAG ACA CAG
 C   Q   V   I   M   T   M   T   I   L   V   I   L   V   K   T   I   K   T   Q
 V   K   S   *   *   Q   *   Q   H   W   *   F   *   L   Q   *   *   R   H   R
 S   S   H   N   D   N   I   G   N   S   N   Y   N   N   K   D   T   G
                                              2191/731                2221/741
GTC GTT CTA ACG TTG GTA AAA ATA TGA AAA ACA GTT ATC ATG GCT ACT ATA ATA
 V   V   L   T   L   V   K   I   *   K   T   V   I   M   A   T   I   I
 S   F   *   R   W   *   N   E   K   Y   *   E   K   Q   *   L   S   W   L   L   *
 R   S   N   V   G   K   M   K   N   M   K   N   S   Y   H   G   Y   Y   N
                                              2251/751                2281/761
ACA ATA ATA ATA ATA ATA ACA ATA ACA TGA AAA ATA ACA GTT ATC ATG CTA CCA ACA GCA
 T   I   I   I   I   I   T   I   T   *   K   I   T   V   I   M   L   P   T   A
 Q   *   *   *   *   *   Q   *   Q   *   *   *   C   Y   Q   Q   Q
 N   N   N   N   N   N   N   N   N   N   N   S   N   A   T   N   S   N
                                              2311/771                2341/781
ACA GCG CGG AAA AAC AAC GTA AAA TTG AGG AGT CGT CGA GAT TTG CGG ACG CAG TTT TAG
 T   A   R   K   N   N   V   K   L   R   S   R   R   D   L   R   T   Q   F   *
 Q   R   G   K   T   T   *   N   *   E   V   V   E   I   C   G   R   S   F   R
 S   A   E   K   Q   R   K   I   E   E   S   S   R   F   A   D   A   V   L   D
                                              2371/791                2401/801
ACC AAT ATA TCG GAA GTA TTC ACT CAT TGT GTA AAG ACC AAC ATG GTT GTC GTT TTC TGC
 T   N   I   S   E   V   F   T   H   C   V   K   T   N   M   V   V   V   F   C
 P   I   Y   R   K   Y   S   L   I   V   *   R   P   T   W   L   S   F   S   A
 Q   *   *   I   G   S   I   H   S   L   C   K   D   Q   H   G   C   R   F   L   Q
                                              2431/811

FIG. 17F
```

```
2461/821
AAA AGC AGT TGG ATA TTC TCG GCA GTA AGG CGG ACC GAA TTT TTG AAG AAA CTA AGG
 K   S   S   W   I   F   S   A   V   R   R   T   E   F   L   K   K   L   R
2491/831
AAA GCA GTT CGG ACC GAA TTT TTG AAG AAA CTA AGG
 K   A   V   *   G   P   N   F   *   R   N   *   K   G
2521/841
ATT ATA CGG TTG AAT TGA TGA CTG ATT CAT TCG GTA ATT ATT TGA TCC AGA AGC TAT TGG
 I   I   R   L   N   *   *   L   I   H   S   V   I   I   *   S   R   S   Y   W
2551/851
                                                  A   D   P   E   A   I   G
2581/861
                                           Y   L   I   Q   K   L   L   E
AAG AGG TTA CCA CAG AAC AAA GAA TCG TAC TCA CAA AAA TAT CTT CCC CTC ATT TTG TCG
 K   R   L   P   Q   N   K   E   S   Y   S   Q   K   Y   L   P   L   I   L   S
2611/871
                                           R   G   Y   H   R   N   R   I   V   L   T   K   I   S   P   H   F   V   R
2641/881
AAA TTT CCT TAA ACC CTC ATG GTA CTA GGG CAT TAC AAA AAC TCA TTG AAT GCA TCA AAA
 K   F   P   *   T   L   M   V   L   G   H   Y   K   N   S   L   N   A   S   K
2671/891
                                           E   V   T   E   Q   R   *   G   T   R   A   L   Q   I   T   K   L   I   E   C   I   K   T
2701/901
CAG ATG AAG AAG CAC AGA TTG TTG ATT TTG TTG ATT CTT TAC GCC CTT ATA CTG TCC AGT TGA GTA
 Q   M   K   K   H   R   L   L   I   L   F   F   L   Y   A   L   I   L   S   S   *   V
2731/911
                                           N   F   L   K   P   *   T   L   M   V   Y   *   R   A   T   P   P   Y   T   V   Q   L   S   K
2761/921
AGG ATT TAA ATG GTA ATC ATG TTA TTC AAA AAT GTT TGC AAA GGT TGA AGC CTG AAA ACT
 R   I   *   M   V   I   M   L   F   K   N   V   C   K   G   *   S   L   K   T
2791/931
                                           D   E   E   A   Q   I   V   D   C   C   *   F   K   S   K   M   F   A   K   V   E   A   *   K   L
2821/941
TCC AGT TTA TCT TTG ACG CAA TCT CTG ATA GCT GTA TTG ATA TTG CTA CTC ATA GAC ACG
 S   S   L   S   L   T   Q   S   L   I   A   V   L   I   L   L   L   I   D   T
2851/951
                                           Q   F   I   F   D   A   I   S   D   S   C   I   D   I   A   T   H   R   G
```

FIG. 17G

```
2881/961
GGT GTT GCG TTT TGC AAC GTT GTC TAG ATC ATG GGA CTA CAG AAC AAT GTG ACA ATC TGT
 G   V   A   F   C   N   V   V   *   I   M   G   L   Q   N   N   V   T   I   C
 V   C   R   F   A   T   L   S   R   S   W   D   Y   R   T   M   *   Q   S   V
 C   C   V   L   Q   R   C   L   D   H   G   T   E   Q   C   D   N   L   C
2941/981                                          2971/991
GTG ATA AGT TGC TAG CCC TTG TTG ATA AAT TAA CTT TGG ATC CAT TTG GCA ACT ATG TGG
 V   I   S   C   *   P   L   L   I   N   *   L   W   I   H   L   A   T   M   W
 *   *   V   A   S   P   C   *   *   I   N   F   G   S   I   W   Q   L   C   G
 D   K   L   L   A   L   V   D   K   L   T   L   D   P   F   G   N   Y   V   V
3001/1001                                         3031/1011
TGC AAT ATA TAA TTA CCA AAG AGG CTG AGA ACA AAT ATG ATT ATA CGC ATA AAA TTG
 C   N   I   *   L   P   K   R   L   R   T   N   M   I   I   R   I   K   L
 A   I   Y   *   Y   Q   R   G   *   E   Q   I   *   L   Y   A   *   N   C
 Q   Y   I   N   T   K   E   A   E   K   N   K   Y   D   Y   T   H   K   I   V
3061/1021                                         3091/1031
TCC ACC TGT TGA AAC CAA GAG CCA TCG AAC TTT CTA ATA AAT TTG GAT CAA ATG TGA
 S   T   C   *   N   Q   E   P   S   N   F   L   I   N   L   D   Q   M   *
 P   P   V   E   T   K   R   H   R   T   F   *   *   I   W   I   K   C   D
 H   L   L   K   P   R   A   I   E   L   S   I   H   K   F   G   S   N   V   I
3121/1041                                         3151/1051
TTG AAA AAA TCT TGA AGA CGG GTA TTC AAT CAT TGT TGA AGC CAA CTA TTG TGG AAA TTT TAA ATA
 L   K   K   S   *   R   R   V   F   N   H   C   *   S   Q   L   L   W   K   F   *   I
 *   K   N   L   E   D   G   Y   S   I   I   V   E   A   N   Y   C   G   N   F   K   *
 E   K   I   L   K   T   R   V   L   Q   S   L   L   N   Q   T   I   V   E   I   L   N
3181/1061                                         3211/1071
ATG GTG GCG AGA CGG GTA TTC AAT CAT TGT TGA ATG ATA GCT ACG GAA ATT ACG TTT TAC
 M   V   A   R   R   V   F   N   H   C   *   M   I   A   T   E   I   T   F   Y
 W   W   R   D   G   Y   S   I   I   V   E   *   *   L   R   K   L   R   F   T
 G   G   E   T   G   I   Q   S   L   L   N   D   S   Y   G   N   Y   V   L   Q
3241/1081                                         3271/1091
AGA CAG CAT TAG ACA TTT CTC ATA AGC AAA ATG ACT ATC TCT ATA AAA GAC TAT CAG AGA
 R   Q   H   *   T   F   L   I   S   K   M   T   I   S   I   K   D   Y   Q   R
 D   S   I   R   H   F   S   *   A   K   *   L   S   L   *   K   T   I   R   D
 T   A   L   D   I   S   H   K   Q   N   D   Y   L   Y   K   R   L   S   E   I
```

FIG. 17H

```
3301/1101                                           3331/1111
TTG TGG CGC CTT TAC TGG TGG GCC CCA TAA GAA ATA CAC CTC ATG GTA AAA GAA TCA TCG
 L   W   R   L   Y   W   W   A   P   *   E   I   H   L   M   V   K   E   S   S
 C   G   A   F   T   G   G   P   H   K   *   R   Y   T   P   *   K   N   H   R
 V   A   P   L   V   V   G   P   I   R   N   T   P   H   G   K   R   I   I   G
3361/1121                                           3391/1131
GAA TGT TAC ATT TAG ATT CAT AGT TGA TAC ATA TAT CCT CAG TTT AGC TTT TTT TAC GTT
 E   C   Y   I   *   I   H   S   *   Y   I   Y   P   Q   F   S   F   F   Y   V
 N   V   T   H   L   D   S   *   L   I   H   I   S   S   V   *   L   F   L   R
 M   L   L   H   *   F   I   V   D   I   Y   I   L   S   F   L   A   F   T   *
3421/1141                                           3451/1151
AGC CTC ATA TAA TAT CTT TTG TAC AAT ACT AAA ATA CAT CAT TTT TTT TTT CGT TGA GGA
 S   L   I   *   Y   L   L   Y   N   T   K   I   H   H   F   F   F   R   *   G
 A   S   Y   N   I   F   C   T   I   L   K   Y   I   I   F   F   F   V   E   D
 P   H   I   *   Y   S   F   V   Q   Y   *   N   T   S   F   F   F   S   L   R   I
3481/1161                                           3511/1171
TCA AAT GAA TAT CCA AAG CAA AAA AAA TAG GAA TTT TCA CTT TAT GGT ATA CTG GTA AAT
 S   N   E   Y   P   K   Q   K   K   *   E   F   S   L   Y   G   I   L   V   N
 Q   M   N   I   Q   S   K   N   R   M   R   N   F   H   F   M   V   Y   W   *   I
 K   *   I   S   K   A   K   K   K   I   G   I   F   T   L   W   Y   T   G   K
3541/1181                                           3571/1191
AGT GTT GAA TAT CCA AAG ATA AGA GAA GGA GAT CGC CCT AGA AAA CAG AAT GTT ATT TAA ATA
 S   V   E   Y   P   K   I   R   E   G   D   R   P   R   K   Q   N   V   L   I   *   I
 V   L   K   *   I   R   E   E   K   E   I   A   L   E   N   R   M   F   L   Y   K   *
 C   *   R   N   K   S   *   K   R   R   S   P   *   K   T   E   C   S   Y   L   N   K
3601/1201                                           3631/1211
AGT AAA CTC AAA AGA AAA AAA AAA GGA AGG AAG TTT TTG AGA ACT TTT ATC TAT ACA AAC
 S   K   L   K   R   K   K   K   G   R   K   F   L   R   T   F   I   Y   T   N
 V   N   S   K   E   K   K   K   E   G   S   F   *   E   L   L   S   I   Q   T
 *   T   Q   K   R   N   K   K   R   K   E   V   F   E   N   F   Y   L   Y   K   R
3661/1221                                           3691/1231
GTA TAC GTT TAA CTA TCT GGA TAA ACG TCG CTC CAC AGG ATA CTG TAG AGG TCC TCA AGA
 V   Y   V   *   L   S   G   *   T   S   L   H   R   I   L   *   R   S   S   R
 Y   T   F   N   Y   L   D   K   R   R   S   T   G   Y   C   R   G   P   Q   D
 I   R   L   T   I   W   I   N   V   A   P   Q   D   T   V   E   V   L   K   I

FIG. 17I
```

```
3721/1241
TCA CCG TTA ACA AAT TCA TCT AGT GTC CCC AAA TTA AAA CTA GTT GCA GAA AAA TTG
 S   P   L   T   N   S   S   S   V   P   K   L   K   L   V   A   E   K   L
 H   R   Y   *   Q   I   H   L   *   C   P   N   *   N   *   L   Q   K   N   C
 T   V   I   N   K   F   I   S   V   S   P   Q   I   K   T   S   C   R   K   I   V
3781/1261                                          3811/1271
TTA CTG TTG TTG ATA TTG TTA ATA TTG TTT TTA TTG TTT TTG TTG TTG TTG ATT TCA
 L   L   L   L   I   L   L   I   L   F   L   L   F   L   L   L   L   I   S
 Y   C   C   C   *   Y   C   *   Y   C   F   Y   C   C   C   C   C   *   F   H
 T   V   V   V   N   I   V   N   I   V   F   I   V   V   V   V   V   D   F   I
3841/1281                                          3871/1291
TTT GTG TTC ATA AAT GGT ACT TGT ACT GAA GTG GGT ATT TGC TGC TGA GCA TTG ATT GGT
 F   V   F   I   N   G   T   C   T   E   V   G   I   C   C   *   A   L   I   G
 L   C   S   *   M   V   L   V   L   K   W   V   F   A   A   E   H   *   L   V
 C   V   H   K   W   Y   L   Y   *   S   G   Y   L   L   L   S   I   D   W   F
3901/1301                                          3931/1311
TTA TTA GAT TGG ACT TGC GAA TTA TTT TGC CCA TTT GTT GGT TGC GCG TAA TCG GGA TTG
 L   L   D   W   T   C   E   L   F   C   P   F   V   G   C   A   *   S   G   L
 Y   *   I   G   L   A   N   Y   F   A   H   L   L   V   A   R   N   R   D   *
 I   R   L   D   L   R   I   I   L   P   I   C   W   L   R   V   I   G   I   D
3961/1321                                          3991/1331
ATC ATA TCA GAC ACG GAT AAT GAC CTA AAT GAA GGC AAT T
 I   I   S   D   T   D   N   D   L   N   E   G   N
 S   Y   Q   T   R   I   M   T   *   M   K   A   I
 H   I   R   H   G   *   *   P   K   *   R   G   Q
```

FIG. 17J

```
1/1
gaa gat cgg ggg gct gaa atc cat ctt cat cct acc gct cct acc gtg ttg gtg gaa tga
 E   D   R   G   A   E   I   H   L   H   P   T   A   P   L   V   L   V   E   *
 K   R   S   G   G   *   N   P   S   S   I   F   P   P   L   R   P   C   W   N
 R   R   I   G   A   K   S   N   P   S   Y   R   S   A   R   P   V   W   G   E
                          31/11                                    91/31              M   S gcg ttg cat gtg tct tga aga gaa aag cag tgc ttt ggc agg act ctt tca gcc ccc acc
 A   L   H   V   S   *   R   E   K   Q   C   F   G   R   T   L   S   A   P   T
 R   C   M   C   L   E   E   E   K   S   A   L   W   Q   D   S   F   Q   P   H   L
 V   A   C   V   L   R   R   K   S   A   V   L   F   G   R   L   F   S   P   H
                          151/51 tga aac atc acc ctc aag aac cag cta atc cca aca tgc ctg ttt tga cat ctg gaa
 *   N   I   T   L   K   N   Q   L   I   P   T   C   L   F   *   H   L   E
 E   T   S   P   S   R   T   S   *   N   P   N   M   P   V   L   T   S   G   T
 K   H   H   P   Q   E   P   A   N   P   S   Q   H   A   C   F   D   I   W   N
                          211/71 cag ggt cgc aag cgc aga agc cac agc atc agg ctc ttg cag ctg gga ctc act
 Q   G   R   K   R   R   S   H   S   I   R   L   L   Q   L   G   L   T
 R   V   A   S   A   Q   K   A   T   A   S   G   S   C   S   W   D   S   L
 G   S   Q   Q   P   A   Q   P   Q   H   Q   A   L   A   A   G   T   H   S
                          271/91 cca gcc ctg tcc cag gat cta tag gag ttg cag gcc gtt ccc agg acg cta tgg tgg
 P   A   L   S   Q   D   L   *   E   L   Q   A   V   P   R   T   L   W   W
 Q   P   C   P   R   I   Y   R   S   C   R   P   F   P   G   R   Y   G   G
 S   P   V   P   G   S   I   G   V   A   A   G   R   S   Q   D   A   M   V   D
                          331/111 act act tct ttc aga ggc agc agc atg gtg agc atg gtc agc tgg agg gag gtg gag gag gag gcg
 T   T   S   F   R   G   S   S   M   V   S   M   V   S   W   R   E   V   E   E   A
 L   L   L   S   E   A   A   A   W   *   A   W   *   A   L   G   E   R   K   R   R   R
 Y   Y   F   Q   R   Q   Q   H   G   E   Q   L   G   L   G   E   S   G   G   G   G   G
                          391/131 gct ata ata gca aac atc gat ggc cta ctg ggg ata aca ttc atg cag aac atc agg
 A   I   I   A   N   I   D   G   L   L   G   I   T   F   M   Q   N   I   R
 L   *   *   Q   T   *   M   A   Y   W   G   *   H   S   C   R   T   S   G
 Y   N   N   S   K   H   R   W   P   T   G   D   N   I   H   A   E   H   Q   V
```

FIG. 18A

```
421/141
tgc gtt cca tgg atg aac tga atc atg att ttc aag cac ttg ctc tgg agg gaa gag cga
 C   V   P   W   M   N   *   I   M   I   F   K   H   L   L   W   R   E   E   R
 A   F   H   G   *   E   L   N   H   D   F   Q   A   L   C   S   G   K   S   D
 R   S   A   L   D   E   *   S   H   *   I   S   T   L   A   L   E   G   R   A   M 481/161
tgg gag agc agc tct tgc cag gta aaa agt ttt ggg aaa cag atg aat cca gca aag atg
 W   E   S   S   S   C   Q   V   K   S   F   G   K   Q   M   N   P   A   K   M
 G   R   A   A   L   A   R   *   K   V   L   G   N   R   *   I   Q   Q   R   W
 E   Q   Q   L   L   P   G   K   K   F   W   E   T   D   E   S   S   K   D   G 541/181
gac caa aag gaa tat tcc tgg gtg atc aat ggc gag aca gtg cct ggg gaa cat cag atc
 D   Q   K   E   Y   S   W   V   I   N   G   E   T   V   P   G   E   H   Q   I
 T   K   R   N   I   P   G   *   S   M   A   R   Q   C   L   G   N   I   R   S
 P   K   G   I   F   L   G   D   Q   W   R   D   S   A   W   G   T   S   D   H 601/201
att cag ttt ccc agc caa tca tgc aga gaa gac ctg gtc aga gtt tcc atg tga aca
 I   Q   F   P   S   Q   S   C   R   E   D   L   V   R   V   S   M   *   T
 F   S   F   P   A   N   H   A   E   K   T   W   S   E   F   P   C   E   Q
 S   V   S   Q   P   I   M   V   Q   R   R   P   G   Q   S   F   H   V   N   S 661/221
gtg agg tca att ctg tac tgt ccc cac gat cgg aga gtg ggg gac tag gcg tta gca tgg
 V   R   S   I   L   Y   C   P   H   D   R   R   V   G   D   *   A   L   A   W
 *   G   Q   F   C   T   V   P   T   I   G   E   W   G   T   S   R   *   H   G
 E   V   N   S   V   L   L   S   P   R   S   E   S   G   R   L   A   I   S   M   V 721/241
tgg agt atg tgt tga gct cat ccc cgg gcg att cct gtc taa gaa aag gag gat ttg gcc
 W   S   M   C   *   A   H   P   R   A   I   P   V   *   E   K   R   G   L   A
 G   V   C   V   E   L   I   P   G   R   L   L   S   K   R   K   E   D   L   P
 E   Y   V   L   S   S   S   P   G   D   S   C   L   R   K   G   G   F   G   P

```
1201/401
att ctc aac aac agc tgt tcc aaa gac cta atg cgc ttg ctg tcc agc agt tga cag ctg
 I   L   N   N   S   C   S   K   D   L   M   R   L   L   S   S   S   *   Q   L
 F   S   Q   Q   L   F   Q   R   P   N   A   L   A   V   Q   P   A   V   D   S   C
     S   Q   Q   L   F   Q   R   P   N   A   L   A   V   Q   P   A   V   L   T   A
                                 1231/411
                                                                           1291/431
1261/421
ctc agc agc agt atg cac tgg cag ctg ctc atc agc cgc aca tcg gtt tag ctc ccg
 L   S   S   S   M   H   W   Q   L   L   I   S   R   T   S   V   *   L   P
 S   A   A   V   C   T   G   S   C   S   S   A   A   H   R   F   L   A   P   R
     Q   Q   Q   Y   A   L   A   A   A   H   Q   P   H   I   G   L   S   P   A
                             1351/451
1321/441
ctg cgt ttg tcc cca atc cat aca tca gcg ctg ctc ccc cag gga cgg acc cct aca
 L   R   L   S   P   I   H   T   S   A   L   L   P   Q   G   R   T   P   T
 C   V   C   P   Q   S   I   H   I   S   A   R   C   S   P   R   G   D   P   L   H
     A   F   V   P   N   P   Y   I   S   A   A   A   L   P   Q   G   T   D   P   Y   T
                     1411/471
1381/461
cag ctg gat tgg ctg cag cag cga cac cag tag gcc cag ctg ctc acc agt att atg
 Q   L   D   W   L   Q   Q   R   H   Q   *   A   Q   L   L   T   S   I   M
 S   W   I   G   C   S   S   D   T   R   R   P   S   C   S   P   V   L   W
 A   G   L   A   A   A   T   L   G   *   A   Q   L   W   S   P   V   Y   G
                                                 1471/491
1441/481
gag tta ctc cct ggg gag tct acc ctg cca gtc ttt tcc agc agc agc ctg ccg
 E   L   L   P   G   E   S   T   L   P   V   F   S   S   S   S   L   P
 S   Y   S   L   G   E   S   L   Y   P   C   Q   S   F   P   A   A   A   C   R
 V   T   P   W   G   E   S   V   Y   P   A   S   F   Q   Q   Q   P   A   A
                                             1531/511
1501/501
ctg cag caa cta att cag cta atc aac aga cca ccc cac ccc acc agg ctc agc agc
 L   Q   Q   L   I   Q   L   I   N   R   P   P   H   P   T   R   L   S   S
 C   S   N   *   F   S   *   S   T   D   H   P   T   P   P   G   S   A   R
 A   A   T   N   S   A   N   Q   Q   T   T   P   Q   A   Q   G   Q   Q
                                 1591/531
1561/521
agg ttc tcc gtg gag gag cca aac gcc gtc ctt tga ccc caa acc ccc aag cca agg gac
 R   F   S   V   E   E   P   N   A   V   L   *   P   Q   T   P   K   P   R   D
 G   S   P   W   R   R   Q   T   P   S   F   D   P   K   P   Q   N   Q   Q   G
 V   L   R   G   A   S   Q   R   P   L   T   P   N   Q   Q   T   R   A   G   T
```

FIG. 18D

```
1621/541
agc aaa cgg atc ccc ttg tgg cag ctg cag cag tga att ctg ccc ttg cat ttg gac aag
 S   K   R   I   P   L   W   Q   L   Q   Q   *   I   L   P   L   H   L   D   K
 A   N   G   S   P   C   G   A   A   S   C   I   F   P   C   I   A   F   G   Q
 Q   T   D   P   L   V   A   A   V   N   S   E   F   C   P   C   I   W   T   R
1681/561                                              1711/571
gtc tgg cag cag gca tgc cag gtt atc cgg tgt ctc ctg ctg ctt act atg acc aaa
 V   W   Q   Q   A   C   Q   V   I   R   C   L   L   L   L   T   M   T   K
 S   G   S   R   H   A   R   L   S   G   V   S   C   C   L   L   *   P   N
 L   A   A   A   G   M   P   G   Y   P   V   L   A   P   A   A   Y   D   Q   T
1741/581                                              1771/591
ctg gtg ccc ttg tag tga atg cag gcg cga gaa agg gtc ttg gag ctc ctg ttc gac ttg
 L   V   P   L   *   *   M   Q   A   R   E   R   V   L   E   L   L   F   D   L
 W   C   P   L   V   E   C   R   R   E   K   W   S   W   S   S   C   *   T   C
 G   A   L   *   S   N   A   G   A   R   N   G   L   G   A   P   V   R   L   V
1801/601                                              1831/611
tag ctc ctg ccc cag tca tta gtt cct cag ctg cac aag cag ctg ttc cag cag ccg
 *   L   L   P   Q   S   L   V   P   Q   L   H   K   Q   L   F   Q   Q   P
 S   S   C   P   S   H   *   F   L   S   C   T   S   S   S   C   S   S   R
 A   P   A   P   V   I   S   S   L   A   A   Q   A   A   V   A   A   A   A
1861/621                                              1891/631
cag ctt cag caa atg gag cag ctg gtc ttg gtg gtc tgg aaa caa atg gac cat ttc gcc
 Q   L   Q   Q   M   E   Q   L   V   L   V   V   W   K   Q   M   D   H   F   A
 S   F   S   K   W   S   S   W   S   W   W   S   G   N   K   W   T   I   S   P
 A   S   A   N   G   A   A   G   L   G   G   L   E   T   N   G   P   F   R   P
1921/641                                              1951/651
ctt tag gaa cac agc agc ctc agc ccc agc agc cca agc agc agc agc cca ata aca acc tgg cat
 L   *   E   H   S   S   L   S   P   S   S   P   S   S   S   P   I   T   T   W   H
 F   R   N   T   A   A   S   A   P   A   A   Q   A   A   A   A   P   *   Q   P   G   I
 L   G   T   Q   Q   P   Q   P   Q   Q   P   S   S   S   S   P   N   N   L   A   S
1981/661                                              2011/671
cca gtt ctt tct acg gca aca act ctc tga aca gca att cac aga gca gct ccc tct tct
 P   V   L   S   T   A   T   T   L   *   T   A   I   H   R   A   A   P   S   S
 Q   F   F   L   R   Q   Q   N   S   E   Q   Q   F   T   E   Q   L   P   L   L
 S   S   F   Y   G   N   N   T   L   N   S   N   S   Q   S   S   L   F   S
```

FIG. 18E

```
2041/681
ccc agg gct ctg ccc agc ctg cca aca cat cct tgg gat tcg gaa gta gca gtt ctc tcg
 P   R   A   L   P   S   L   P   T   H   I   P   W   D   S   E   V   A   V   L   S   R
             2071/691
                                                                                 G
 Q   G   L   C   P   A   Q   N   T   H   L   G   F   G   S   S   K   Q   F   S   L   G
2101/701
gcg cca ccc tgg gat ccg ccc ttg gag ggt ttg gaa cag cag ttg caa act cca aca ctg
 A   P   P   W   D   P   P   L   E   G   L   E   Q   Q   L   Q   T   P   T   L
 R   H   P   G   I   R   R   P   L   W   R   V   W   N   S   C   K   L   Q   H   W
2161/721
 A   T   L   G   S   A   L   G   G   F   G   T   A   V   A   N   S   N   T   G
gca gtg gct ccc gcc gtg act ccc tga ctg gca gca gtg acc ttt ata aga gga cat cga
 A   V   A   P   A   V   T   P   *   L   A   A   V   T   F   I   R   G   H   R
 Q   W   L   P   P   R   *   L   P   D   W   Q   Q   *   P   L   Y   K   E   D   I   E
 S   G   S   R   D   S   L   T   G   S   S   D   L   Y   K   R   T   S   S
2221/741
gca gct tga ccc cca ttg gac aca gtt ttt ata acg gcc tta gct ttc tcc cct ctc ctg
 A   A   *   P   P   L   D   T   V   F   I   T   A   L   A   F   S   P   L   L
 Q   L   D   P   P   H   W   T   Q   F   L   *   R   P   *   L   F   P   P   L   L   W
 S   L   T   P   P   I   G   H   S   F   Y   N   G   L   S   F   S   S   P   G
2281/761
gac ccg tgg gca tgc ctc tcc cta gtc agg gac cag gac att cac aga cac cac ctc ctt
 D   P   W   A   C   L   S   L   V   R   D   Q   D   I   H   R   H   H   L   L
 T   R   G   M   P   L   P   *   S   G   T   R   T   F   T   D   T   T   S   F
 P   V   G   H   A   S   P   S   Q   G   P   G   P   H   S   Q   T   P   P   P   S
2341/781
ccc tct ctt cac atg gat cct ctt caa gct taa acc tgg gag gac tca cga atg gca gtg
 P   S   L   H   M   D   P   L   Q   A   *   T   W   E   D   S   R   M   A   V
 P   L   F   T   W   I   L   F   K   L   K   P   G   R   T   H   E   W   Q   W
 L   S   S   H   G   S   S   S   N   L   N   P   G   G   L   T   N   G   S   G
2401/801
gaa gat aca tct ctt cag gcg ctg aag cca agt acc gca gtg caa gca gcg cct
 E   D   T   S   L   Q   A   L   K   P   S   T   A   V   Q   A   A   P
 R   *   R   L   C   S   R   R   *   S   Q   V   P   Q   C   K   Q   R   L
 K   I   H   L   S   A   A   P   G   A   E   A   K   Y   R   S   A   S   A   S
2431/811
```

FIG. 18F

```
2461/821
cca gcc tct tca gcc cga gca gca ctc ttt tct cct ctc gtt tgc gat atg gaa tgt
 P   A   S   L   Q   P   S   A   R   E   Q   A   H   S   L   F   S   F   L   P   L   S   R   L   V   C   D   M   E   C
                             2491/831
ctg atg tca tgc ctt ctg gca gga gca ggc ttt tgg aag att ttc gaa aca acc ggt acc
 L   M   S   C   L   L   A   G   A   G   F   W   K   I   F   E   T   T   G   T
 *       V       P       R       E       Q       A       F       W       K       I       F       S       K       Q       P       V       P
2521/841
cca att tac aac tgc ggg aga ttg ctg gac ata taa tgg aat ttt ccc aag acc agc atg
 P   I   Y   N   C   G   R   L   L   D   I   *   W   N   F   P   K   T   S   M
         D       V       M       P       S       G       R       S       R       L       E       D       F       F       R       N       N       R       Y       P
2581/861
gga cca gat tca ttc agc tga aac tgg agc tga agc tgg atg tgt ttg gta att acg tca
         Q       F       T       A       G       R       E       I       A       G       H       T       W       E       F       S       Q       D       Q       H       G
2641/881
ggt cca gat tca ttc agc tga aac tgg agc cac cag ctg agc gcc agc ttg tct
 G   P   D   S   F   S   *   N   W   S   V   P   H   Q   L   S   A   S   L   S
     S   R   F   I   Q   L   R   E   I   A   G   H   T   P   A   E   R   Q   L   V   F
2701/901
tca atg aaa tcc tcc agg ctg cca tac ccc acc aac tca tgg tgg atg tgt gta ttt acg tca
 S   M   K   S   S   R   L   P   Y   P   T   N   S   W   W   M   C   V   F   G   N   G   F   L   A   G   R   T   D   S
     Q       *       N       I       L       Q       A       Y       Q       L       P       T       H   G       G       D       V       F       G       N       W       Q       E       L       A       E       R       I       R
2761/921
ttc aga agt tct ttg gca gtc ttg aat ttg gca gtc ttg cat tgg cac tac aga aag ctc
 F   R   S   S   L   A   V   S   L   E   Q   K       T       E       K       L       A       C       Y       I       R       K       S
     S       E       V       L       F       W       Q       S       L       N       L       A       V       L       H       W       H       Y       R       R       L       S       E       A       L       P       C       Y       P       R       V       I       Q       K       A       L
2821/941
gag gcc acg tcc tgt cat tgg cac tac aga tgc atg tac gga
 E   A   T   S   C   H   W   H   Y   R   C   M   Y   G
 R   P   R   P   V   S   L   A   L   Q   M   Y   G   C   R   V   L
2851/951
```

```
3301/1101
tgg aga agt gtg tta ctc acg cct cac gta cgg agc gcg ctg tgc tca tcg atg agg tgt
 W   R   S   V   L   L   T   P   H   V   R   S   A   R   C   S   S   M   R   C
 G   E   K   C   Y   T   H   A   S   R   T   Y   E   R   A   V   L   I   D   V
 E   K   C   V   L   T   P   L   A   H   R   T   E   R   A   V   C   *   H   R   *   E   V   C
3361/1121
gca cca tga acg gtc ccc aca gtc cct tat aca cca tga agg acc agt atg cca
 A   P   *   T   V   P   T   V   P   Y   T   P   *   R   T   S   M   P
 H   H   E   R   S   P   H   S   P   L   H   H   D   E   G   P   V   C   Q
 T   M   N   D   G   P   H   S   A   L   Y   T   M   M   K   D   Q   Y   A   N
3421/1141
act acg tgg tcc aga aga tga ttg acg tgg cgg agc cag gcc agg tcg tca tgc
 T   T   W   S   R   R   *   L   T   W   R   S   Q   A   R   S   S   C
 L   R   G   P   E   D   D   *   R   G   A   E   P   G   Q   V   V   H   A
 Y   V   V   Q   K   M   I   D   V   A   E   P   G   Q   R   A   E   K   I   V   M   H
3481/1161
ata aga tcc ggc ccc aca tcg caa ctc ttc gta agt aca cct atg gca agc gga aga tcg tca tgg
 I   R   S   G   P   T   S   Q   L   F   V   S   T   P   M   A   S   G   R   S   S   W
 *   D   P   A   P   H   I   A   N   S   S   *   V   H   L   W   Q   A   E   V   V   G
 K   I   L   R   P   H   I   R   T   L   R   K   Y   T   Y   G   K   H   I   L   A
3541/1181
cca agc tgg aga agt act aca tga aga acg gtg ttg act tag ggc cca tct gtg gcc ccc
 P   S   W   R   S   T   T   *   R   T   V   L   T   *   G   P   S   V   A   P
 Q   A   G   E   V   L   H   E   E   R   R   C   *   L   R   A   H   L   W   P   P
 K   L   E   K   Y   Y   M   K   N   G   V   D   L   G   P   I   C   G   P   P
3601/1201
cta atg gta tca tct gag gca gtg tca ccc gct gtt ccc tca ttc ccg ctg acc tca ctg
 L   M   V   S   S   E   A   V   S   P   A   V   P   S   F   P   L   T   S   L
 *   W   Y   H   L   R   Q   C   H   P   L   F   P   H   S   R   *   P   A   D   L   T   W
 N   G   I   I   *   G   S   V   T   R   L   C   S   L   I   P   A   D   L   T   G
3661/1221
gcc cac tgg caa atc caa gca acc aga aat gtt cta gtg tag agt ctg aga cgg gca
 A   H   W   Q   I   Q   A   T   R   N   V   L   V   *   S   L   R   R   A
 P   T   L   A   N   P   S   N   Q   Q   P   E   M   F   *   C   R   V   *   C   R   V   E   T   G
 P   L   A   N   P   T   S   N   Q   Q   P   E   K   M   C   S   S   V   E   S   E   T   G   K
```

FIG. 18I

```
3721/1241
agt ggt tgc tcc agg att act ccc tcc aaa aaa gga atc aaa tcc acg agt gga aaa
 S   G   C   S   R   I   T   P   S   K   K   E   I   K   S   T   S   G   K
3751/1251
gcc ttt gta aat tta att tta cac ata aca tgt act att ttt aat tga cta att
 A   F   V   N   L   I   L   H   I   T   C   T   I   F   F   N   *   L   I
3781/1261                                                              3811/1271
     P   L   C   K   F   N   F   I   T   H   N   M   V   Y   F   F   *   L   
3841/1281                                                              
gcc ctg ctg ttt tac tgg tgt ata gga tac ttg tac ata ggt aac caa tgt aca tgg gag
 A   L   L   F   Y   W   C   I   G   Y   L   Y   I   G   N   Q   C   T   W   E
     P   C   C   F   T   G   V   *   D   T   C   T   *   V   T   N   V   H   G   R
         A   V   L   L   V   Y   R   I   L   V   H   R   *   P   M   Y   M   G
3901/1311
gcc aca tat ttt gtt cac tgt tgt atc tat att tca cat gtg gaa act ttc agg gtg gtt
 A   T   Y   F   V   H   C   C   I   Y   I   S   H   V   E   T   F   R   V   V
     P   H   I   F   V   F   T   V   L   Y   L   F   H   M   W   K   L   S   G   W   L
         H   I   F   C   S   L   L   Y   L   Y   I   F   T   C   G   N   F   Q   G   G
3961/1321                                                              3991/1331
ggt tta aca aaa aaa agc ttt aaa aaa aga aaa gga aaa ggg aaa ggt ttt tag ctc
 G   L   T   K   K   S   F   K   K   R   K   G   K   G   K   G   F   *   L
     V   *   Q   K   K   A   L   *   K   E   K   E   K   R   K   R   F   L   A   H
         F   N   K   K   K   L   *   K   K   K   K   K   K   K   R   F   L   V   S   
4021/1341                                                              
att tgc ctg gcc ggc aag ttt tgc aaa tag ctc ccc acc tcc tca ttt tag taa aaa
 I   C   L   A   G   K   F   C   K   *   L   P   T   S   S   F   *   *   K
     F   A   W   P   A   S   F   A   N   S   S   P   P   H   L   L   V   K   K
         L   P   G   R   Q   V   L   Q   I   A   L   P   H   L   *   L   V   K   N
4081/1361                                                              4111/1371
aca aac aaa aac aaa aca aaa acc tga gaa gtt tga att gta gtt aaa tga ccc caa act ggc
 T   N   K   N   K   T   K   T   *   E   V   *   I   V   V   K   *   P   Q   T   G
     Q   T   K   Q   T   K   Q   N   L   R   S   L   N   C   S   *   M   T   P   K   L   A
         K   Q   K   T   K   P   E   K   F   E   L   *   L   N   D   P   K   N   W   H

FIG. 18J
```

```
4141/1381
att taa cac tgt tta taa aaa ata tat ata tat aat gaa aaa ggt ttc
 I  *  H  C  L  *  K  I  Y  I  Y  I  N  E  K  G  F
   F  N  T  V  F  I  K  N  I  Y  I  Y  I  M  K  V  S
     L  T  L  F  *  K  Y  K  Y  Y  *  K  R  F  Q

4171/1391

4201/1401
aga gtt gct aaa gct tca gtt tgt gac att aag ttt atg aaa ttc taa aaa atg cct ttt
 R  V  A  K  A  S  V  C  D  I  K  F  M  K  F  *  K  M  P  F
   E  L  *  K  L  Q  F  V  *  H  *  V  Y  E  I  L  K  N  A  F  F
     S  C  *  S  F  S  L  *  Y  *  V  Y  E  I  L  K  N  A  F  F 4261/1421
ttg gag act ata tta tgc tga aga agg ctg ttc gtg agg aga tgc gag cac cca gaa
 L  E  T  I  L  C  *  R  R  L  F  V  R  R  C  E  H  P  E
   W  R  L  Y  Y  A  E  E  G  C  S  *  G  G  D  A  S  T  Q  R  T
     G  D  Y  I  M  L  K  K  A  V  R  E  E  E  M  R  A  P  R 4321/1441
cgt ctt ttg agg ctg ggc ggg tgt gat tgt tta ctg cct act gga ttt ttt tct att aac
 R  L  L  R  L  G  G  C  D  C  L  L  P  T  G  F  F  S  I  N
   V  F  *  G  W  A  G  V  *  L  V  C  L  L  D  F  F  L  L  T
     S  F  E  A  G  R  V  L  F  T  A  Y  W  I  F  F  Y  *  H 4381/1461
att gaa agg taa aat ctg att att tag cat gag aaa aat cca act ctg ctt ttg gtc
 I  E  R  *  N  L  I  I  *  H  E  K  N  P  T  L  L  L  V
   L  K  G  K  I  *  L  F  S  M  R  K  K  I  Q  L  C  F  W  S
     *  K  V  K  Y  L  *  D  Y  L  A  *  E  K  K  S  N  S  A  F  G  L 4441/1481
ttg ctt cta taa ata tat agt gta tac ttg gtg tag act ttg cat ata tac aaa ttt gta
 L  L  L  *  I  Y  S  V  Y  L  V  *  T  L  H  I  Y  K  F  V
   C  F  Y  K  Y  I  V  C  T  W  C  R  L  C  I  Y  T  N  L  *
     A  S  I  N  I  *  C  V  L  G  V  D  F  A  Y  I  Q  I  C  S 4501/1501
gta ttt tct tgt ttt gat gtc taa tct gta tct ata atg tac cct agt agt cga aca tac
 V  F  S  C  F  D  V  *  S  V  S  I  M  Y  P  S  S  R  T  Y
   Y  F  L  V  L  M  S  N  L  Y  L  *  C  T  L  V  V  E  H  T
     I  F  L  F  *  C  L  I  C  I  Y  N  V  P  *  *  S  N  I  L

```
4981/1661
aca atc aga gcc cct ctc acc ttg taa agt gtg aat cgc cct tcc ctt ttg tac aga aga
 T   I   R   A   P   L   T   L   *   S   V   N   R   P   S   L   L   Y   R   R
 Q   S   E   P   L   S   P   C   K   V   C   *   I   A   L   P   F   C   T   E   D
   N   Q   S   P   S   H   L   V   K   S   P   F   F   V   Q   K   M
                                5011/1671
5041/1681
tga act gta ttt tgc att ttg tct act tgt aag tga atg taa cat act gtc aat ttt cct
 *   T   V   F   C   I   L   S   T   C   K   *   M   *   H   T   V   N   F   P
 E   L   Y   F   A   F   C   V   L   V   *   S   E   C   N   I   L   S   I   F   L
   N   C   I   L   H   F   L   *   L   V   N   V   T   Y   C   Q   F   S   L
                                5071/1691
5101/1701
tgt ttg aat ata gaa ttg taa cac tac acg gtg tac att tcc aga gcc ttg tgt ata ttt
 C   L   N   I   E   L   *   H   Y   T   V   Y   I   S   R   A   L   C   I   F
 V   *   I   *   N   C   N   T   L   H   G   V   H   F   Q   S   L   V   Y   F   S
   F   E   Y   R   I   V   T   T   R   C   T   F   P   E   P   C   V   Y   I
                                5131/1711
5161/1721
cca atg aac ttt ttt gca agc aca ctt gta acc ata tgt gta taa tta aca aac ctg tgt
 P   M   N   F   F   A   S   T   L   V   T   I   C   V   *   L   T   N   L   C
 Q   *   T   F   L   Q   A   H   T   C   N   H   M   C   I   I   N   K   P   V   Y
   N   E   L   F   C   K   H   T   L   V   *   Y   V   Y   N   *   Q   T   C   V
                                5191/1731
5221/1741
atg ctt atg cct ggg caa cta ttt gta act ctt gtg tag att gtc tct aaa caa tgt
 M   L   M   P   G   Q   L   F   V   T   L   V   *   I   V   S   K   Q   C
 C   L   C   L   G   N   Y   L   *   L   L   C   R   L   S   L   *   N   N   V
   A   Y   A   W   A   T   I   F   C   N   S   C   V   D   C   L   *   T   M   C
                                5251/1751
5281/1761
gtg atc ttt att ttg aaa aat aca gaa ctt tgg aat ctg
 V   I   F   I   L   K   N   T   E   L   W   N   L
 *   S   L   F   *   K   I   Q   N   F   G   I
   D   L   Y   F   E   K   Y   R   T   L   E   S
                                5311/1771

FIG. 18M
```

```
1/1
GGA AGT TAA AGG GAA AAA GCA ATT CAC AGG AAA GAG TAC AAA GAC AGC ACA AGA AAA AAA
 G   S   *   R   E   K   A   I   H   R   K   E   Y   K   D   S   T   R   K   K
 E   V   K   G   K   S   N   S   Q   E   S   T   Q   H   A   Q   E   K   N   T
                                  31/11
61/21
CAG ATT TCA TAA AAA TAG TGA TTC TGG TTC AAA GAC ATT TCC AAC AAG GAA AGT TGC AAA
 Q   I   S   *   K   *   *   F   W   F   K   D   I   S   N   K   E   S   C   K
 R   F   H   K   N   S   D   S   G   S   K   T   F   P   T   R   K   V   L   L
         91/31
121/41
TAA AGA AGG TGG ACC TAA AGT CAC ATC TAG GAA CTT TGA GAA AAG TAT CAC AAA ACT TGG
 *   R   R   W   T   *   S   H   I   *   E   L   *   E   K   Y   H   K   T   W
 K   E   G   G   D   L   K   V   S   R   N   F   R   K   S   I   T   K   L   G
                          151/51               211/71
181/61
GAA AAA GGG TGT AAA GCA GTT CAA GAA TAA GCA AGG GGA CAA ATC ACC AAA GAA CAA CAA
 E   K   G   C   K   A   V   Q   E   *   A   R   G   Q   I   T   K   E   Q   Q
 K   K   G   V   *   S   S   K   N   K   Q   G   D   K   S   P   K   N   K   N
                                        271/91
241/81
ATT CCA GCC GGC AAA TAA ATT CAA GAG AAA ATT CCA GCC AGA TGG TAG AAG CGA
 I   P   A   G   K   *   I   Q   E   K   I   P   A   R   W   *   K   R
 F   Q   S   R   Q   I   N   S   R   E   F   Q   P   D   G   R   S   D
```

FIG. 19A

301/101
TGA ATC AGC AGC CAA GAA GCC CAA ATG GGA TGA CTT CAA AAA GAA GAA AGA ACT GAA
 *   I   S   S   Q   E   A   Q   M   G   *   L   Q   K   E   E   R   T   E
 N   Q   Q   R   S   P   R   P   N   G   D   F   K   K   R   K   N   *   K   S
                                        331/111

361/121
GCA AAG CAG ACA ACT CAG TGA CAT TGT TCG GGC AAA GCA GAT
 A   K   Q   T   T   Q   *   H   C   S   G   K   A   D
 Q   R   Q   L   N   Q   L   I   V   R   A   K   Q   -M
 K   A   D   N   S   *   M   T   L   F   G   Q   S   R   C
                        391/131

421/141
GTG GGA GAT TTT AAG AAG AAA AGA CTG TGA CAA AGA AAA AAG AGT AAA GTT AAT GAG TGA
 V   G   D   F   K   K   K   R   L   *   Q   R   K   K   S   K   V   N   E   *
 W   E   I   L   R   R   K   D   C   *   T   E   K   R   V   K   L   M   S   D
 G   R   F   *   E   E   K   T   V   T   K   K   K   E   *   K   S   *   V   I
                                        451/151

481/161
TTT GCA GAA GTT GAT TCA AGG GAA AAT TAA AAC TAT TGC ATT TGC ACA CGA TTC AAC TCG
 F   A   E   V   D   S   R   E   N   *   N   Y   C   I   C   T   R   F   N   S
 L   Q   K   L   I   Q   G   K   I   K   T   I   A   F   A   H   D   S   T   R
 C   R   S   *   F   K   G   K   L   K   N   Y   C   I   C   T   R   F   N   S   V
                                        511/171
                                        N   Y   C   I   A   F   A   H   L   H   T   I   Q   L   V

FIG. 19B

```
541/181
TGT GAT CCA GTG TTA CAT TCA GTA TGG TAA TGA AGA ACA GAG AAA ACA GGC TTT TGA AGA
 C   D   P   V   L   H   S   V   W   *   R   T   E   K   T   G   F   *   R
 V   I   Q   C   Y   I   Q   Y   G   N   E   Q   R   K   Q   R   A   F   E   E
 *   S   S   V   T   F   S   M   V   *   K   N   R   E   N   R   L   L   K   N
                                571/191
601/201
ATT GCG AGA TGA TTT GGT TGA GTT AAG TAA ACC ACA GAT AAT CAG AAG TTT TAA AGG CCA
 I   A   R   *   F   G   *   V   K   *   T   T   D   N   Q   K   F   *   R   P
 L   R   D   D   L   V   E   L   S   K   P   Q   R   I   A   R   F   L   R   G   H
 C   E   M   I   W   L   S   *   V   K   N   H   R   *   S   E   V   L   K   A   T
                                631/211
ATT TCT CAT GTA TGG AAG TAA ACC ACA GAT TGC AGA GAT AAT CAG AAG TTT TAA AGG CCA
 I   S   H   V   W   K   *   T   T   D   C   R   D   N   Q   K   F   *   R   P
                                691/231
CGT GAG GAA GAT GCT GCG GCA TGC GGA AGC ATC AGC CAT CGT GGA GTA CGC ATA CAA TGA
 R   E   E   D   A   A   A   C   G   S   I   S   H   R   G   V   R   I   Q   *
 V   *   R   K   M   L   R   H   A   E   A   S   A   I   V   E   Y   A   Y   N   D
 *   G   R   C   C   G   M   R   K   H   Q   P   S   W   S   T   H   T   M   T
                                751/251
```

FIG. 19C

```
781/261
CAA AGC CAT TTT GGA GCA GAG GAA CAT GCT GGA AGA GCT CTA TGG GAA CAC ATT TCA
 Q   S   H   F   G   A   E   E   H   A   G   R   A   L   W   E   H   I   S
 K   A   I   F   W   S   R   N   M   L   A   D   G   E   L   Y   G   N   T   F   Q
                                                 811/271
                     K   R   *   C   T   R   K   T   E   K   S   M   G   T   H   F   S

841/281
GCT TTA CAA GTC AGC AGA TCA CCG AAC TCT GGA CAA AGT GTT AGA GGT ACA GCC AGA AAA
 A   L   Q   V   S   R   S   P   N   S   G   Q   S   V   R   G   T   A   R   K
 L   Y   K   S   A   D   H   R   T   L   D   K   S   L   E   V   Q   P   E   K
                                             871/291
 F   T   *   Q   Q   I   T   E   L   W   *   T   K   C   *   R   Y   S   Q   K   N

901/301
ATT AGA ACT TAT TAT GGA TGA AAT GAA ACA GAT TCT AAC TCC AAT GGC CCA AAA GGA AGC
 I   R   T   Y   Y   G   *   N   E   T   D   S   N   S   N   G   P   K   G   S
 L   E   L   I   L   W   M   K   *   N   R   F   *   L   Q   W   A   Q   K   E   A
                                             931/311
 *   N   Y   I   M   D   E   K   R   L   I   L   T   P   M   H   P   K   R   K   L

961/321
TGT GAT TAA GCA CTC ATT GGT GCA TAA AGT ATT CTT GGA CTT TTT TAC CTA TGC ACC CCC
 C   D   *   A   L   I   G   A   *   S   I   L   G   L   F   Y   L   C   T   P
 V   I   K   H   S   L   V   H   K   V   F   L   D   F   F   T   Y   A   P   P
                                             991/331
 *   L   S   T   H   W   C   I   K   Y   S   W   I   F   L   P   M   H   T   P

1021/341
CAA ACT CAG ATC AGA AAT GAT TGA AGC CAT CCG CGA AGC GGT CTA CCT GGC ACA CAC
 Q   T   Q   I   R   N   D   *   S   H   P   R   S   G   L   P   G   T   H
 K   L   R   S   E   M   I   E   A   I   R   E   A   V   Y   L   A   H   T
                                     1051/351
 N   S   D   Q   K   *   L   K   P   S   A   K   R   W   S   T   W   H   T   H
```

FIG. 19D

```
1081/361
ACA CGA TGG CGC CAG AGT GGC CAT GCA CTG GCA TGG CAC GCC CAA GGA CAG GAA
 T   R   W   R   Q   S   G   H   A   L   A   W   H   A   Q   G   Q   E
 H   D   G   A   R   V   A   M   H   C   G   M   T   P   K   D   R   K
 T   M   A   P   E   W   P   C   T   A   W   H   A   R   P   R   T   G   K

1111/371
1141/381
AGT GAT TGT GAA AAC AAT GAA GAC TTA TGT AAA GGT GGC TAA TGG CCA ATA CTC CCA
 S   D   C   E   N   N   E   D   L   C   K   G   G   *   W   P   I   L   P
 V   I   V   K   T   M   K   T   Y   V   K   V   A   N   G   Q   Y   S   H
 *   L   *   R   E   *   R   R   L   M   *   R   W   L   M   A   N   T   P   I

1201/401
TTT GGT TTT ACT GGC GGC ATT TGA TAT TGA TAC TAA GCT TGT GAA GCA GAT AAT
 F   G   F   T   G   G   I   *   Y   *   Y   *   A   C   E   A   D   N
 L   V   F   L   A   A   F   D   I   D   T   K   L   V   K   Q   I
 W   F   Y   W   R   R   H   L   I   L   *   L   S   L   *   S   R   *   I

1231/411
1261/421
CAT ATC AGA AAT TAT CAG TTC ATT GCC TAG CAT AGT AAA TGA CAA ATA TGG AAG GAA GGT
 H   I   R   N   Y   Q   F   I   A   *   H   S   K   *   Q   I   W   K   E   G
 I   S   E   I   I   S   L   L   P   S   I   V   N   D   K   Y   G   R   K   V
 Y   Q   K   L   S   V   H   C   L   A   *   *   M   T   N   M   E   G   R   S

1291/431
1321/441
CCT ATT GTA CTT ACT AAG CCC CAG AGA TCC TGC ACA TAC AGT ACG AGA AAT CAT TGA AGT
 P   I   V   L   T   K   P   Q   R   S   C   T   Y   S   T   R   N   H   *   S
 L   L   *   L   L   R   P   R   D   P   A   H   T   V   R   E   I   I   E   V
 Y   C   T   Y   *   A   P   E   I   L   H   I   Q   Y   E   K   S   L   K   F

```
1381/461
TCT GCA AAA AGG AGA TGG AAA TGC ACA CAG TAC AGA GGT CCG CAG ACG GGA
 S   A   K   R   R   W   K   C   T   Q   Y   R   G   P   Q   T   G
 L   Q   K   G   D   G   N   A   H   T   E   V   R   S   A   D   E
 C   K   E   E   M   E   M   H   T   *   R   *   P   R   *   R   S
1411/471
1441/481
GCT CCT AGA ATC CAT TTC TCC AGC TTT GTT AAG CTA CCT GCA AGA ACA CGC CCA AGA AGT
 A   P   R   I   H   F   S   S   F   V   K   L   P   A   R   T   R   P   R   S
 L   L   E   S   I   S   P   A   L   C   *   V   Y   L   Q   E   H   A   Q   E   V
 S   *   N   P   F   L   Q   L   C       A   T   C   K   N   T   P   K   K   W
1471/491
1501/501
GGT GCT AGA TAA GTC TGC GTG TGT GTT GGT GTC TGA CAT TCT GGG ATC TGC CAC TGG AGA
 G   A   R   *   V   C   V   C   V   G   V   *   H   S   G   I   C   H   W   R
 V   L   D   K   S   A   C   V   C   W   C   L   T   F   W   D   L   P   L   E   T
 C   *   I   S   L   R   V   C   V   L   G   V   S   D   I   L   G   S   A   T   G   D
1561/521
1591/531
CGT TCA GCC TAC CAT GAA TGC CAT CGC CAG CTT GGC AGC AAC AGG ACT GCA TCC TGG TGG
 R   S   A   Y   H   E   C   H   R   Q   L   G   S   N   R   T   A   S   W   W
 V   Q   P   T   M   N   A   I   A   S   L   A   A   T   G   L   H   P   G   G
 F   S   L   P   *   M   P   S   P   A   W   Q   Q   Q   D   C   I   L   V   A
```

FIG. 19F

```
1621/541
CAA GGA CGG AGA GCT TCA CAT TGC AGA ACA TCC TGC AGG ACA TCT AGT TCT GAA GTG GTT
 Q   G   R   R   A   S   H   C   R   T   S   C   R   T   S   S   S   E   V   V
 K   D   G   E   L   H   I   A   E   H   P   A   G   H   L   *   L   K   W   L
 R   T   E   S   F   T   L   Q   N   I   L   Q   D   I   *   V   F   S   G   *
1681/561
AAT AGA GCA AGA TAA AAA GAT GAA AGA AAA AGG TTG TTT TGC AAA AAC ACT
 N   R   A   R   *   K   D   E   R   K   R   L   F   C   K   N   T
 I   E   Q   D   K   K   M   K   E   K   G   C   F   A   K   T   L
 *   S   K   I   K   R   *   R   K   K   E   V   L   Q   K   H   L
1741/581
TGT AGA GCA TGT TGG TAT GAA CCT GAA GAA CCT GAA CCT CTG GGC TAG TGT AAA TCG AGG TGC CAT
 C   R   A   C   W   Y   E   P   E   E   P   E   P   L   G   *   C   K   S   R   C   H
 V   E   H   V   G   M   *   E   P   E   P   N   L   W   A   S   V   N   R   G   A   I
 *   S   M   L   V   *   R   T   *   E   P   E   P   *   S   V   *   I   E   V   P   L
1801/601
TAT TCT TTC TAG CCT CCT CCA GAG TTG TGA CCT GGA AGT TGC AAA CAA AGT CAA AGC TGC
 Y   S   F   *   P   P   P   E   L   *   P   G   S   C   K   Q   S   Q   S   C
 I   L   S   L   A   S   R   V   C   D   L   E   V   A   N   K   V   K   A   A
 F   F   L   *   P   P   Q   S   L   *   T   W   K   L   Q   T   K   S   K   L
1861/621
ACT GAA AAG CTT GAT TCC TAC ACT GGA AAA CAA AAG CAC CAG CAA AGG AAT AGA AAT
 T   E   K   L   D   S   Y   T   G   K   Q   K   H   Q   Q   R   N   R   N
 L   K   S   L   I   P   T   L   E   K   T   K   T   S   K   G   I   E   I
 *   K   A   *   F   L   H   W   K   P   K   A   P   A   K   E   *   K   F
```

FIG. 19G

```
1921/641
TCT ACT TGA AAA ACT GAG CAC ATA GGT GGA AAG AGT TAA GAG CAA GAT GGA ATG ATT TTT
 S   T   *   K   T   E   H   I   G   G   K   S   *   E   Q   D   G   M   I   F
 L   L   E   K   N   *   L   *   K   R   V   K   R   A   S   K   M   E   *   F
 Y   L   K   N   T   S   A   H   R   W   K   E   L   R   A   R   W   N   D   F
                            1951/651
1981/661
TCT GTT CTC TGT TCT GTT TCC CAA TGC AGA AAA GGG GTA GGG TCC ACC ATA CTG GTA
 S   V   L   C   S   V   F   P   M   R   K   G   V   G   S   T   I   L   V
 L   F   S   V   L   F   C   F   P   N   A   E   K   K   G   P   P   Y   W   *
 C   S   L   F   C   Y   S   L   C   E   K   R   R   G   R   V   H   T   G
                                  2011/671
2041/681
ATT GGG GTA CTC TGT ATA TGT GTT TCT TCT TTG TAT ACG AAT CTA TTT ATA TAA ATT GTT
 I   G   V   L   C   I   C   V   S   S   L   Y   T   N   L   F   I   *   I   V
 L   G   Y   S   V   Y   V   F   L   L   C   I   R   I   Y   L   Y   K   L   F
 W   G   T   L   C   M   C   F   F   F   V   Y   E   S   I   Y   I   N   C   F
                                        2071/691
2101/701
TTT TTA AAT GGT
 F   L   N   G
 F   *   M
 F   K   W
```

```
1305 GAT GAA GAC ACT TAT TAT CAA TGG CAG GGT AAA AAG ACT TCT GCT CAG TAC TAT ATT AAC AAC GCC GGT GTA TCT 1379
 221  D   E   D   T   Y   Y   Q   W   Q   G   K   K   T   S   A   Q   Y   Y   I   N   N   A   G   V   S  245

1380 GCA GAA GAT GGG TGC ATT ACA GAA GAT GTC GGT ACT TCG GAT GTC GGC AAC TGG GCT CCA CTA GTG GGT GCT GGT 1454
 246  A   E   D   G   C   I   T   E   D   V   G   T   S   D   V   G   N   W   A   P   L   V   G   A   G  270

1455 TCC ACT AAT GGA TCC GAT GCA GTT TGC ATT TTG TCG AAC GTT GCT CAA AAC AGT AGT GCC AAC TTT TTC ACC GGA GAT GGT TCC 1529
 271  S   T   N   G   S   D   A   V   C   I   L   S   N   V   A   Q   N   S   A   N   F   F   T   G   D   G   S  295

1530 ATA GTT GCA TCC ACA GTT TCT GTT TTA TCT CAG GGC TAT GCG GAA TTT GTT TAT TAA GTCACTCTCTTTTCGGTAAAAGA ATG 1604
 296  I   V   A   S   T   V   S   V   L   S   Q   G   Y   A   E   F   V   Y   *                                M  320

1605 GAT GGT TGC ACA GTT TCT CCC ATT CTT TTT CTT CCG CTC ATT TAT TAT ACA TTG GGA 1685
 321  D   G   C   T   V   S   P   I   L   F   L   P   L   I   Y   Y   T   L   G    1

1686 TCT TGT ATT TTG ATA ATT TTT CTC CAT TCA ACT TCT TAA AAAGTTTCGTTGATCGCTATT ATG CTA TGG ATT CAA 1760
   2  S   C   I   L   I   I   F   L   H   S   T   S   *                            M   L   W   I   Q  26

1761 TTC CGT TAT ATT TTT CTC CTC CTT CAA GTT GTA CTC CCG CTC TTT AGT TCG TTT ATT TTT TTG TTA 1838
  27  F   R   Y   I   F   L   L   L   Q   V   V   L   P   L   F   S   S   F   I   F   L   L    5

1839 AGA TTT TCT TTT TGT TTG TAT ACA TAT ATA TAG TGTTTATTTGTTACTTCCTGCCAGTTGCAACAGAACTA 1913
   6  R   F   S   F   C   L   Y   T   Y   I   *                                             30

1914 ACA AGG TGT TTG TAT ACA TAT TAA ATAT GAA ATA TTA TAG TATAAA AAT AAC AGT ATC CTA GTC CTT GTG TTC GGC TTT 1998
  31  T   R   C   L   Y   T   Y   I   *    M   E   I   L   *                                                  5

1999 ACAAG ATG CCA TGC TGT TTT TTT TCA TTT TTT GGC TAT AAA AAT AAC AGT ATC CTA GTC CTT GTG TTC GGC TTT 2072
   1        M   P   C   C   F   F   S   F   F   G   Y   K   N   N   S   I   L   V   F   G   T         23

2073 AAA ATG GAA TTG CAA ACC CCA TAA TTCCTTCTTCACACCGAACAAACCGCCTAGTAGTCGATTTCAGAGACTCTA ATG CTT TGA ATA 2160
  24  K   M   E   L   Q   T   P   *                                                        M   L   *     3

2161 TAATTTTTTTCTTCAAAAATTCCTTAAGCGTGCTATCGA ATG AGT AGA CAT CAA AGT CCA CTT TTT ACA TAT ACA CGA CAA 2245
   1                                            M   S   R   H   Q   S   R   V   P   L   F   T   Y   T   R   R   Q  15

2246 CGC TGC TTC TAA TATTTTGGAGTGTAGCATAGCCCAATCAATCAAATCTTCGATA ATG GTC ATG TAA GTC ATG GGG GCT AAC GAA ATC AAT GCA 2331
  16  R   C   F   *                                                M   V   M   *   V   M   L   G   A   N   E   I   N   A  10

2332 CCC ACA GTA ACA CTC ATG ACT ATG ACT CTT AAT TTC ACA GTA CTT AAT GTC ATG TAA GTC ATG GGG GCT AAC GAA ATC AAT GCA 2406
  11  P   T   V   T   L   M   T   M   T   L   K   F   S   V   L   N   V   M   *                                      35

2407 ATG GGC GTT TCT CTA TAA ACG ATA TGC GTA TTG TTC ACC ACT GGA TCC 2457
  36  M   G   V   S   L   *                                                 10
```

```
                1                                                                         50
Pile.1 (Nca3)   ..........  MCFLLETSAS  PRSKLSKDFK  PQFTLLSSVT  ..........
Pile.1 (Uth1)   ..........  ..........  ..........  KKKKKKKVRPH  NFQCIHSLNF
Pile.1 (Sag1)   ..........  ..........  ..........  ..........  ..........
Consensus       ----------  ----------  ----------  ----------  ----------

51                                                                        100
Pile.1 (Nca3)   VYFLFIHSFL  FEYNQLLVLP  LNKNLPSLNF  ..........  ..........
Pile.1 (Uth1)   ..........  ..........  SRNSSMKLSA  ....MKISA   ALILSSLSSV
Pile.1 (Sag1)   ..........  ..........  ..........  ....MKFST   AVT.TLISSG
Consensus       ----------  ----------  ----------  ---MK-S---  ----------

101                                                                       150
Pile.1 (Nca3)   AFSAPAPAPA  DSHHEDHHKD  EKPAV.....V  TVTQYID...  ..........
Pile.1 (Uth1)   ASTAVLAAPA  VHHSDNHHHN  DKRAV.....V  TVTQYVNADG  AVVIPAA...
Pile.1 (Sag1)   AIVSALPHVD  VHQEDAHQH.  .KRAVAYKYV   YETVVVDSDG  HTVTPAASEV
Consensus       A---------  -------H--  -K-AV-----V  --T-------  ----------

151                                                                       200
Pile.1 (Nca3)   ..........  ..........  ....SN      AATSTVES.A  ATTTTL....
Pile.1 (Uth1)   ..........  TTATSA      AADGKVESVA  AATTTLSSTA  AAATTSAAAS
Pile.1 (Sag1)   ATAATSAIIT  TSVLAPTSSA  AAADSSASIA  VSSAALAKNE  KISDAAASAT
Consensus       ----------  ------S--   AA------S-A  -------L--  ----------

201                                                                       250
Pile.1 (Nca3)   ...SSSEKD   TSEQKRDGGF  QDGTVKC...  ..........  ..........
Pile.1 (Uth1)   SSSSSSSSS   SSSSVGSGDF  EDGTISC...  ..........  ..........
Pile.1 (Sag1)   ASTSQGASSS  SSSSSATSTL  ESSSVSSSSE  EAAPTSTVVS  TSSATQSSAS
Consensus       ---------S  ----------  ----------  ----------  ----------
```

FIG. 22A

```
                    251                                                                                    300
Pile.1 (Nca3)       ..........  ..........  .SDFPSV    NGIVSLDWLG  FGGWASVMDM  DANTSSECKD
Pile.1 (Uth1)       ..........  ..........  .SDFPSG    QGAVSLDWLG  LGGWASIMDM  NGNTATSCQD
Pile.1 (Sag1)       SATKSSTSST  SPSTSTSTST             SSTSSSSSSS  SSSSSSSNT   DTSTGGSCKE
Consensus           ----------  ----------  ---S---    ------S---  ----------  ---T---C--

301                                                                                    350
Pile.1 (Nca3)       GYYCSYACEP  GMSKTQWPSD  QPSDGKSVGG  LYCKNGYLYR  TNTDTSDLCS
Pile.1 (Uth1)       GYYCSYACSP  GYAKTQWPSE  QPSDGRSVGG  LYCKNGKLYR  SNTDTNSLCV
Pile.1 (Sag1)       GSYCSYSCQP  GMSKTQWPSD  QPSDGRSVGG  LLCKNGYLYR  SNTDADYCLE
Consensus           G-YCSY-C-P  G--KTQWPS-  QPSDG-SVGG  L-CKNG-LYR  -NTD---LC- 351                                                                                    400
Pile.1 (Nca3)       TDETSAKAIN  KKSDSIALCR  TDYPGSENMV  IPTVVDGGDS  QPISVVDEDT
Pile.1 (Uth1)       EGOGSAOAVN  KVSGSIAICG  TDYPGSENMV  VPTVVGAGSS  QPINVIKEDS
Pile.1 (Sag1)       WGVEAAYVVS  KLSKGVAICR  TDYPGTENMV  IPTYVEGGSS  LPLTVVDODT
Consensus           ------A---  K-S---A-C-  TDYPG--ENMV  -PT-V--G-S  -P--V---D-

401                                                                                    450
Pile.1 (Nca3)       YYQWQGKKTS  AQYYINNAGV  SAEDGCIWGT  SGSDVGNWAP  LVLGAGSTNG
Pile.1 (Uth1)       YYQWQGKKTS  AQYYVNNAGV  SVEDGCIWGT  EGSGVGNWAP  VVLGAGYTDG
Pile.1 (Sag1)       YFTWEGKKTS  AQYYVNNPGV  SVEDGCIWGT  SGSGIGNWAP  LNFGAASTGG
Consensus           Y--W-GKKTS  AQYY-NN-GV  S-EDGCIWGT  -GS--GNWAP  ---GA--T-G
```

FIG. 22B

```
              451
Pile.1 (Nca3)  ETYLSLIPNP  NSNQAANFNV  KIVASDG.AN  VQGSCAYEDG  SFTGDGSDGC
Pile.1 (Uth1)  ITYLSIIPNP  NNKEAPNFNI  KIVATDG.ST  VNGACSYENG  VYSGGSDGC
Pile.1 (Sag1)  VTYLSLIPNP  NNSDALNYNV  KIVAADDSSN  VIGECVYENG  EFSG.GADGC
Consensus      -TYLS-IPNP  N---A-N-N-  KIVA-D----  V-G-C-YE-G  ---G-G-DGC
Sun4           ....SLIPNP  NNGNALNFNV  KIVAADDSST  VNGECIYENG  SFSSGGSDGC 501              515
Pile.1 (Nca3)  TVSVLSGSAE  FVFYZ
Pile.1 (Uth1)  TVSVTSGSAN  FVFYZ
Pile.1 (Sag1)  TVSVTSGKAH  FVLYN
Consensus      TVSV-SG-A-  FV-Y-
Sun4           TVSVTAGKAK  FVLY.
```

FIG. 22C

EIGHT REPEATS IN UTH4
```
193    LatDqFGcrFLQKkLE
231    LilDpFGnyLVdKicD
267    IsinqYGtrsLQKiID
310    LinDInGnhVIQKcIf
348    IstHkhGccVLQKiLs
384    LinDqFGnyIIQfiLD
422    LsclkFssnVVeKfIK
487    LirDnFGnyALQtlLD
```
 HYDROPHOBIC    CHARGED
FIG. 23

| | | |
|---|---|---|
| UTH4 | L a t D q F G C R F L Q K k L E | |
| YGLO23 | L c k D q H G C R F L Q K q L D | 1 |
| PUMILIO | F s q D q H G S R F I Q Q k L E | |
| HUMAN | F s q D q H G S R F I Q L k L E | |
| | L i l D p F G N Y L I Q K i C D | |
| | L m t D s F G N Y L I Q K l L E | 2 |
| | L m t D v F G N Y V I Q K f F E | |
| | L m r D v F G N Y V I Q K f F E | |
| | I s i N q Y G T R S L Q K i I D | |
| | I s l N p H G T R A L Q K l I E | 3 |
| | L a l Q m Y G L R V I Q K a L E | |
| | L a l Q m Y G L R V I Q K a L E | |
| | L i n D l N G N H V I Q K c I F | |
| | L s k D l N G N H V I Q K c L Q | 4 |
| | C v k D q N G N H V V Q K c I E | |
| | C v k D q N G N H V V Q K c I E | |
| | I s t H k H G C C V L Q K l L S | |
| | I a t H r H G C C V L Q R c L D | 5 |
| | L s t H p Y G C R V I Q R i L E | |
| | L s t H p Y G C R V I Q R i L E | |
| | L i n D q F G N Y I I Q F l L D | |
| | L t l D p F G N Y V V Q Y i I T | 6 |
| | L i q D q Y G N Y V I Q H v L E | |
| | L v q D q Y G N Y V I Q H v L E | |
| | L s c I k F S S N V V E K f I K | |
| | L s i H k F G S N V I E K i I K | 7 |
| | L s q H k F A S N V V E K c V T | |
| | V l s Q h F A S N V V E K c V T | |
| | L i r D n F G N Y A L Q T l L D | |
| | L l n D s Y G N Y V L Q T a L D | 8 |
| | M m k D q Y A N Y V V Q K m I D | |
| | M m k D q Y A N Y V V Q K m I D | |

FIG. 24

GENES DETERMINING CELLULAR SENESCENCE IN YEAST

RELATED APPLICATIONS

The present Application is a continuation-in-part of Ser. No. PCT/US94/09351, filed Aug. 15, 1994, which is a continuation-in-part of U.S. Ser. No. 08/107,408, filed Aug. 16, 1993, now abandoned. The teachings of Ser. No. PCT/US94/09351 and Ser. No. 08/107,408 are incorporated herein by reference.

GOVERNMENT FUNDING

This invention was made, in whole or in part, with U.S. Government support under Contract Number NIH-5R01-GM30454 and NIH-1R01-AG11119 awarded by the National Institutes of Health. The U.S. Government has certain rights in the invention.

BACKGROUND OF THE INVENTION

Aging is a process in which all individuals of a species undergo a progressive decline in vitality leading to death. In metazoans, aging at the level of the whole organism is clearly evident. Whether the aging of an organism is genetically programmed, or represents the effects of entropy over time is not clear. Consistent with the possibility of a genetic program are mutations which alter the aging process. In humans the genetic diseases progeria and Werner's syndrome cause premature aging in affected individuals. In the earthworm *C. elegans*, a gene, age-1, has been described which directly or indirectly affects the life span of the animal (Friedman, D. B. and Johnson, T. E., *Genetics* 18:75–86 (1988)). A further issue open to speculation is how the aging of the entire organism relates to the aging of individual cells and cell types within the organism.

That individual cells within mammals do senesce was demonstrated in the findings of Hayflick, who showed that primary human diploid fibroblasts (HDFs) would grow in culture for about 50 population doublings, and then all the cells in the population would stop dividing (Hayflick, L. and Moorhead, P. S., *Exp. Cell Res.* 25:585–621 (1961); Hayflick, L., *Exp. Cell Res.* 37:614–636 (1965)). Cells arrest in the G1 phase of the cell cycle and contain a 2N chromosomal complement (Cristofalo, V. J., et al., *Exp. Gerontol.* 24:367 (1989)). This in phase, or clonal, senescence of the HDFs is accompanied by a characteristic morphological change; cells enlarge as they senesce (Angello, J. C., et al., *J. Cell. Physiol.* 132:125–130 (1987) and Cristofalo, V. J. and Kritchevsky, D., *Med. Exp.* 19:313–320 (1969)). In fact, this direct correlation between cell size and senescence can be demonstrated by incubating young HDFs in low serum-medium, in which they enlarge, but do not leave the G1 phase of the cell cycle (Angello, J. C., et al., *J. Cell. Physiol.* 140:288–294 (1989)). When these cells are returned to medium containing adequate serum for cell division, their program of senescence has been advanced compared to smaller cells which have divided the same number of times.

Cell fusion studies between old and young HDFs indicate that senescence is dominant. In short term hybrids, initiation of DNA synthesis in the young nucleus is inhibited after the young cell has been fused to a senescent HDF (Norwood, T. H., et al., *Proc. Natl. Acad. Sci. USA* 71:2231 (1974)). In fact, injection of polyA+ RNA from the senescent HDF into the young cell inhibits DNA synthesis (Lumpkin, C. K., Jr., et al., *Science* 232:393 (1986)), suggesting that the senescent HDF activated a gene or genes that encoded dominant inhibitory proteins. In complementation studies that involve fusing various "immortal" cell lines, four genes were identified which were involved in immortalization (Pereira-Smith, O. M. and Smith, J. R., *Proc. Natl. Acad. Sci. USA* 785:6042 (1988)). The dominance of senescence appears to conflict with the view that shortening of telomeres, a phenomenon observed during passage of fibroblasts (Harley, C. B., et al., *Nature* 345:458 (1990)), causes senescence.

In several lower eukaryotes, senescence has been demonstrated and linked to changes in mitochondria. In Podospora, cell senescence is strongly associated with the excision and amplification of segments of mitochondrial DNA (Cummings, D. J., et al., *J. Mol. Biol.* 185:659–680 (1985) and Koll, F. et al., *Plasmid* 14:106–117 (1985)). In Neurospora (Bertrand J., et al., *Cell* 47:829–837 (1986)) and Aspergillus (Lazarus, C. M., et al., *Eur. J. Biochem* 106:663–641 (1989)), senescent cells also contain rearrangements in their mitochondrial DNA. In all of the above examples, the senescent phenotype is dominant and is inherited cytoplasmically.

In the budding yeast, *Saccharomyces cerevisiae*, cells divide asymmetrically, giving rise to a large mother cell and a small daughter cell. By micromanipulating the daughter away from the mother at each cell division, it was shown that the mother divided a fixed number of times, and then stopped (Mortimer, R. K. and Johnston, J. R., *Nature* 183:1751–1752 (1959)). Life span was thus defined by the number of divisions mother cells had undergone, and not by chronological time. Further, a number of cell divisions in the life span of the mother, while fixed (varying over a Gompertz distribution (Pohley, J. -J. *Mech. Ageing Dev.* 38:231–243 (1987)), could differ from strain to strain (ranging from about 15 to 30) (Egilmez, N. K. and Jazwinski, S. M., *J. Bacteriol.* 171:37–42 (1989)). Thus, senescence in budding yeast as in HDFs is not a stochastic process, but has some underlying genetic basis.

Senescence in yeast is like senescence in HDFs in other ways as well. Like HDFs, yeast mother cells have been shown to enlarge with age (Mortimer, R. K. and Johnston, J. R., *Nature* 183:1751–1752 (1959) and Egilmez, N. K., et al., *J. Gerontol. Biol. Sci.* 45:B9–17 (1990)). In addition to their large size, aging mother cells also divide more slowly than young cells (Egilmez, N. K. and Jazwinski, S. M., *J. Bacteriol.* 171:37–42 (1989)). A further analogy to HDFs is that the senescent phenotype is also dominant in yeast. Mating a young yeast cell to an old one generates a diploid with a limited potential for cell division (Muller, I., *J. Microbiol. Serol.* 51:1–10 (1985)). In addition, daughters of old mothers display elongated cycling times for the first few divisions after separation from the old mother (Egilmez, N. K. and Jazwinski, S. M., *J. Bacteriol.* 171:37–42 (1989)). Evidently, the senescence substance is inherited by the daughter cell and slowly degraded or diluted in subsequent cell cycles.

The senescence of yeast mother cells thus has similarities to what occurs in primary HDFs; however, there is one important difference. In yeast at each cell division the daughter cell has regained the capacity for a full life span, whether derived from a younger or older mother cell (Muller, I., *Arch. Mikrobiol.* 77:20–25 (1971)). This "resetting" in daughters may be intertwined with the mechanism that generates asymmetry at cell division. In any case, "resetting" argues against one category of hypothesis for aging; namely that aging results from the accumulation of errors in protein synthesis, the error catastrophe theory (Orgel, L. E. *Nature* 243:441 (1973)). Because daughter cells derived from old mothers have functional mitochondria (Muller, I. and Wolf, F., *Mol. Gen. Genet.* 160:231–234 (1978)), this resetting also shows that senescence is not due to rearrangements in the mitochondrial genome.

By varying the growth rate of cells, it was demonstrated that the key parameter in determining the life span in yeast is number of divisions, and not chronological time (Muller, I., et al., *Mech. Ageing Dev.* 12:47–52 (1980)). This finding led to the idea that senescence could be due to an accumulation of bud scars in mother cells. Bud scars are deposits of chitin that stay with the mother cell after each cell division (Cabib, E., et al., *Curr. Top. Cell. Regul.* 8:1–32 (1974), and Pringle, J. R., et al., *Meth. Cell Biol.* 31:357–435 (1989)). Several lines of evidence have argued against the idea that bud scars cause aging. First, varying the surface to volume ratio of isogenic yeast strains by varying their ploidy did not affect life span (Muller, I., *Arch. Mikrobiol.* 77:20–25 (1971)). Second, increasing the surface area by mating an old cell to a young one did not endow the diploid with an increased potential for division (Muller, I., *J. Microbiol. Serol.* 51:1–10 (1985)). Third, induction of chitin synthesis and deposition in the cell wall did not decrease the life span of cells (Egilmez, N. K. and Jazwinski, S. M., *J. Bacteriol.* 171:37–42 (1989)). Thus, senescence in yeast has gross features similar to the aging process in mammalian cells. It is therefore reasonable to speculate that the molecular mechanisms of aging might be similar in yeast and mammalian cells, particularly in light of striking parallels in basic cellular mechanisms in yeast and mammalian cells. In the field of transcription, for example, there has emerged strong mechanistic similarities in the function of transcription factors: the yeast and mammalian TATA box binding factor TFIID, are interchangeable in the basal in vitro transcription reaction (Buratowski, S., et al., *Nature* 334:37–42 (1988)). Further, yeast and certain mammalian transcriptional activators will function normally in the heterologous host cells (see Guarente, L., et al., *Cell* 52:303–305 (1988) for review). Therefore, further study of aging in yeast cells may yield information concerning genes which are involved in senescence, and ultimately may shed light on the aging process in mammalian cells.

SUMMARY OF THE INVENTION

The present invention pertains to life span-determining genes which affect senescence in eukaryotic cells, such as budding yeast, and to mutated forms of the life span-determining genes. The genes of the present invention affect senescence either by contributing to aging or by conferring an extended life span upon the eukaryotic cell. Mutated genes of the present invention differ from wild type or naturally-occuring genes in that there is an addition, deletion, substitution or other alteration of the nucleic acid sequence, with the result that the encoded protein differs from the protein encoded by the non-mutated (wild-type) gene in at least one amino acid.

As described herein, it was discovered that the SIR4 is gene (silent information regulator) contributes to extended life span: when the SIR4 gene is deleted, the resulting mutant yeast cells have a significantly shorter life span than yeast cells which contain the SIR4 gene. However, when mutant yeast cells are generated by a specific mutation in the SIR4 gene, the resultant mutant cells have a life span that is significantly longer than the life span of the non-mutant strain. The mutation is an amber mutation that removes 121 residues from the 1358 residue SIR4 protein.

It has also been discovered that the UTH4 gene affects senescence in a manner similar to that of SIR4. That is, a particular mutation in the UTH4 gene confers extended life span on mutant yeast cells.

As further described herein, it was discovered that the UTH1 gene effects senescence by contributing to the aging process. In particular, deletion of the UTH1 gene confers extended life span on the mutant yeast cell comapred with the life span exhibited by yeast cells which contain the UTH1 gene.

Additional genes have been identified which show strong homology to the UTH4 and UTHI genes. In particular, the yeast YGL023 and Drosophila PUMILIO gene, as well as the human D43951 and D13645 genes, show strong homology to UTH4. The yeast NCA3 gene and the SAG1 gene show strong homology to the UTHI gene. Deletion of either the NCA3 or SAG1 gene result in shortened yeast cell life span compared with wild-type (non-deleted) yeast cells. This indicates that NCA3 and SAG1 are genes which contribute to extended life span in yeast.

As a result of these discoveries, methods of isolating mutant yeast cells with increased life span, and the mutant yeast cells isolated by these methods, are now available. Also available are methods to identify agents which enhance the life span of yeast cells; methods to isolate genes involved in senescence, as well as the genes isolated thereby, and the proteins encoded by the genes.

As described in detail below, the current invention comprises several methods of isolating yeast cells with increased life spans (a life span longer than the known life span of the non-mutagenized yeast strain). In each method, a sample of yeast cells from a budding yeast strain, for which the life span is known or has been calculated, is exposed to a mutagen, and then the mutagen-exposed yeast cells are cultured. In one embodiment of the current invention, mutant yeast cells are identified first by the related phenotype of starvation resistance. The yeast cells are plated on minimal medium, replica-plated on starvation medium, and grown. The plate with starvation medium is replica-plated to enriched medium; those colonies which grow are starvation resistant. The starvation-resistant colonies are then examined to isolate cells with longer life spans.

In a second embodiment, the cell surface of yeast cells are labelled with a fluorescent marker. New cells remain unlabelled. After a period of growth greater than the known life span of the yeast strain, the cells are subjected to fluorescence-activated cell sorting to isolate the fluorescent-labelled cells, which are then plated. Only those cells with longer life spans grow. In another embodiment, a temperature-sensitive budding yeast strain, in which the daughter cells die at the non-permissive temperature, is used. When cells from the temperature-sensitive strain are grown at the non-permissive temperature, they form microcolonies in which the number of cells in the microcolony is equivalent to the number of generations in the life span of the yeast strain. Larger microcolonies, which are comprised of cells with a longer life span, are identified. Cells with increased life spans, isolated by any of these methods, are also part of the current invention.

The current invention also comprises methods of identifying agents which increase life span. Cells from a budding yeast strain with a known life span are exposed to the agent to be tested; the cells are then cultured and examined to determine whether they have longer life spans, using any of the methods described above. The presence of cells having longer life spans is indicative of the ability of the agent to increase life span of the cells.

In addition, the current invention pertains to genes which are involved in senescence of organisms, including yeast, bacteria and vertebrates, particularly mammals. Genes can be isolated by complementation analysis. For example, a genomic DNA library is constructed for the organism of interest, and is transformed into a mutant yeast strain having a mutated gene which contributes to longer life span, such as a mutant SIR4 gene. The DNA from the organism of interest is then isolated from those transformants which have the usual life span (i.e., those cells from the mutant yeast strain which no longer have a longer life span).

Alternatively, genes which are homologous to and/or hybridize to a gene that is known to affect senescence, such as SIR4, can be identified and/or isolated. The isolated genes, and the proteins encoded by the genes, are also the subject of the current invention. The subject invention also relates to DNA which encodes a protein which affects senescence in an organism (eukaryotes such as yeast and mammals, including humans, and prokaryotes). This includes UTH1 (SEQ ID NO. 1), DNA which is homologous to and/or hybridizes to UTHI, such as NCA3 (SEQ ID NO. 11) and SAGI (SEQ ID NO. 13), and DNA which encodes the same amino acid sequence as that encoded by UTH1, NCA3 or SAG1. This invention also relates to UTH1, NCA3 or SAG1 DNA which has been mutated, including mutations which cause non-expression of the encoded protein, DNA which is homologous to and/or hybridizes to the mutant UTH1, NCA3 or SAG1 DNA, and DNA which encodes the same amino acid sequence as that encoded by mutant UTH1, NCA3 or SAG1 DNA. This invention also includes proteins encoded by UTH1, NCA3 or SAG1 DNA and similar DNA sequences, as well as to proteins encoded by mutated UTH1, NCA3 or SAG1 DNA.

This invention also pertains to the UTH4 gene (SEQ ID NO. 3), DNA which is homologous to and/or hybridizes to UTH4, such as YGL023 (SEQ ID NO. 5), D43951 (SEQ ID NO. 7, FIGS. 18A–G) and D13645 (SEQ ID NO. 9), and DNA which encodes the same amino acid sequence as that encoded by UTH4, YGL023, D43951 or D13645. Also included is UTH4, YGL023, D43951 and D13645 DNA which has been mutated, including mutations which cause non-expression of the encoded protein or mutations which encode a stop codon, DNA which is homologous to and/or hybridizes to the mutant UTH4, YGL023, D43951 or D13645 DNA, and DNA which encodes the same amino acid sequence as that encoded by mutant UTH4, YGL023, D43951 or D13645 DNA. Further included are proteins encoded by UTH4, YGL023, D43951 and D13645 DNA and similar DNA sequences, as well as to proteins encoded by mutated UTH4, YGL023, D43951 or D13645 DNA.

Further, this invention includes DNA which is homologous to and/or hybridizes to SIR4 and DNA which encodes the same amino acid sequence as that encoded by SIR4. It also relates to mutant SIR4 DNA (which includes a stop codon at amino acid 1237 of the encoded protein), DNA which is homologous to and/or hybridizes to the mutant SIR4 DNA, and DNA which encodes the same amino acid sequence as that encoded by mutant SIR4 DNA. The present invention also relates to proteins encoded by mutant SIR4 DNA and the similar mutant SIR4 DNA sequences.

BRIEF DESCRIPTION OF THE FIGURES

FIGS. 15A–B are a depiction of the nucleic acid sequence (SEQ ID NO. 1), and the encoded amino acid sequence (SEQ ID NO. 2), of the UTH1 gene.

Figure 16B:
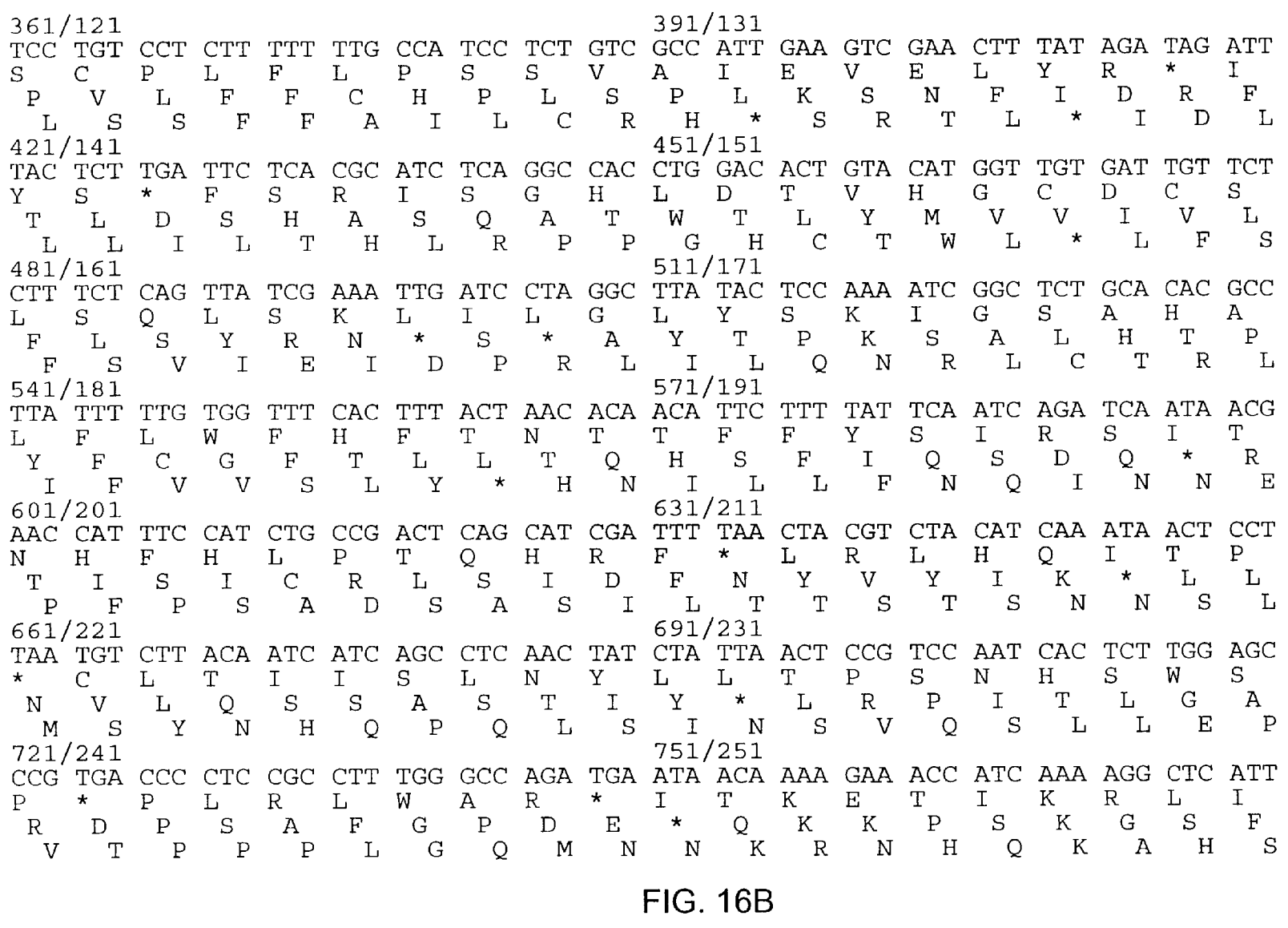
Figure 16C:
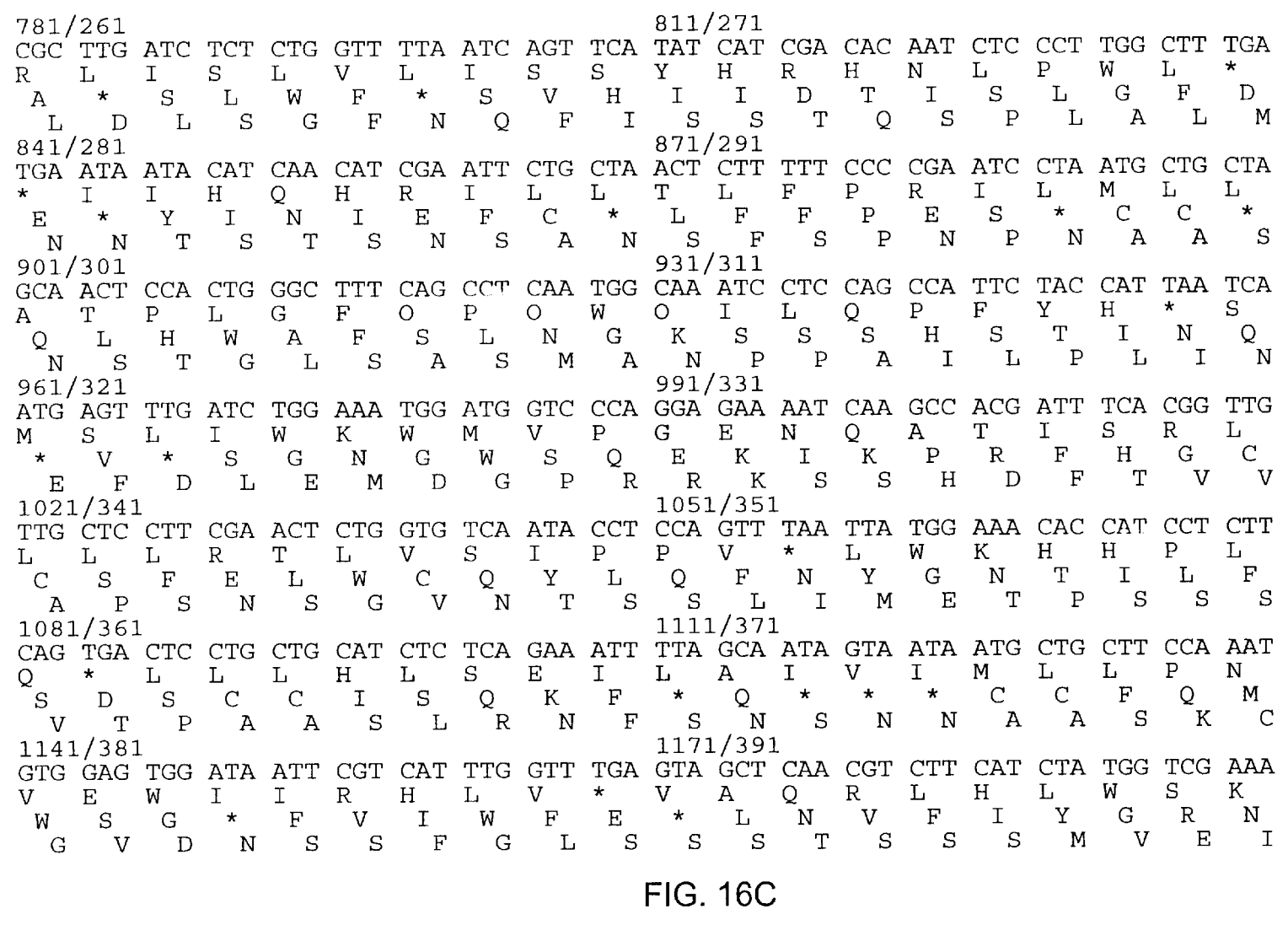
Figure 16D:
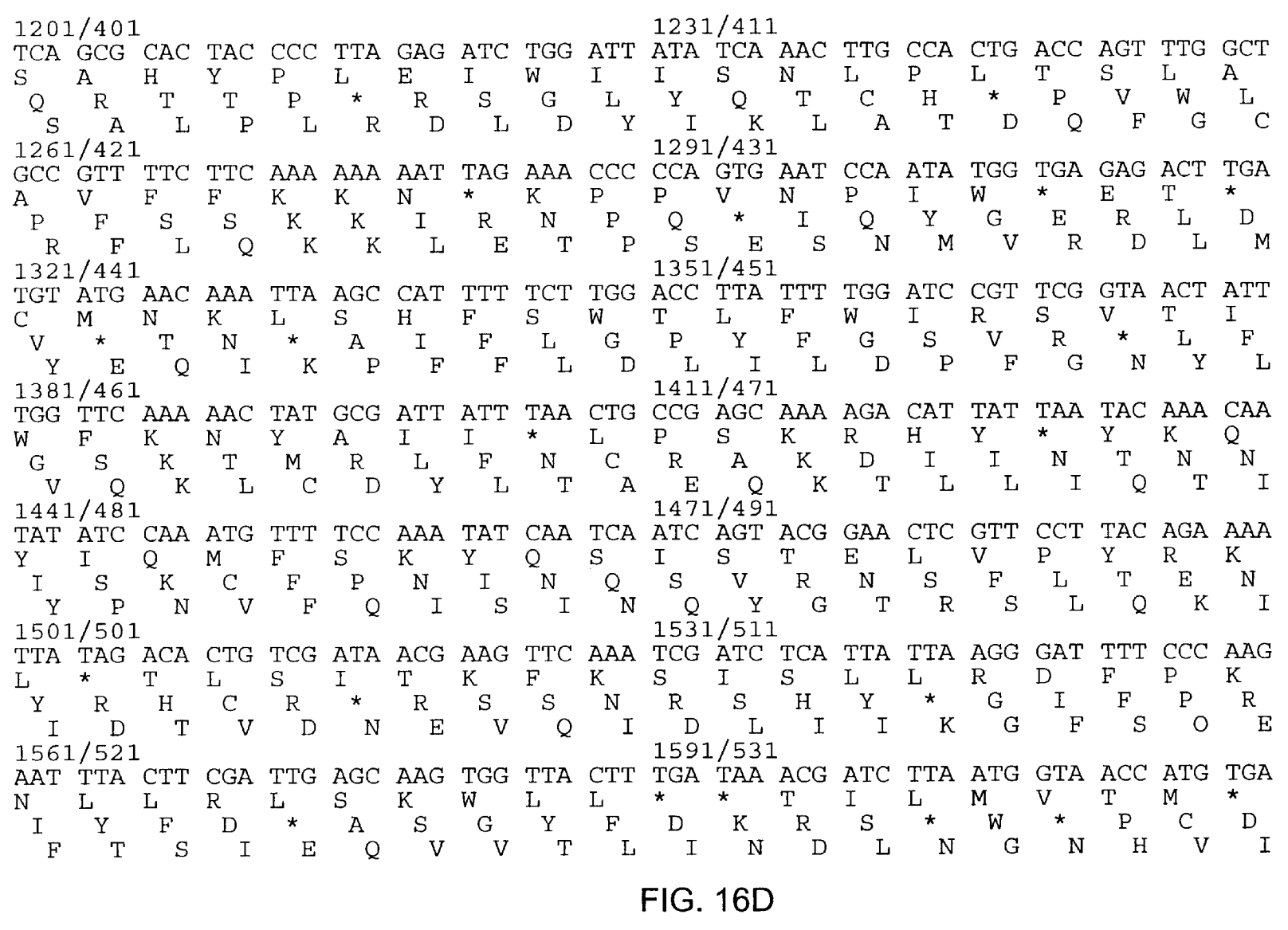
Figure 16G:
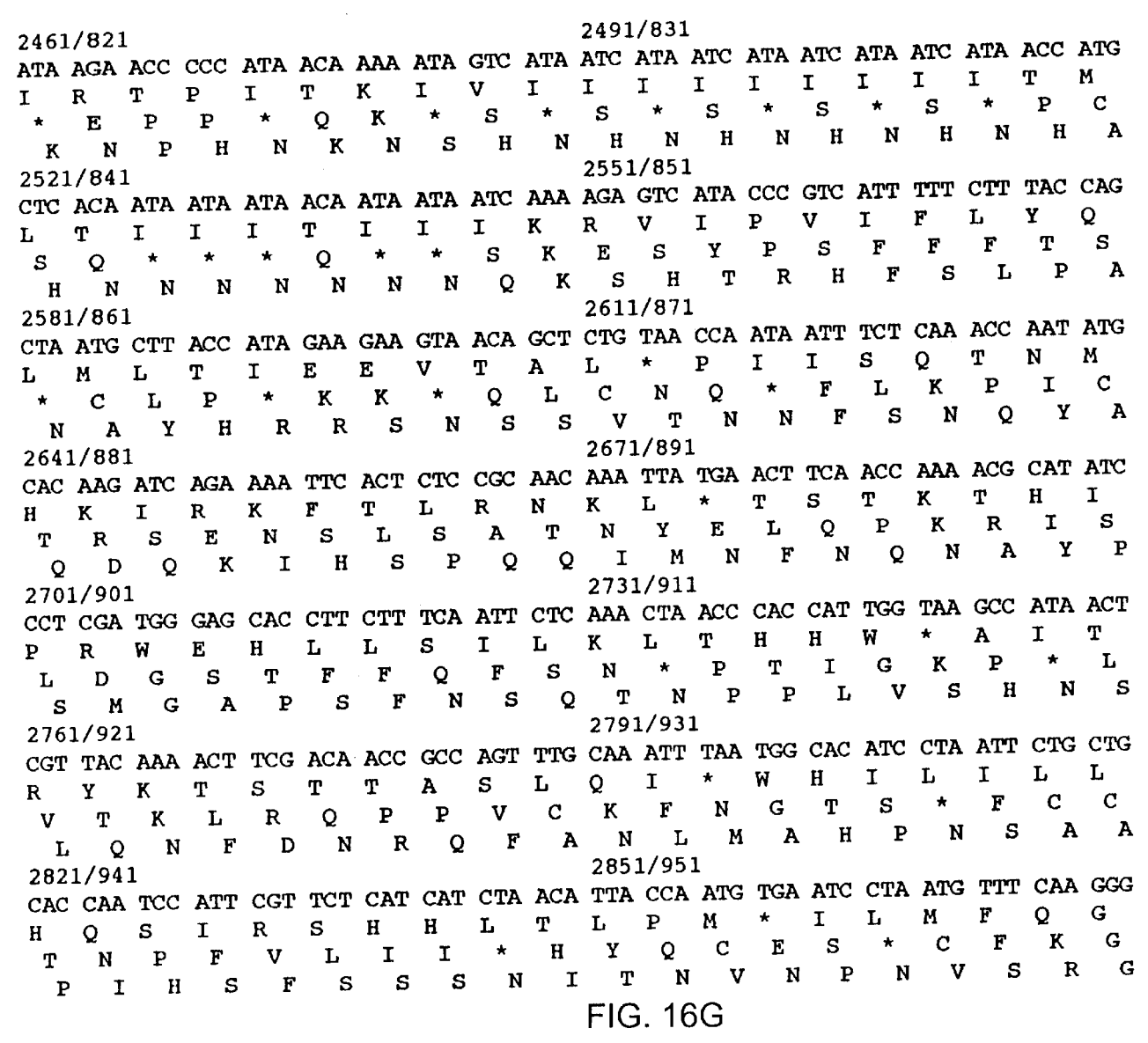

FIGS. 16A–I are a depiction of the nucleic acid sequence (SEQ ID NO. 3), and the encoded amino acid sequence (SEQ ID NO. 4), of the yeast UTH4 gene.

FIGS. 17A–J are a depiction of the nucleic acid sequence (SEQ ID NO. 5), and the encoded amino acid sequence (SEQ ID NO. 6), of the yeast YGL023 gene.

Figure 18C:
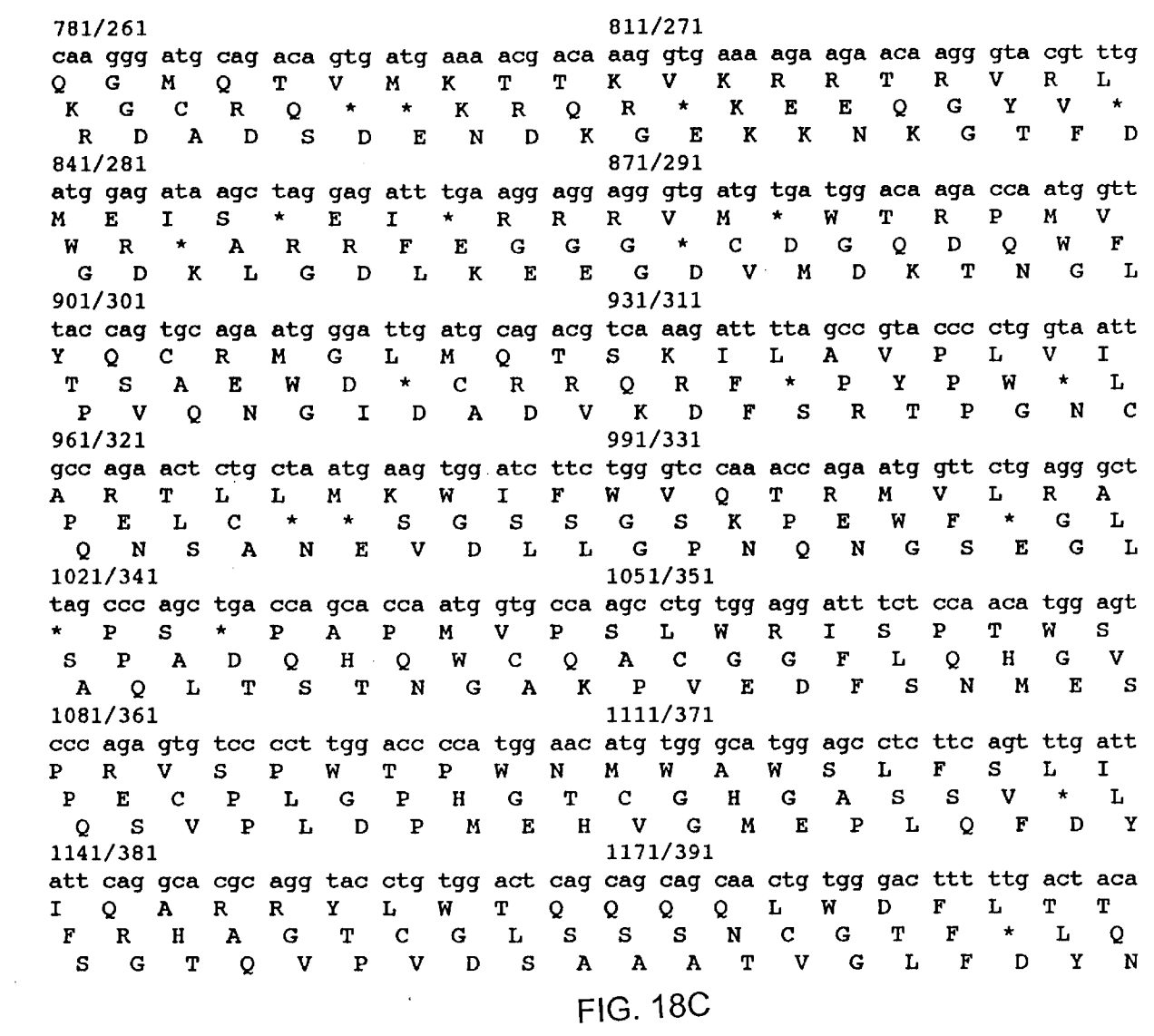
Figure 18H:
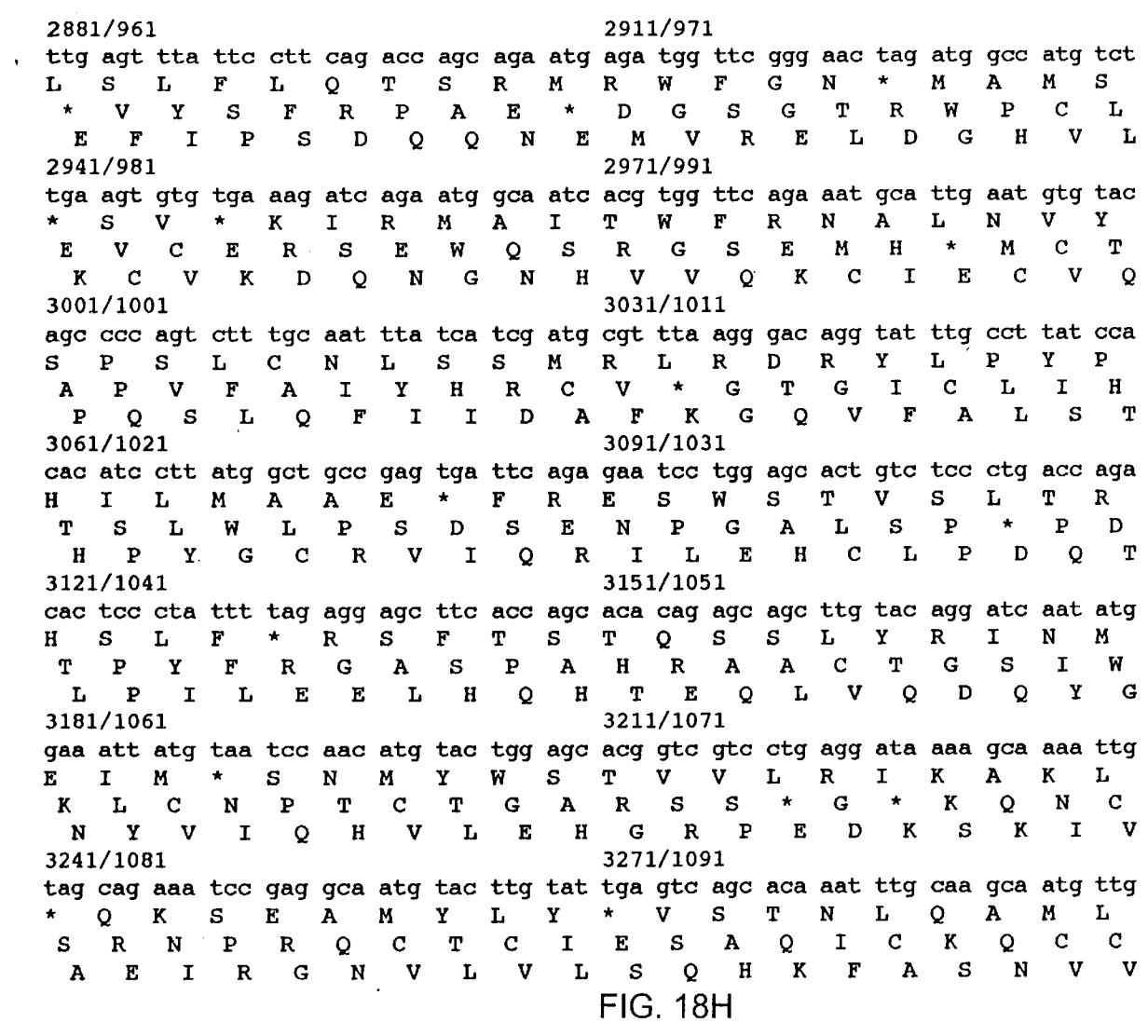
Figure 18L:
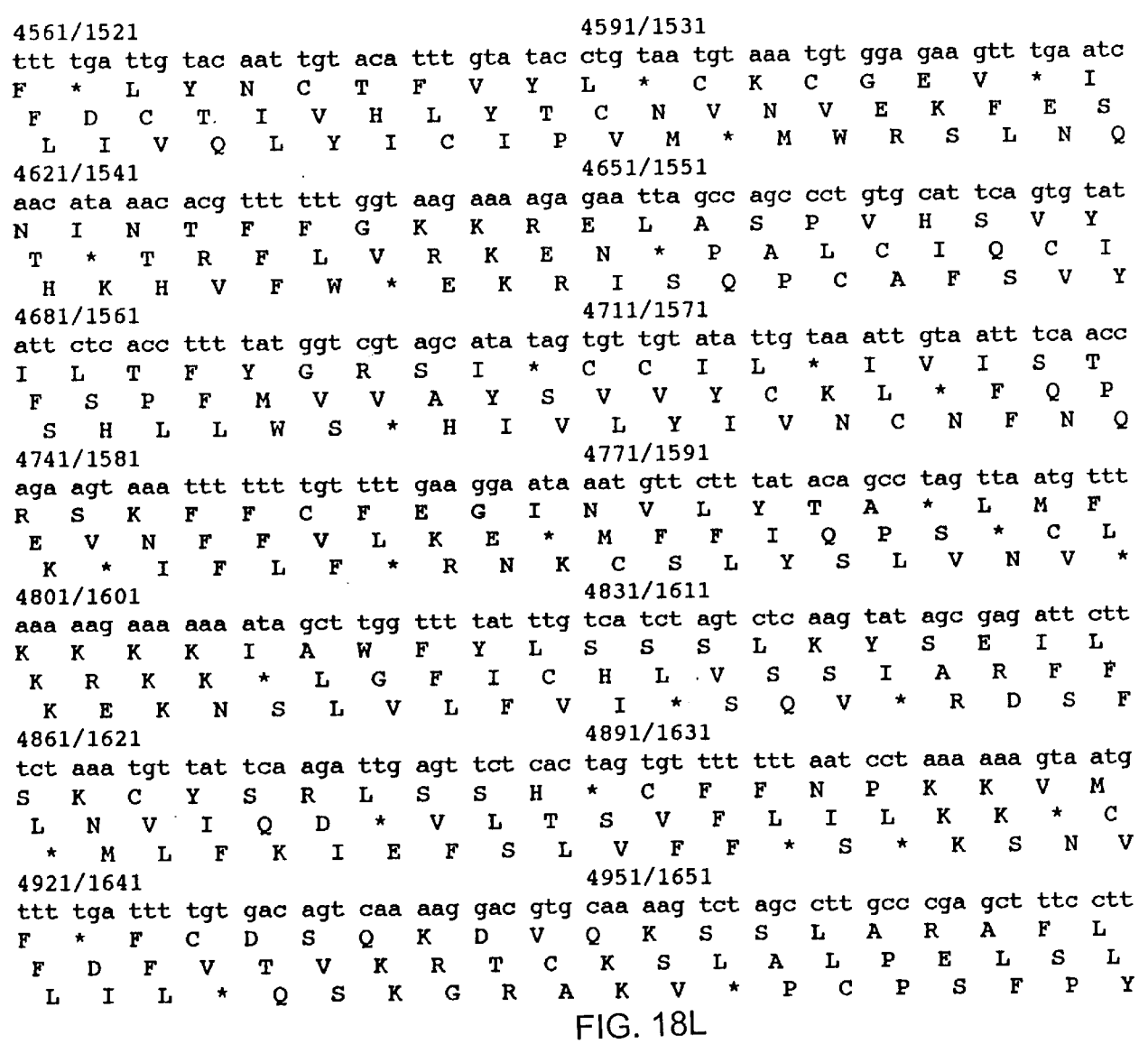

FIGS. 18A–M are a depiction of the nucleic acid -sequence (SEQ ID NO. 7), and the encoded amino acid sequence (SEQ ID NO. 8), of the human D43951 gene.

FIGS. 19A–H are a depiction of the nucleic acid sequence (SEQ ID NO. 9), and the encoded amino acid sequence (SEQ ID NO. 10), of the human D13645 gene.

FIGS. 20A–B are a depiction of the nucleic acid sequence (SEQ ID NO. 11), and the encoded amino acid sequence (SEQ ID NO. 12), of the yeast NCA3 gene.

FIGS. 21A B are a depiction of the nucleic acid sequence (SEQ ID NO. 13), and the encoded amino acid sequence (SEQ ID NO. 14), of the yeast SAG1 gene.

FIGS 22A–C are an illustration of the consensus sequence (SEQ ID NO. 15) from the SUN domains of the UTH1, NCA3 and SAG1 genes, as well as a comparison of the consensus sequence and a partial sequence of the SUN4 gene (SEQ ID NO. 16).

FIG. 23 depicts a comparison of the amino acid sequences of the eight repeat boxes of UTH4. Capital letters indicate conserved amino acids.

FIG. 24 depicts a comparison of the amino acid sequences of the eight repeat boxes of the UTH4, YGL023, Drosophila PUMILIO and human D43951 genes. Capital letters indicate conserved amino acids.

DETAILED DESCRIPTION OF THE INVENTION

The present invention derives from the discovery that a particular gene is involved in senescence in yeast, and that a particular mutation in the gene causes an increase in life span of the yeast cells. As described below, longer-lived mutant yeast cells have been isolated in which the SIR4 gene has been mutated to generate a stop codon at amino acid 1237 of the enclosed protein. As a result of this finding, it is now possible to identify and/or isolate yeast cells with longer life spans, as well as to identify agents which contribute to longer life span. It is further possible to isolate genes involved in (which have an effect on) senescence, as well as the proteins encoded by these genes, and genes encoding proteins that contribute to longer life span.

The following is a description of the discovery of a phenotype correlating with life span; the isolation of mutant yeast strains with longer life spans; the isolation and characterization of the mutant gene affecting life span; the requirements of other genes to lengthen life span; the effects of the mutant gene on telomeres; extension of life span expression of the carboxyl-terminus of the gene; a framework for relating silencing, aging, stress, and telomeres; methods of isolating strains with longer life spans; methods of identifying agents which affect life span; and methods of isolating genes involved in cellular senescence.

Identification of a Phenotype Correlating with Life Span

Because budding yeast cells divide asymmetrically into a large mother cell and a small daughter cell, the life span of any given mother cell in a particular colony can be measured. By visualizing growing cells in a microscope and micromanipulating away the daughter cell after each division, it is possible to follow a pedigree from each starting cell. The end of the life span for a given cell is indicated by a cessation of cell division. Life span is thus equated with the number of generations, or divisions, which give rise to daughter cells. The life span of a particular strain can be identified by the mean number of generations in several colonies. The chronological life span, therefore, is the approximate time necessary for one cell division, or for one generation to arise, multiplied by the number of divisions (generations) in the mean life span. A longer life span, as described herein, is measured as an increase in the mean life span of one strain as compared with the mean life span of a second strain.

Figure 1:
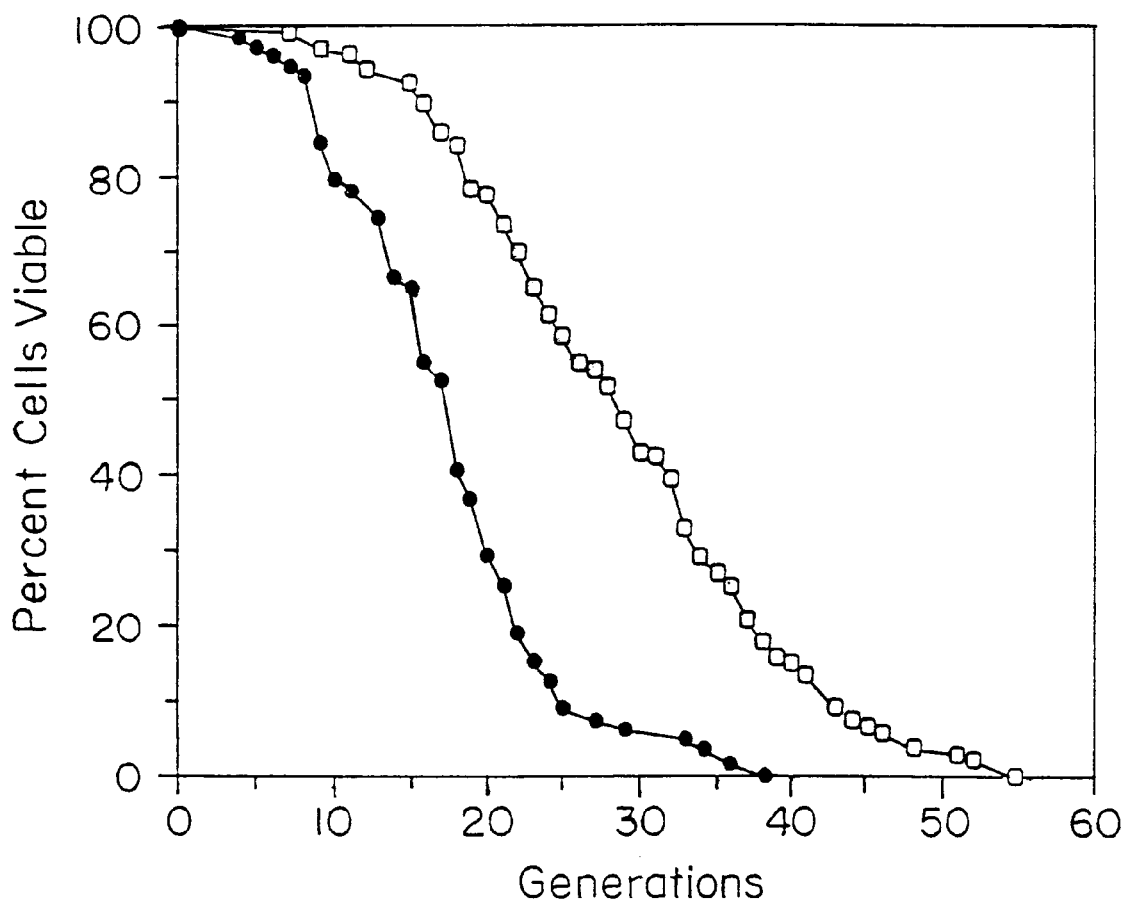
FIG. 1 is a graphic representation of the mortality -curves for two strains of S. cerevisiae, BWG1-7A (closed symbols), and PSY142 (open symbols).
Figure 2A:
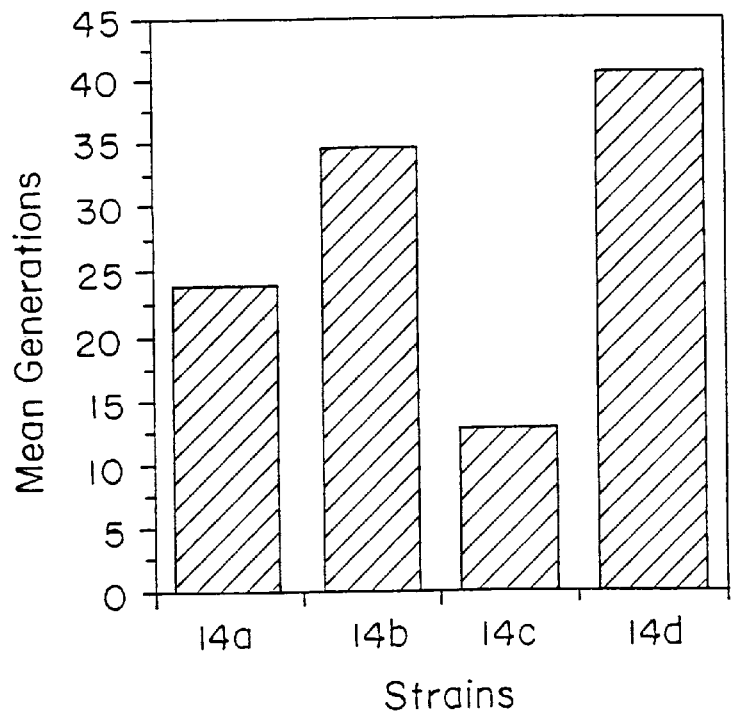
FIGS. 2A and 2B is are is a graphic representation of the mean life spans of the four strains in the tetrad BKx1-14.
Figure 2B:
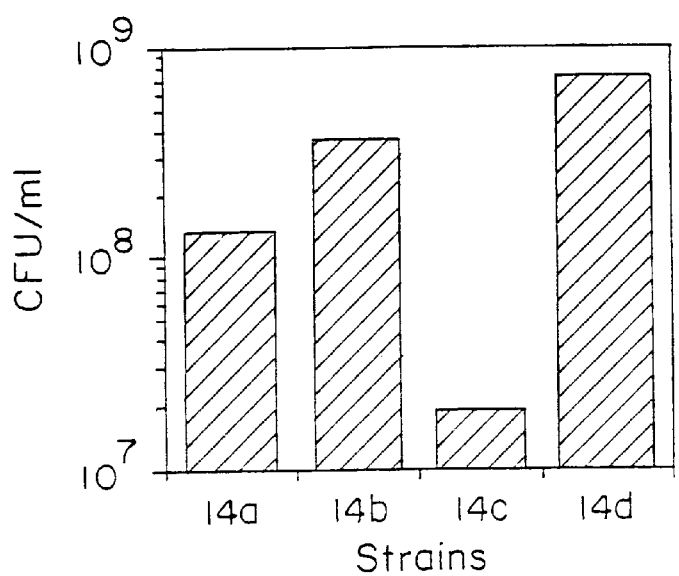
Figure 3:
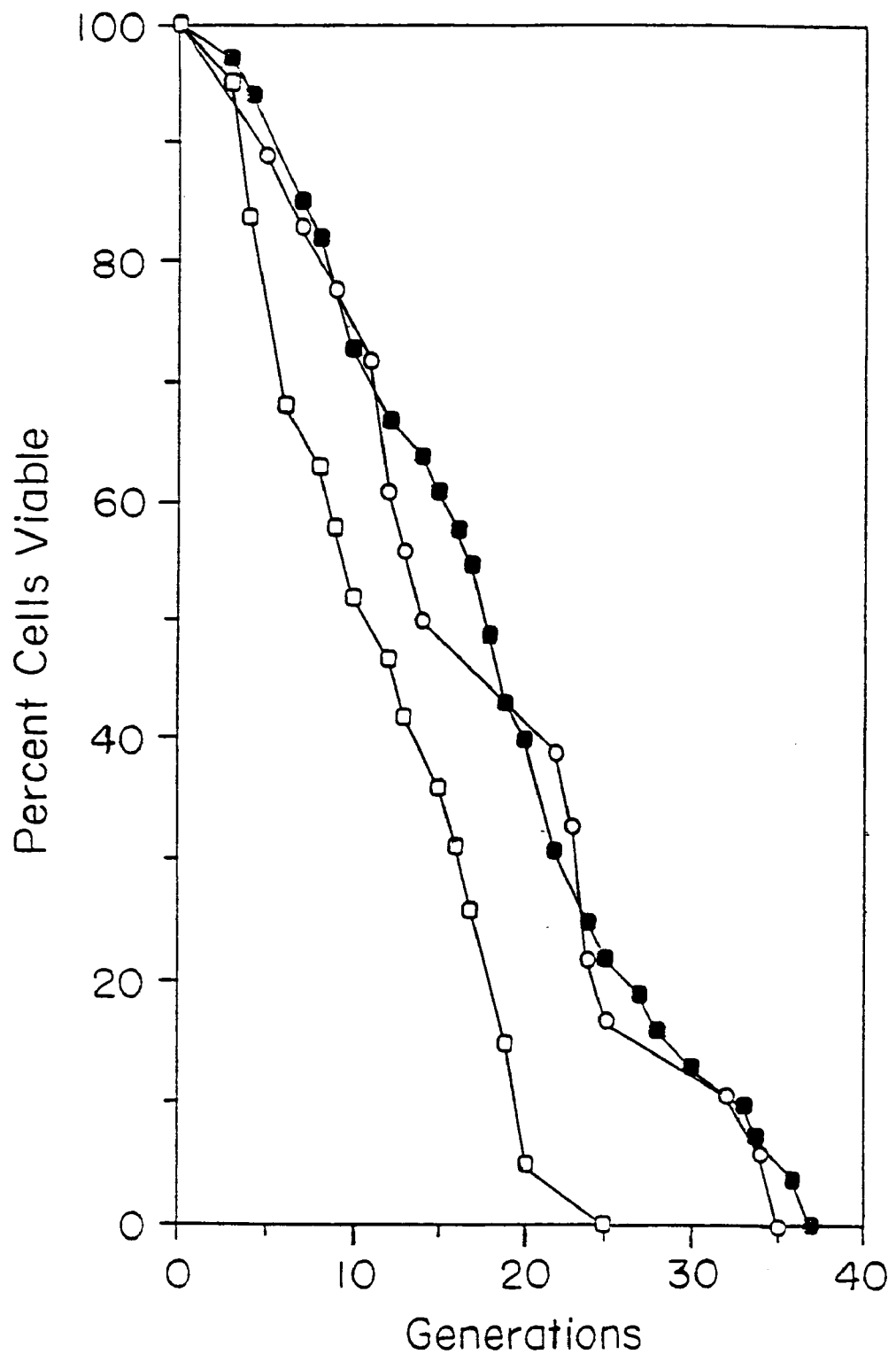
FIG. 3 is a graphic representation of the viability of the tetrad strains after 7 days of starvation.

To facilitate the identification of strains with altered life spans, a phenotype was sought which correlated with life span, yet which could be studied at the level of populations of cells (i.e., at a colony level). To this end! two parental strains were used, BWG1-7A (Guarente, L. et al., *Cell* 36:503–511 (1984)), and PSY142 (laboratory strain). These two strains had different mean life spans (18 generations for BWG1-7A, and 29 generations for PSY142), as shown in FIG. 1. Four strains of *Saccharomyces cerevisiae* were generated by crossing the parental strains BWG1-7A and PSY142 and sporulating the diploid. These four segregants of this cross, known collectively as the tetrad BKxl-14 strains and individually as 14a, 14b, 14c, and 14d, have varying life spans (see FIG. 2). When the tetrad strains were starved for nitrogen and carbon, it was discovered that starvation contributed to cell death, and that the rate of cell death when starved was inversely proportional to the life span of the particular strain. That is, longer-lived strains were more resistant to starvation-induced death than shorter-lived strains (see FIG. 3). Furthermore, strains with longer life spans yielded a greater recovery of viable cells after storage at 4° C. for 4.5 months.

Isolation of Longer-lived Mutant Yeast Strains

To isolate longer-lived mutants, the shorter-lived strain 14c, which was relatively sensitive to starvation-induced cell death, was utilized. The yeast strain 14c has been deposited with the American Type Culture Collection, 12301 Parklawn Drive, Rockville, Md., 20852, USA, under the Budapest Treaty on the International Recognition of the Deposit of Microorganisms for the Purposes of Patent Procedure, on Aug. 13, 1993; the accession number is 74236. All restrictions on the-availability to the public of the deposited material will be irrevocably removed upon the granting of the patent. 14c yeast cells were mutagenized with ethylmethane sulfonate (EMS) (approximately 60% of cells killed); colonies were plated on supplemented minimal plates (yeast nitrogen base, 2% glucose, and those amino acids and nucleotides required for the strain) and replica-plated to plates lacking nitrogen and carbon (the starvation plates) (contents identical to supplemented minimal, without nitrogen and carbon). After incubation of the starvation plates at 30° C. for five to ten days, the plates were replicated back to rich media plates (YPD) (1% yeast extract, 2% peptone, 2% dextrose). Most of the colonies consisted of dead cells, and thus did not grown on YPD; however, rare colonies contained living cells when plated back onto YPD (the "starvation resistant" colonies). Of 38,000 colonies, 39 were starvation resistant. Of these, eight had an extended life span (extended 20–55%). To determine the life span, cells were taken from logarithmically growing liquid cultures and plated at low density on complete medium. The plates were incubated at 30° C. for approximately three hours. At this time, daughter cells were isolated as buds that had emerged from mother cells, and moved with a Zeiss Micromanipulator to uninhabited regions of the plate. The life spans of these cells were determined by noting and removing all subsequent daughters they generated. The plates were incubated at 30° C. during working hours and shifted to 4° C. overnight. Life spans generated by this incubation schedule do not differ significantly from those generated by incubating cells continuously at 30° C. (data not shown).

To determine whether the mutants were dominant or recessive, the eight starvation resistant mutants were crossed with an isogeneic derivative of 14c, BKyS, with the opposite mating type, sporulated, and shown to segregate 2:2 for stress-related phenotypes in more than 10 tetrads each. Genetic analysis indicated that seven were recessive and one was dominant. Complementation analysis showed that the recessive mutations fell into three genes (UTH 1, 2, and 3). The dominant mutation was not linked to representatives of any of these groups, and representatives of each group were not linked to each other. The dominant mutation was identified as a fourth gene (UTH4, SEQ ID NO. 3, FIG. 16A–E).

Figure 4:
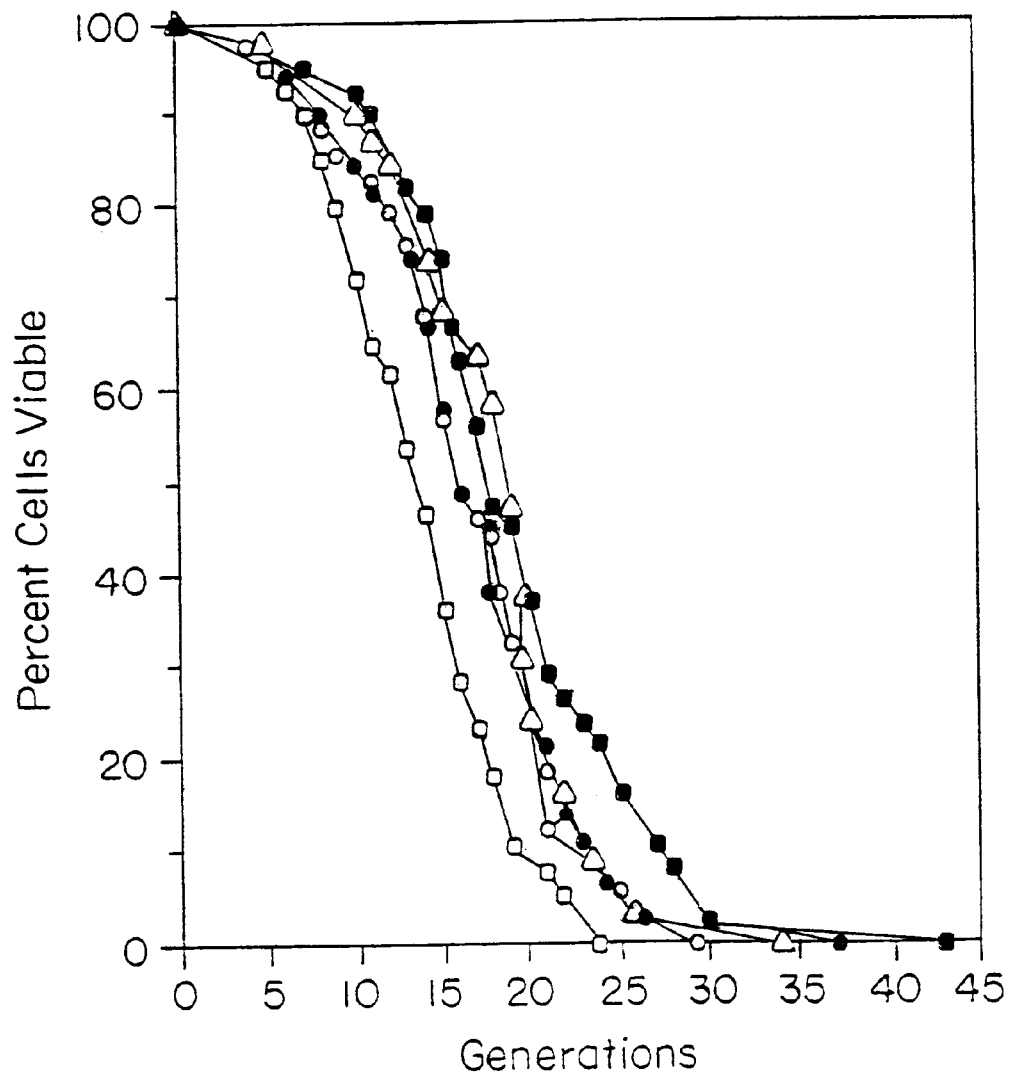
FIG. 4 is a graphic representation of mortality curves for UTH1 mutants. Sample sizes were 37 cells (uth1-324, closed cicles), 38 cells (uth1-328, open triangles)), 38 cells (uth1-330, closed squares), 34 cells (uth1-342, open circles), and 40 cells (14c, open squares).
Figure 5:
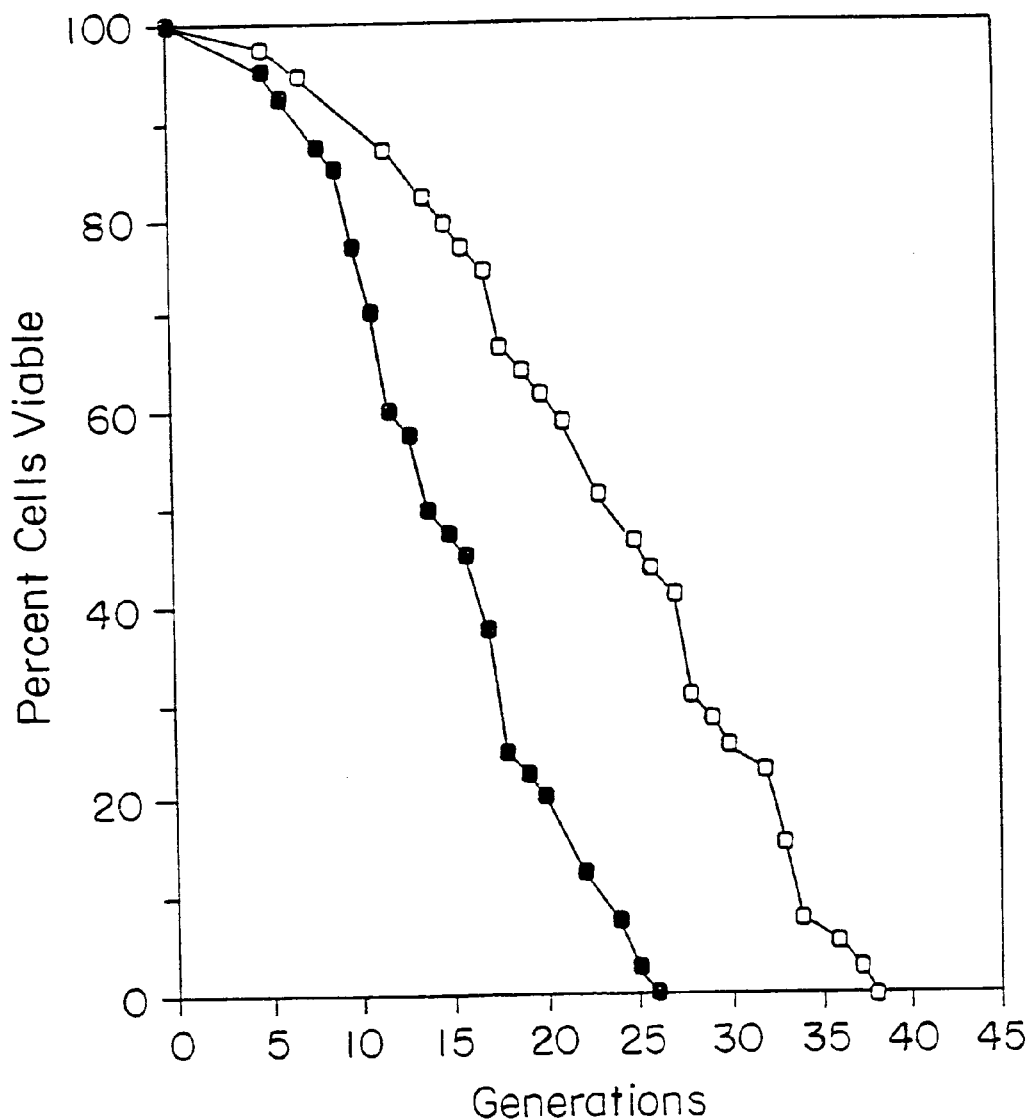
FIG. 5 is a graphic representation of mortality curves for UTH2 mutants. Sample sizes were 40 cells (uth2-42, closed figures), and 40 cells (14c, open figures).
Figure 6:
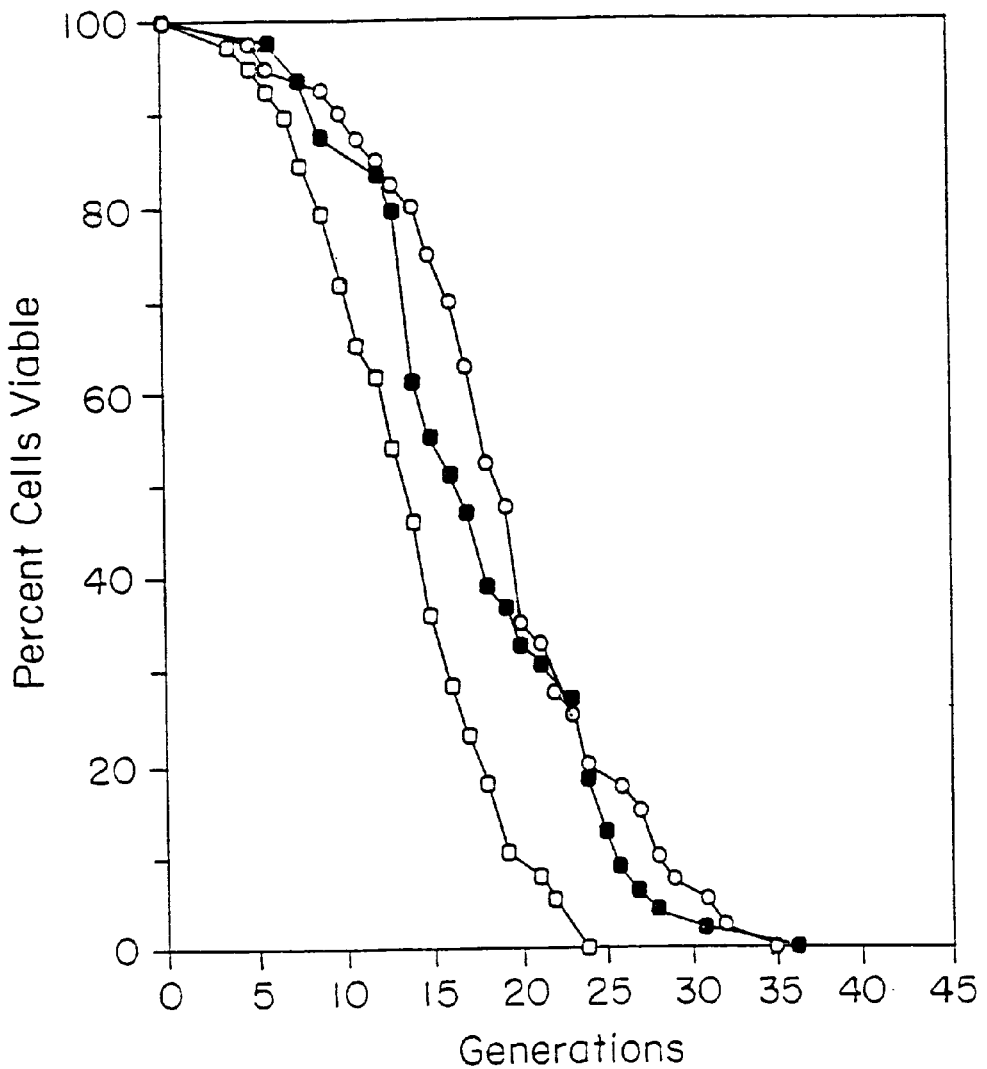
FIG. 6 is a graphic representation of mortality curves for UTH3 mutants. Sample sizes were 49 cells (uth3-26, closed squares), 40 cells (uth3-335, open circles), and 40 cells (14c, open squares).
Figure 7:
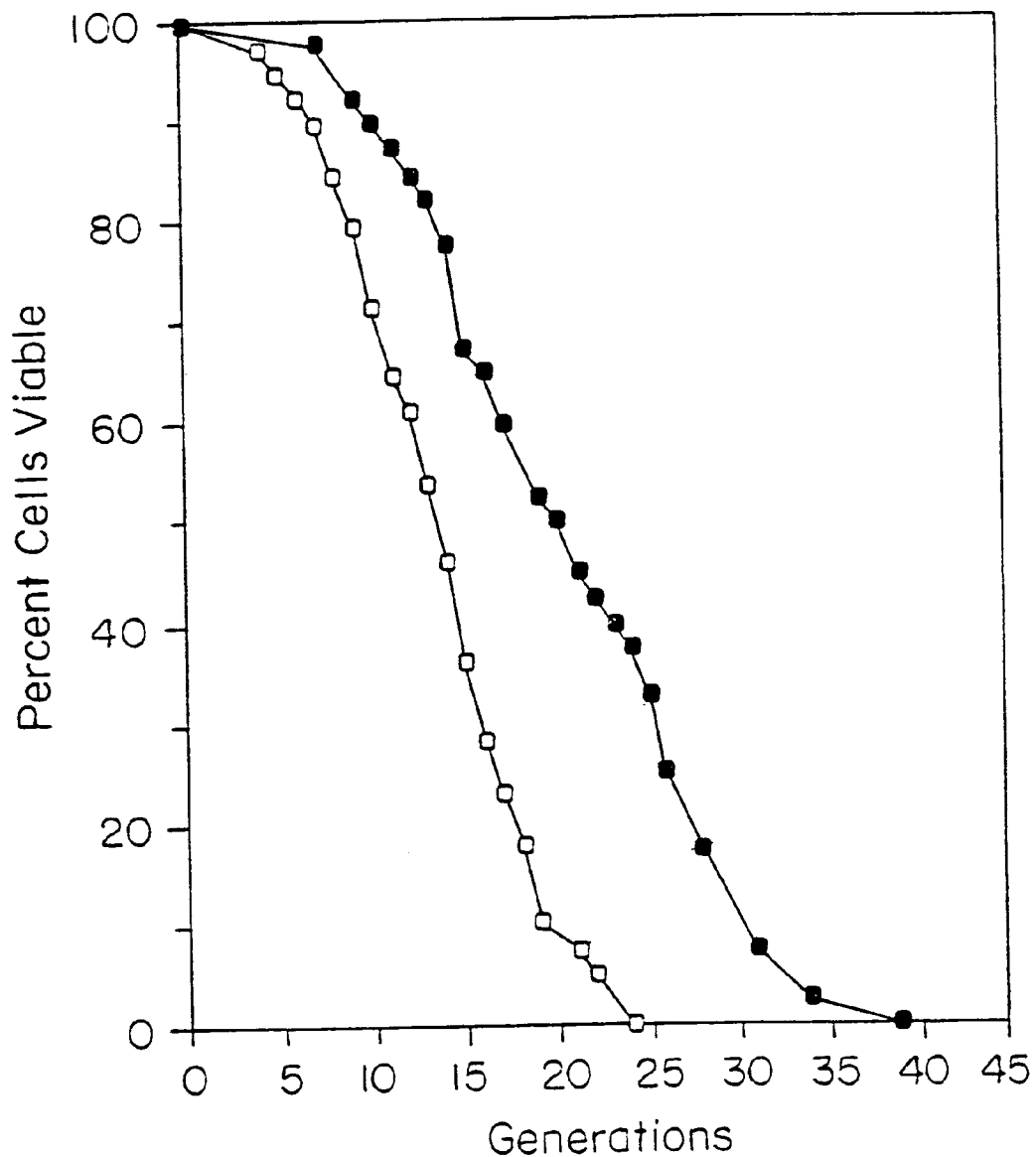
FIG. 7 is a graphic representation of mortality curves for UTH4 mutants. Sample sizes were 40 cells (uth4-326, closed squares), and 40 cells (14c, open squares).

Mortality curves for each complementation group (UTH 1–4) are shown in FIG. 4 (UTH1), FIG. 5 (UTH2), FIG. 6 (UTH3), and FIG. 7 (UTH4). The differences in life span were statistically significant by a Wilcoxen signed rank test.

Several different phenotypes were examined. To determine starvation resistance, haploid cells were grown in rich media to log phase, collected by centrifugation, and resuspended in minimal sporulation media for a period of seven to nine days. After starvation, cells were again collected by centrifugation and plated on rich media to measure colony forming units (cfu)/ml. Colonies could be assayed for ability to withstand starvation by utilizing sporulation plates instead of liquid culture. Saturation density was measured by suspending logarithmically growing cells in rich medium liquid culture at a density of $10^6$ cells/ml. Cultures were incubated for a period of five days with the number of cells/ml counted in a hemacytometer on a periodic basis. Control experiments indicated that the media was completely saturated after this time period. Heat shock resistance was determined by collecting logarithmically growing cells and plating them at a known concentration on rich media plates. The cells were heatshocked at 55° C. for periods varying from five minutes to one hour. Plates were then incubated at 40° C. for three days and the number of colonies was counted. Growth on ethanol was measured by directly streaking a strain on either rich media containing ethanol or synthetic media supplemented with necessary nutrients and containing ethanol as the sole carbon source.

All eight mutants had phenotypes that were different from the parental 14c strain: better stress survival rate (resistance to nitrogen starvation); extended life span (as shown by more divisions); growth to a higher saturation density; heat shock resistance; enhanced growth on ethanol (a carbon source that induces the heat shock response in *S. cerevisiae*) (Plesset, *Biochem. Biophys. Res. Comm.* 108:1340–1345 (1982)); caffeine resistance; and paraquat sensitivity. In addition, one mutant, designated uth2-42, displayed two additional phenotypes: it mated poorly, and exhibited a pseudohyphal-like growth pattern. The latter phenotype has been observed in diploids that were starved for nitrogen (Gimeno, C. et al., *Cell* 68:1077–1090 (1992)). Sterility and pseudohyphal-like growth both cosegregated with stress tolerance. Moreover, in three complete tetrads it was found that a lengthened life span also cosegregated with the other mutant phenotypes.

Isolation and Characterization of Genes Affecting Life Span
Isolation of the UTH2 gene was conducted by the ability of UTH2 to restore mating to the uth2-42 strain, assayed by replica-plating transformants to a lawn of a tester strain of opposite mating type (CKy21). The uth2-42 mutant was transformed with a standard yeast genomic library, CT3, on a URA3 plasmid (Thompson, C., et al., *Cell* 73:1361–1375 (1993)), by standard methods (Guthrie, C. and G. Fink, *Methods in Enzymology*, 1991), and Ura+colonies which were resistant to paraquat were selected. Transformed colonies were tested for their ability to complement the mating detect in the uth2-42 mutant. Plates containing library-transformed colonies were replica-plated onto permissive plates containing a lawn of strain CKy21. Cells were incubated at room temperature for one day to allow mating and then were replica-plated to plates selective for diploid growth. Colonies were picked which clearly grew on the selective plates. Plasmids were recovered from these colonies by standard methods and re-transformed into uth2-42 mutant cells. One plasmid restored the mating efficiency of the uth2-42 mutant. This plasmid, pBK40, also conferred heat shock sensitivity and starvation sensitivity to uth2-42, making it a good candidate for the UTH2 gene. pBK40 contained an insert of about 8 kb.

A 1.6 kb fragment located entirely within the pBK40 library insert was random primed by manufacturer's protocol (U.S. Biochemical), and used to probe a panel of lambda clones containing yeast DNA ((Riles, L. et al., *Genetics* 134:81–150 (1993)). Only one clone, the lambda clone that hybridized contained SIR4, showed a distinguishable signal.

SIR4 is a component of the yeast silencing complex that represses copies of MATα and MATa information and HML and HMR (Hartwell, L. H. *J. Cell. Biol.* 85:811–822 (1980); Laurenson, P. and J. Rine, *Microbiol. Rev.* 56:543–560 (1992); Rine, J. and I. Herskowitz, *Genetics* 116:9–22 (1987)). Restriction mapping of pBK40 indicated that it contained SIR4 and at least 1 kb of flanking DNA to either side. To determine linkage, the insert was transferred to a LEU2-containing integrating vector and targeted to the SIR4 locus in BKy5. This integrant (BKy3O) was mated with uth2-42 (containing pBK40 to allow mating), and after eviction of pBK40, the diploid sporulated. Thirteen of thirteen tetrads contained 2 Leu+, fertile:2 Leu-, sterile segregants, showing that SIR4 is tightly linked to the uth2-42 mutation. It was concluded that UTH2 was SIR4; therefore, uth2-42 was designated sir4-42.

The SIR4 gene is one of a series of genes (SIR1-4) involved in mating type switching. The SIR1-4 genes silence reserve copies of a and a information at the HML and HMR loci which are located to the left and right of the MAT mating type locus (see Rine, J. and Herskowitz, I., *Genetics* 116:9–22 (1987), for overview). The SIR1-4 genes also silence genes located at the telomeres of yeast chromosomes (Aparicio, O. M. et al., *Cell* 66(6):1279–1287 (1991)). No other functions had previously been attributed to these genes.

Figure 8:
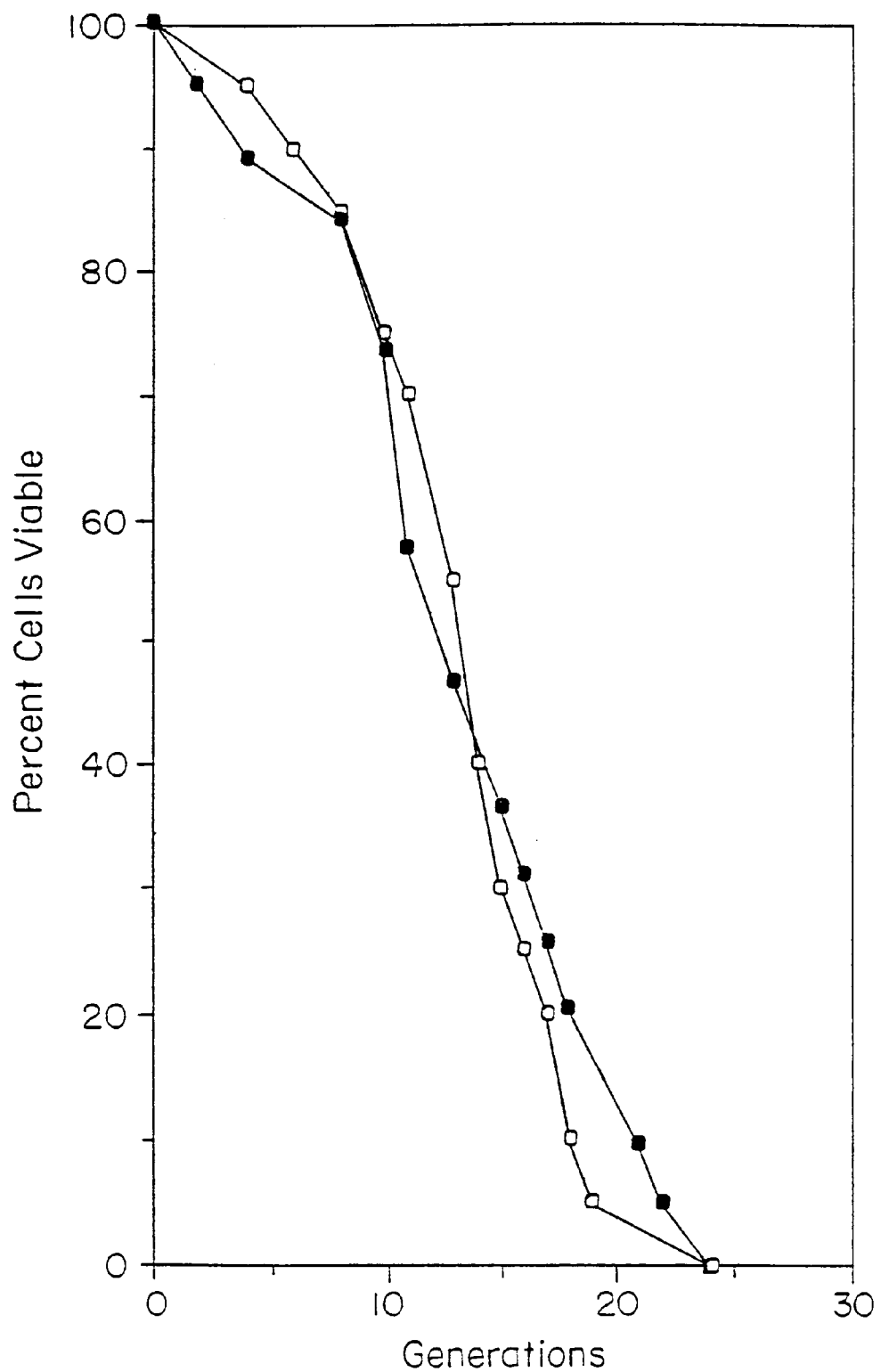
FIG. 8 is a graphic representation of the life span of haploid 14c (open squares) and diploid 14c (closed squares).

The SIR4 mutant is sterile because it expresses a and α information simultaneously. The effect of the SIR4 deletion was not simply because cells simultaneously expressed a and a information: the isogeneic diploid of 14c, BKy6, did not live longer than the haploid parents (14c and BKy5) (see FIG. 8). To generate BKy5, strain 14c was transformed with a (GAL-HO) plasmid and plated on galactose medium to induce mating type switching (Guthrie, C. and G. Fink, *Methods in Enzymology*, 1991). Colonies were tested by mating to CKy20 or CKy21 to determine their mating type; a MATa colony was picked and the GAL-HO plasmid was segregated using 5-FOA (Boeke, J. D. et al., *Meth. Enzymol.* 154:164–175 (1987)). This strain, BKy5, was mated to 14c and zygotes were isolated by micromanipulation to generate BKy6. To verify that BKy6 was a diploid, the strain was shown to be sporulation-competent.

Figure 9:
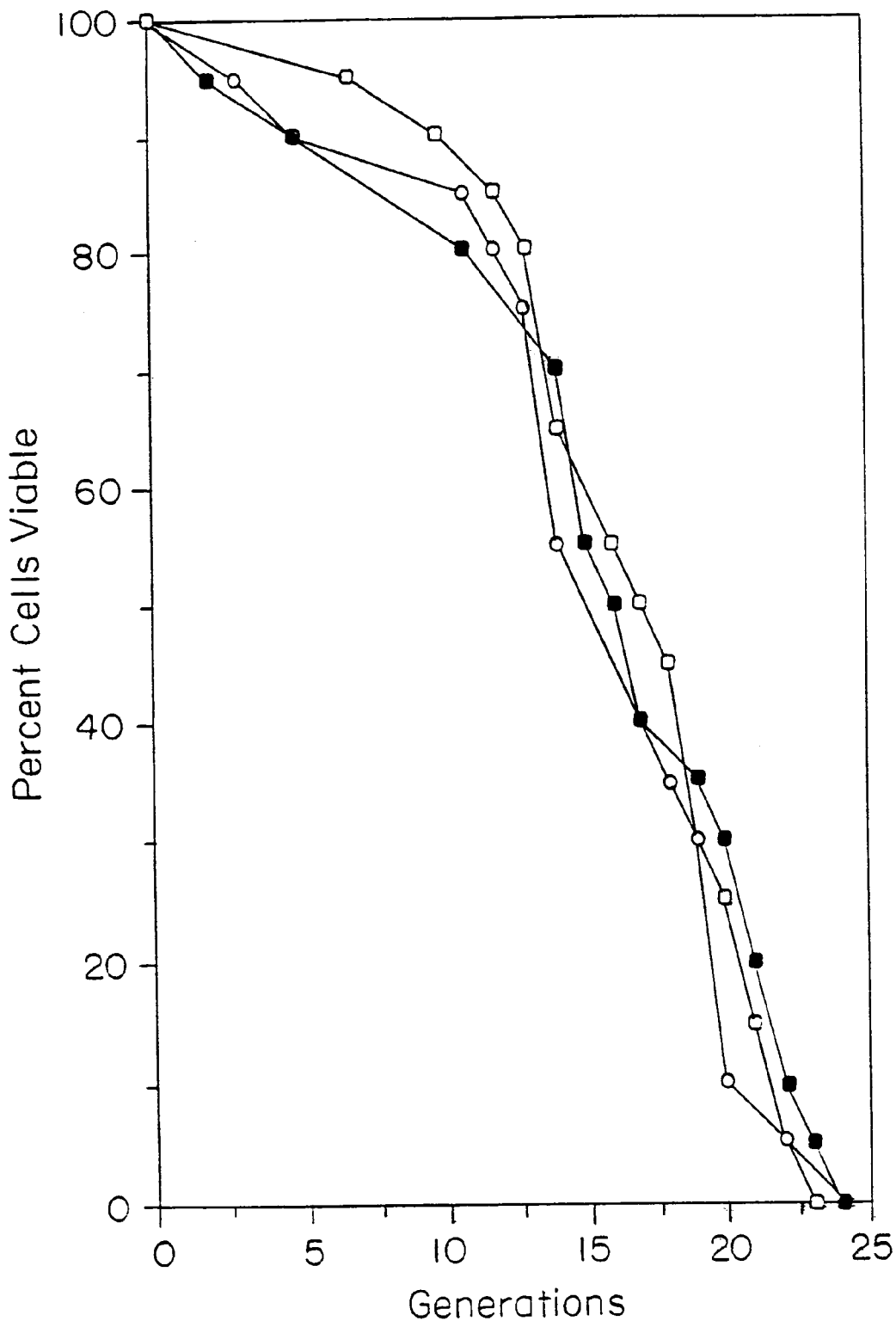
FIG. 9 is a graphic representation of the life span of 14c (open squares), 14c with a disruption in the STE4 gene (closed squares), and 14c with a disruption in the STE12 gene (open circles).

Further, sterility per se was not the cause of the longer life span. Disrupting STE4 or STE12, genes involved in aspects of mating different than those of SIR4, did not affect life span (see FIG. 9). The disruption of STE4 was carried out as described in Whiteway, M. et al., *Cell* 56:467–477 (1989).

In addition, introduction of a plasmid which expressed MATα into BKy5 did not lengthen life span. The effects of sterility on life span are shown in Table 1, below. The maximum life span indicates the number of daughters produced by the oldest mother cell.

TABLE 1

The Effects of Sterility on Mean Life Span

| Strain | Sample Size | Mean Life Span | Maximum Life Span |
| --- | --- | --- | --- |
| BKy1–14c | 20 | 15.6 | 25 |
| BKy5 | 20 | 14.5 | 20 |
| BKy6 | 20 | 15.3 | 27 |
| BKy100 (ste4Δ) | 20 | 15.9 | 24 |
| BKy101 (ste12Δ) | 20 | 16.5 | 24 |
| BKy5 + Matα | 20 | 14.6 | 26 |

Figure 10:
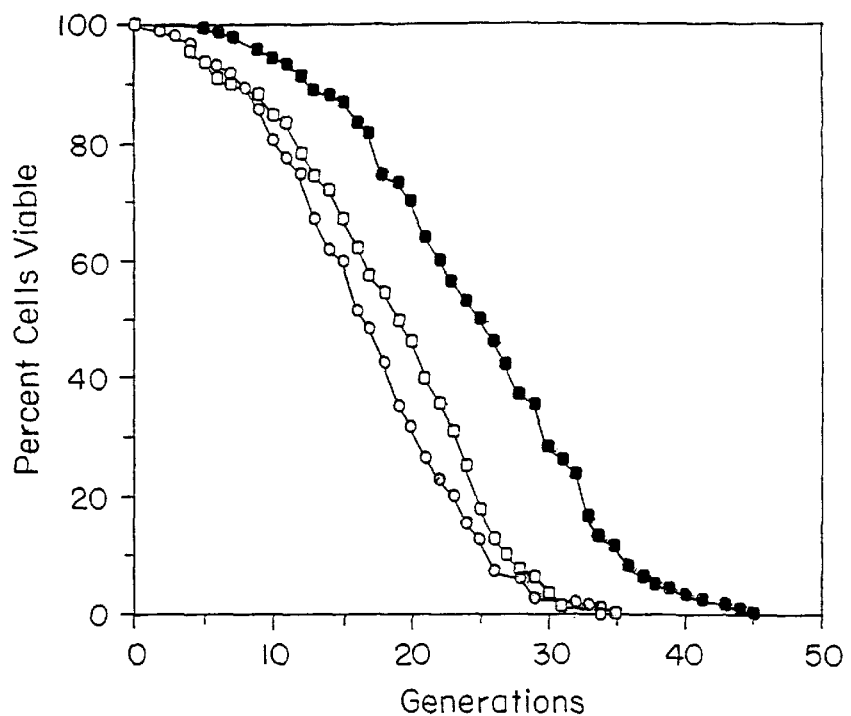
FIG. 10 is a graphic representation of mortality curves for 14c (SIR4, open squares), sir4-42 (closed squares), and BKy104 (sir4, open circles). Sample sizes were 139 cells (14c), 139 cells (sir4-42), and 136 cells (BKy104).

Because the stress and mating phenotypes of sir4-42 were recessive, it was surmised that the phenotype of a SIR4 null mutation would mimic that of sir4-42. The entire SIR4 gene was deleted in 14c: the region from 153 base pairs 5' to SIR4 through the entire open reading frame was deleted and replaced with the URA3 gene using the plasmid pAR59 provided by J. Broach (Marshall, M. et al., *Mol. Cell. Biol.* 7:4441–4452 (1987)). The sir4 deletion was confirmed by southern analysis. The resultant deleted strain, BKy104, was indeed stress tolerant and sterile (data not shown). Importantly, however, it did not have a lengthened life span; in fact, the deletion shortened life span by a small, but statistically significant, degree (see FIG. 10).

Figure 11:
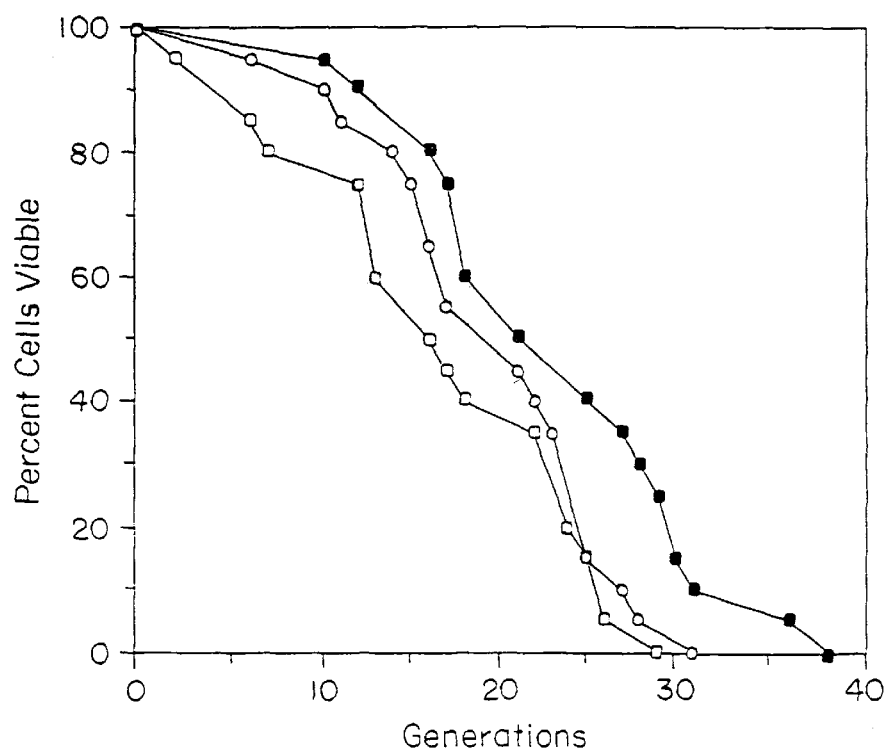
FIG. 11 is a graphic representation of mortality curves for 14c (SIR4, open squares), sir4-42 (sir4, closed squares), and BKy109 (sir4-42+SIR4, open circles). Sample sizes were 20 cells for all strains.

These data suggested that the effect of sir4-42 on life span, unlike its effects on stress and mating, might be due to a gain of function. To test this, it was investigated whether the sir4-42 allele was dominant to SIR4 for the phenotype of lengthened life span. The wild type SIR4 was transferred to an integrating vector and targeted to URA3 in the sir4-42 mutant. The integration plasmids were generated by subcloning the entire library insert containing SIR4 from pBK40 into pRS305 or pRS306 by a NotI SalI double digest (Sikorski, R. S. and P. Hieter, *Genetics* 122:19–27 (1989)). Integration was directed to the URA3 locus by a StuI digest, and was verified by Southern analysis. The resulting SIR4-sir4-42 haploid (BKy109) was stress sensitive and mated efficiently, as expected. However, the life span of this strain was intermediate between the SIR4 parent, 14c, and the sir4-42 mutant, as shown in FIG. 11. Statistical analysis determined that the mean life span of BKy109 was significantly different from the means of both sir4-42 and 14c. The sir4-42 mutation therefore is semi-dominant with respect to life span.

As a second test for dominance, mating was used to construct isogenic diploids, SIR4/SIR4 (BKy6), SIR4/sir4-42 (BKy17), and sir4-42/sir4-42 (BKy28) (using the SIR4 plasmid, pBK40, to permit mating in sir4-42 mutants). BKy19 was generating by mating the sir4-42 mutant containing pBK40 to 14c and subsequently removing the plasmid with 5-FOA. BKy17 was sporulated and a MATa sir4-42 segregant (BKy21) was used to generate the homozygous sir4-42 diploid (BKy28). BKy21 carrying pBK40 was mated to the sir4-42 mutant also carrying pBK40 and diploids were isolated. The homozygous diploids have life spans similar to their haploid parents, and the heterozygous diploid displayed a life span intermediate between the homozygotes (data not shown). These findings clearly show that the extended life span in the sir4-42 mutant is semi-dominant, and therefore, due to a gain of function mutation.

Gap repair was utilized to clone both the wild type SIR4 allele from 14c and the sir4-42 allele from the SIR4 mutant strain (Guthrie, C. and G. Fink, *Methods in Enzymology*, 1991). A SmaI AatII double digest was performed to remove the coding region of SIR4 from pBK40. The linear plasmid was gel purified and transformed into either 14c or the sir4-42 mutant. Ura+ colonies were picked and the plasmids were recovered by standard methods. Restriction digests were conducted to determine if the gap repair event was successful. To localize the mutation within SIR4, digests were conducted with AatII, SmaI, and SphI, all of which have one site in the SIR4 gene and another within the pBK40 insert, either 5' or 3' to SIR4. These linearized plasmids were transformed into sir4-42 and transformants were tested for their ability to complement the sir4-42-associated mating defect. This analysis localized the mutation to the region spanning codons 743 to the UAA stop at the end of the 1358 residue SIR4 open reading frame. The clone was shown to contain the mutation by a functional test in which it was transferred to an integrating vector, and targeted to LEU2 in strain BKy104 (Δsir4). Integration was directed to the LEU2 locus by a XcmI digest, and verified by Southern analysis. The resulting strain had an extended life span, indicating that the integrating vector contained the sir4-42 allele (data not shown). The SmaI fragments from the mutant or wild type SIR4 gene, which contained the region spanning 743 to the UAA stop at the end of the 1358 residue SIR4 open reading frame, were subcloned into Bluescript (Stratagene). Sequencing primers were made approximately 200 base pairs apart for this entire region, and it was sequenced by the single-strand approach (Sequenase version 2, U.S. Biochemicals). A single difference was found in the mutant which generated a stop codon at amino acid 1237 of the encoded protein, removing 121 residues from the SIR4 gene product.

Figure 15A:
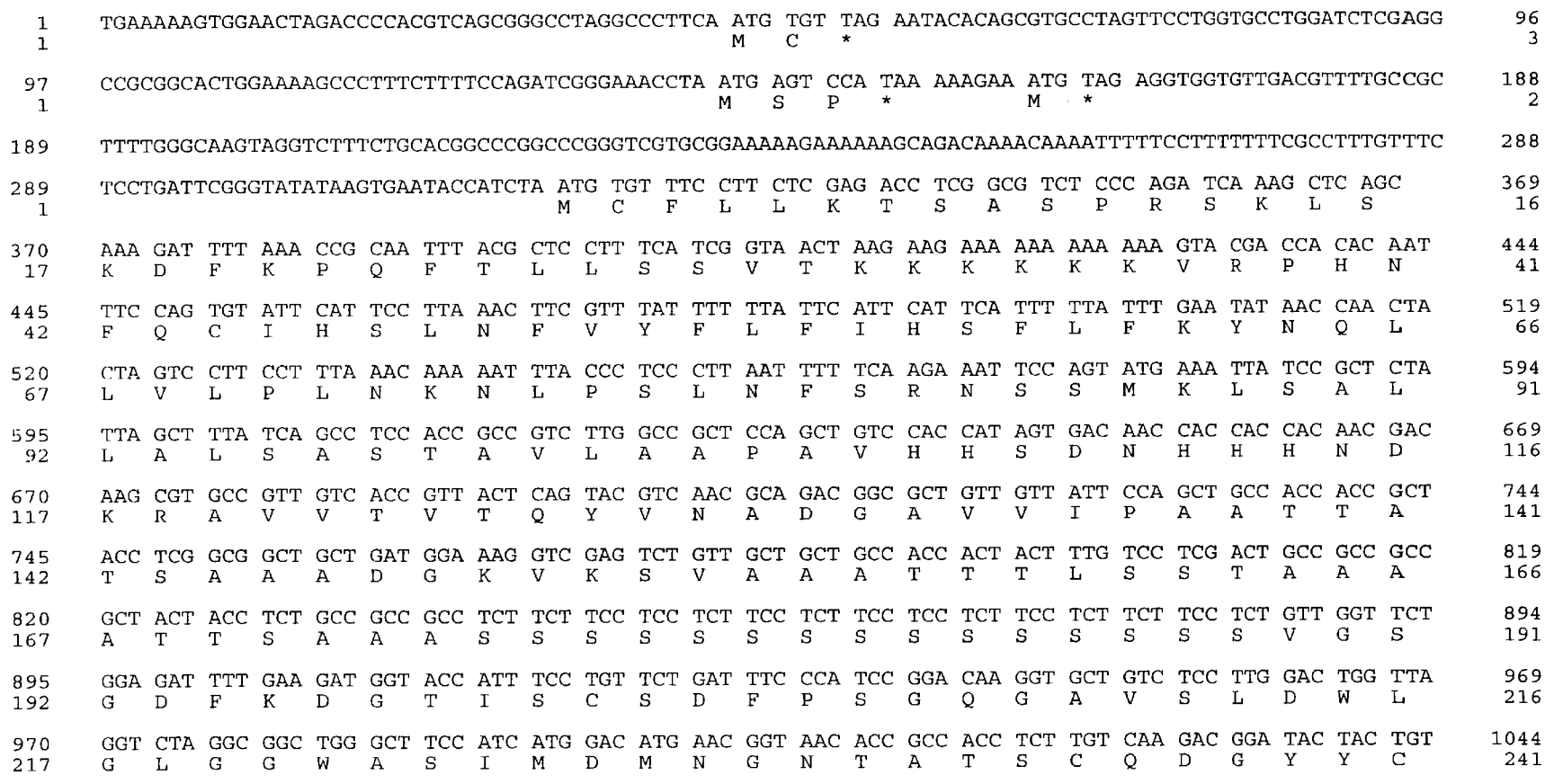
Figure 15B:
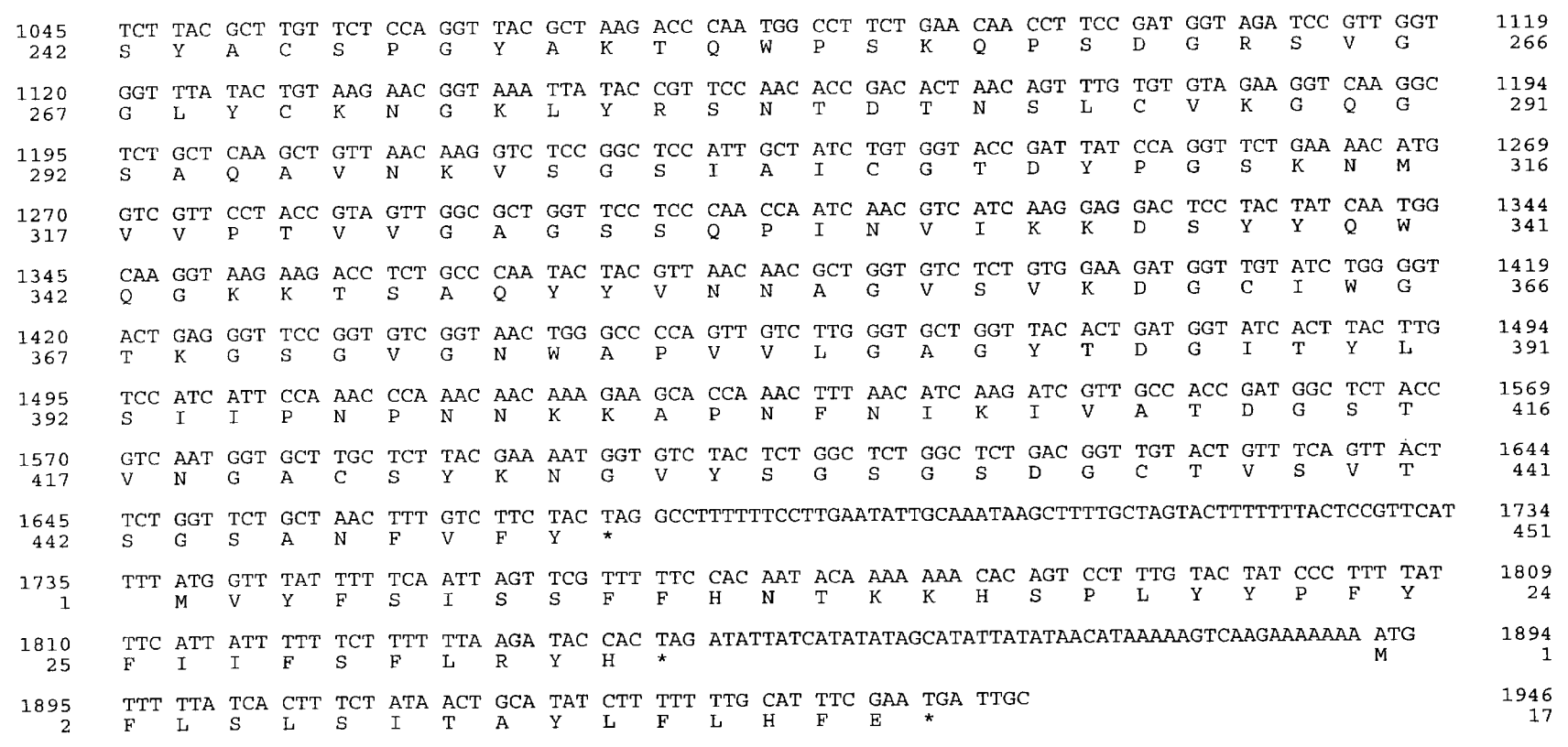

A second gene involved in senescence in yeast, corresponding to UTH1 described above, has been identified. The UTH1 mutation, described above, rendered 14c sensitive to paraquat. The UTH1 gene was cloned from the CT3 library by its ability to confer resistance to paraquat. The sequence was obtained using standard methods. The nucleic acid sequence (SEQ ID NO. 1), and the encoded amino acid sequence (SEQ ID NO. 2), are shown in FIG. 15.

Figure 20A:
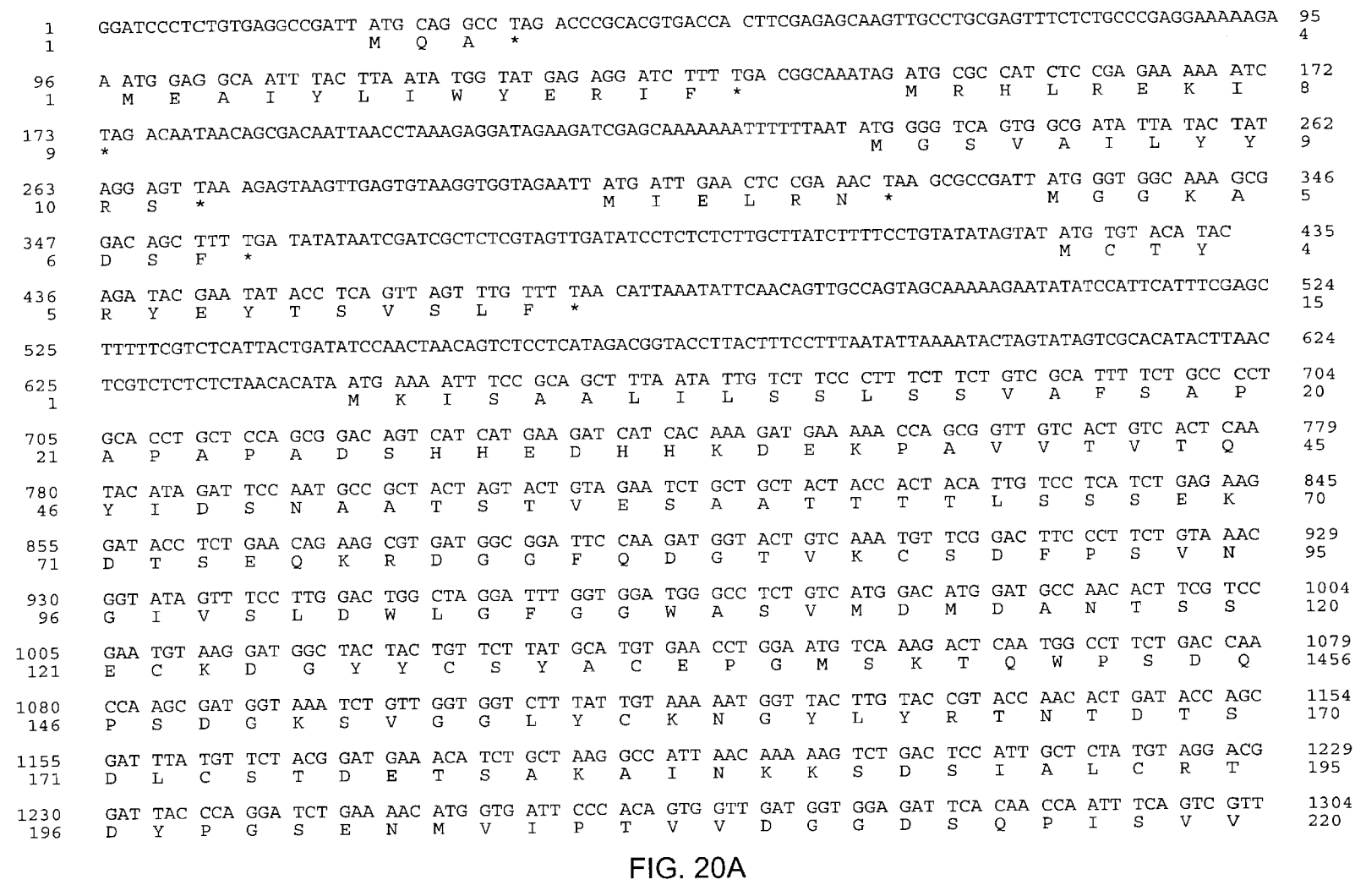
Figure 21A:
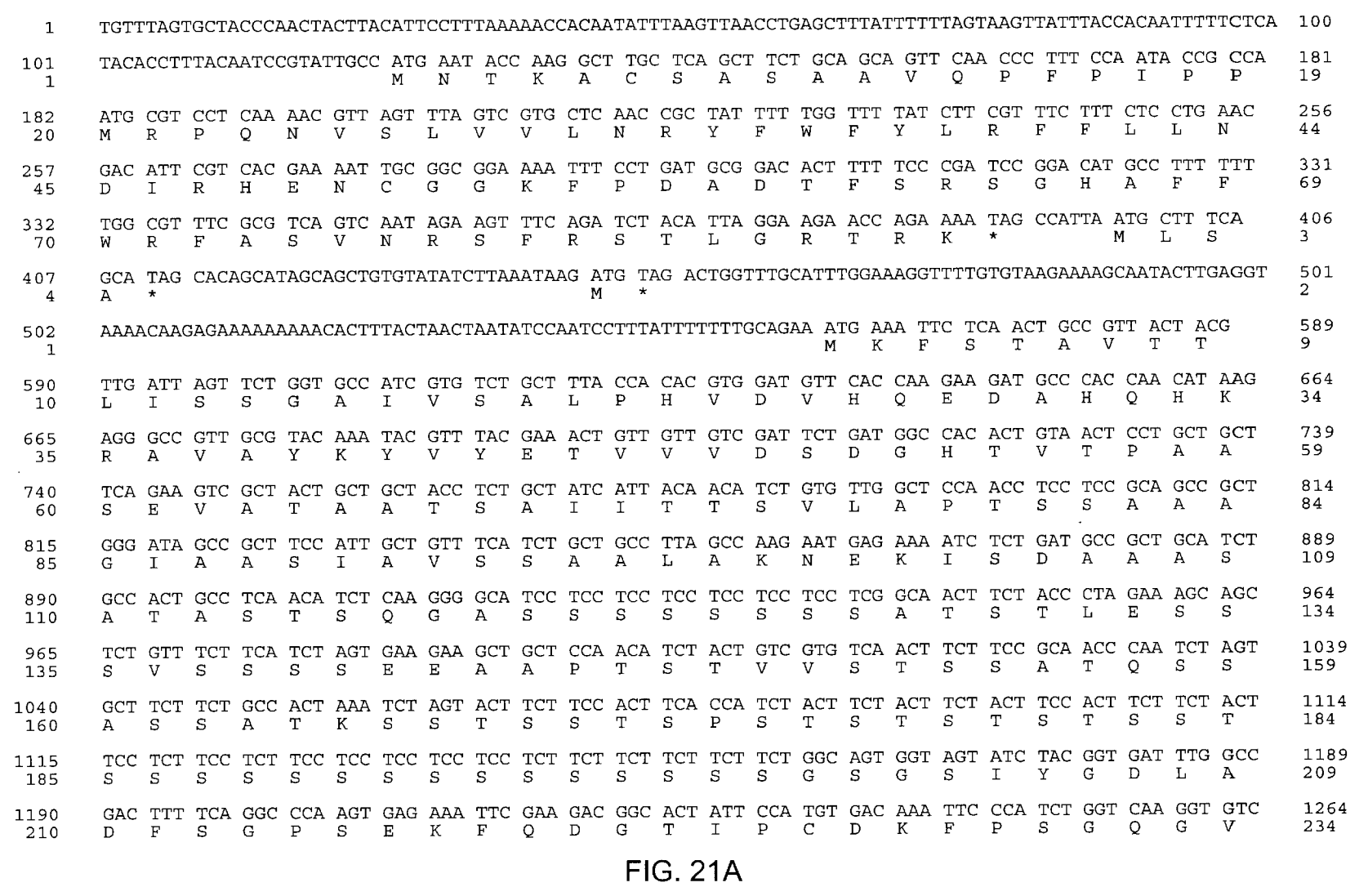
Figure 21B:
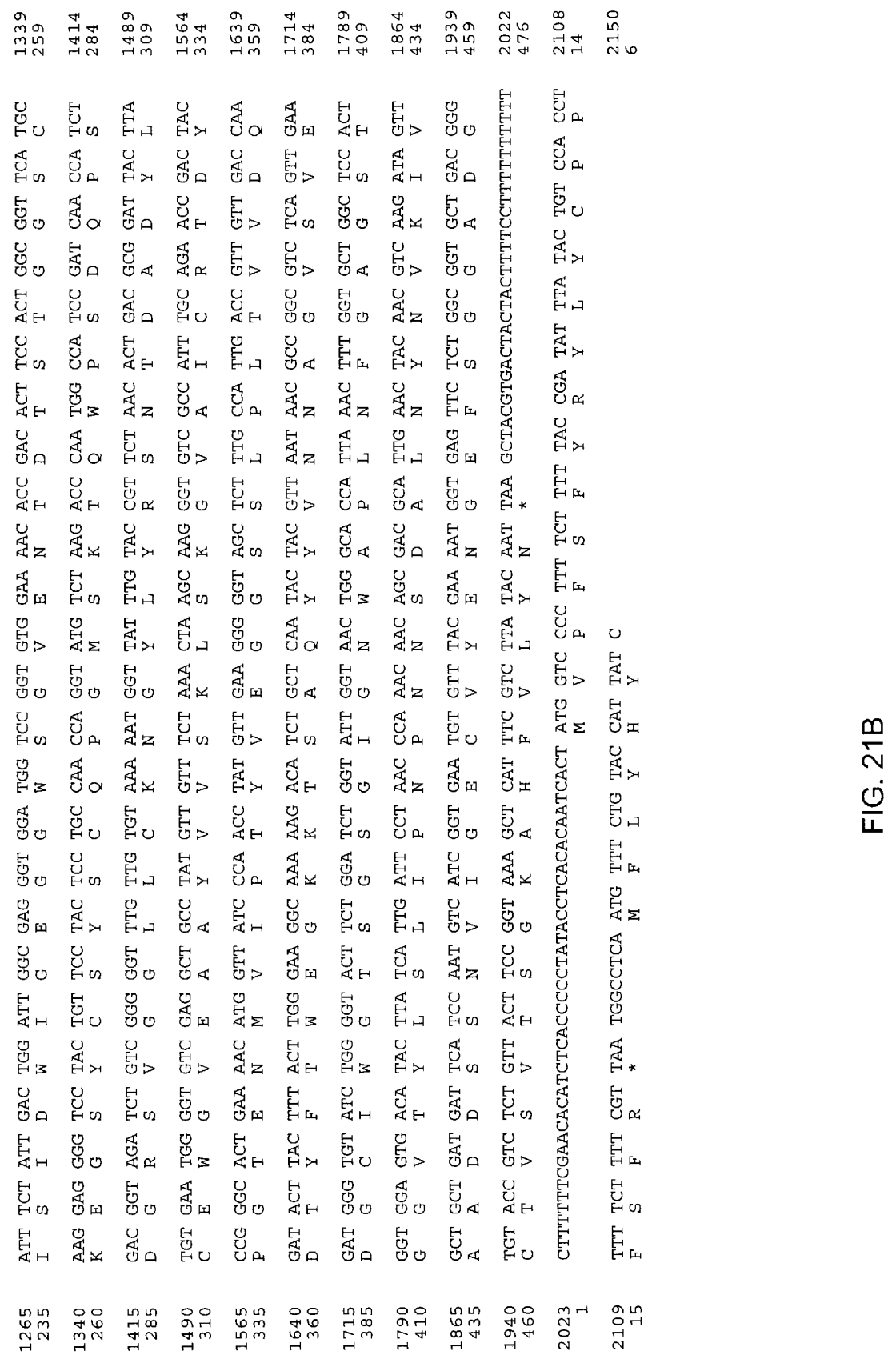

Furthermore, two additional *S. cerevisiae* genes, NCA3 (SEQ ID NO. 11, FIGS. 20A–B) and SAG1 (SEQ ID NO. 13, FIGS. 21A–B), which show a strong homology to UTH1 across a region referred to herein as the SUN domain, have been identified by screening a computerized database with the UTH1 sequence. A comparison of the sequences of the three genes reveals that they show 61 percent identitiy across the SUN domains (FIGS. 22A–B). The SUN domain of the UTH1 gene extends from nucleotide 236 to nucleotide 451, the SUN domain of the NCA3 gene extends from nucleotide 123 to nucleotide 338, and the SAG1 SUN domain extends from nucleotide 211 to nucleotide 426. The SUN domains are the regions of the genes which show the greatest homology. A partial sequence of a third gene with homology to UTH1, designated SUN4 (SEQ ID NO. 15), has also been identified. Deletion of either the NCA3 gene or the SAG1 gene results in a shortened life span compared with the wild-type yeast strain, indicating that these genes contribute to extended life span. This suggests that senescence may be controlled by a family of proteins which interact to regulate aging.

A third gene involved in senescence in yeast, corresponding to UTH4 described above, has been identified and the nucleic acid sequence (SEQ ID NO. 3) and encoded amino acid sequence (SEQ ID NO. 4) are shown in FIGS. 16A–E. A partial sequence (nucleotides 3–108) of the UTH4 gene was obtained from transformed yeast cells, and a database search revealed the identity and sequence of the complete UTH4 gene. UTH4 contains eight "repeat" boxes which comprise approximately one-third of the gene sequence. A comparison of the eight boxes at the amino acid level reveals that they are about fifty percent homologous (FIG. 23). More striking, however, is a comparison of the UTH4 repeating-box sequence with similar box sequences of several other genes, identified in various databases as having regions of homology with the repeating region of UTH4, including the yeast YGL023 gene (Chen et al., *Yeast* 7:309–312 (1991), SEQ ID NO. 5, FIGS. 17A–E), the human D43951 gene (SEQ ID NO. 7, FIGS. 18A–G), the human D13645 gene (SEQ ID NO. 9, FIGS. 19A–C) and the Drosophila PUMILIO gene (Barker et al., *Genes and Development*, 6:2313–2326 (1992). A computer database search revealed that each of these genes contains a similar eight-box region, and a comparison of the YGL023, D93451, PUMILIO and UTH4 genes across this region indicates a conservation of greater than fifty percent (FIG. 24).

UTH4 appears to be similar to SIR4 in that deletion of the entire gene does not confer extended life span upon *S. cerevisiae*. However, a specific mutation of the UTH4 gene results in an increased life span in the yeast compared with wild-type life span. This mutation can be a single nucleotide change which results in either an amino acid change or generation of a stop codon resulting in a truncated protein.

The Lengthening of Life Span by sir4-42 Requires SIR3

Figure 12:
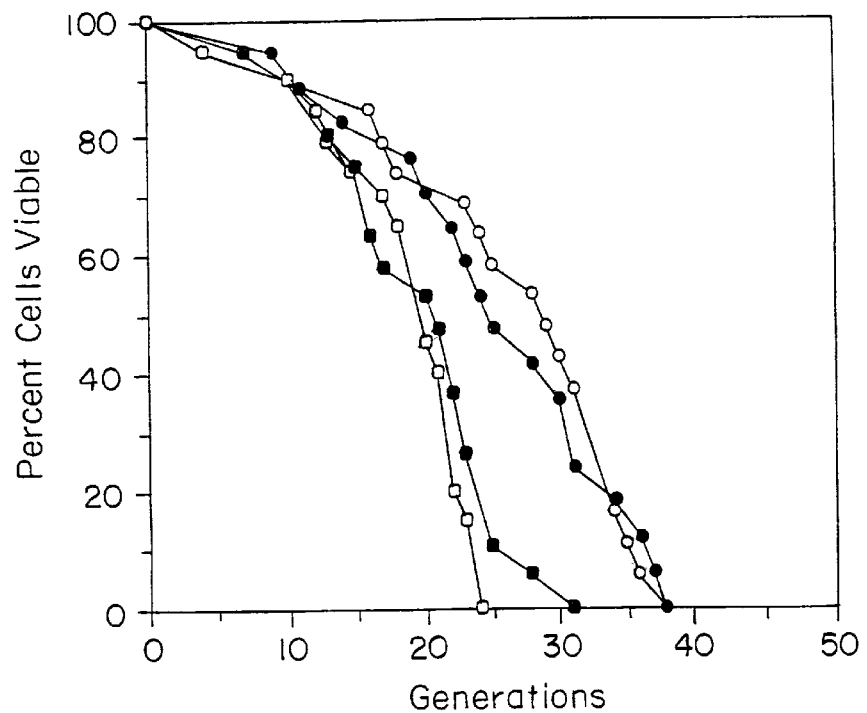
FIG. 12 is a graphic representation of mortality curves for 14c (SIR4, open squares), sir4-42 (closed circles), and the isogenic deletion in sir1 derivatives (sir4-42 Δsir1, open circles; SIR4 Δsir1, closed squares). Sample sizes were 20 cells (14c), 19 cells (SIR4 Δsir1), 18 cells (sir4-42), and 19 cells (sir4-42 Δsir1).
Figure 13:
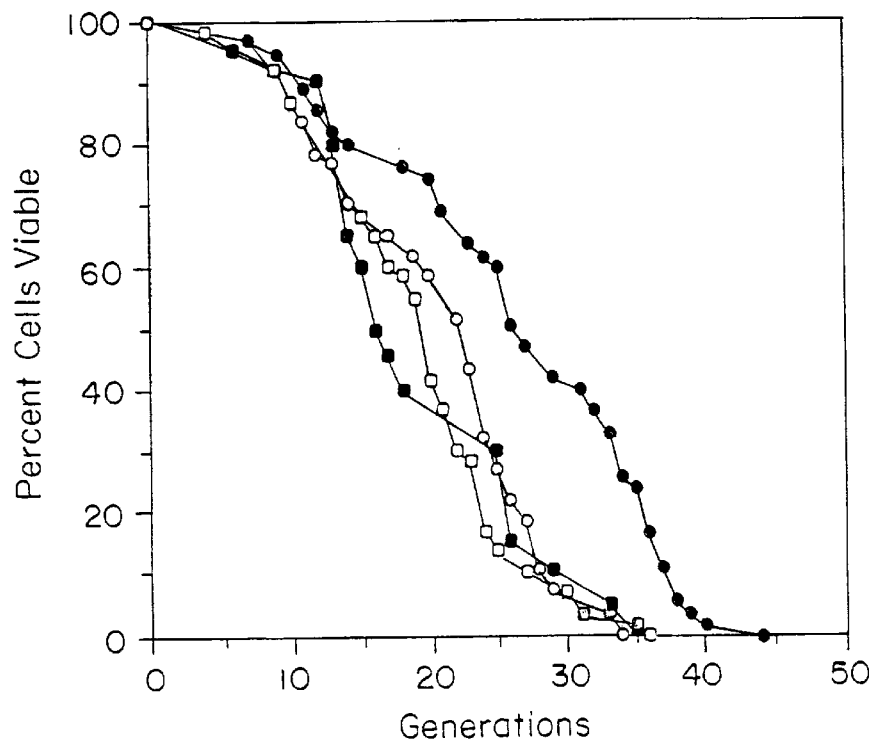
FIG. 13 is a graphic representation of mortality curves for 14c (SIR4, open squares), sir4-42 (closed squares), and the isogenic deletion in sir3 derivatives (sir4-42 Δsir3, open circles; SIR4 Δsir3, closed diamonds). Sample sizes were 60 cells (14c), 20 cells (SIR4 Δsir1), 19 cells (sir4-42), and 30 cells (sir4-42 Δsir1).

It was investigated whether sir4-42 acted alone or in concert with other members of the SIR complex. The activities of SIR2, SIR3, and SIR4 are closely coupled in that all are required for silencing at the HM loci and at telomeres (Aparicio, O. M. et al., *Cell* 66(6):1279–1287 (1991); Rine, J. and Herskowitz, I., *Genetics* 116:9–22 (1987)). The function of SIR1 is different in that it is only required at the HM loci (Aparicio, O. M. et al., *Cell* 66(6):1279–1287 (1991)), and even there, its requirement is not absolute (Pillus, L. and J. Rine, *Cell* 59:637–647 (1989)). To determine whether SIR3 and SIR1 were required for the extension of life span, the genes were disrupted in the sir4-42 mutant, and, as a control, in 14c. The sir1 deletion was generated using plasmid pJI23.2 which removes the C-terminal 335 amino acids from the 648 amino acid protein (Ivy, J. M. et al., *Mol. Cell.Biol.* 6:688–702 (1986)). The sir3 deletion was constructed by deleting 123 amino acids at the C-terminus of SIR3. The sir1 disruptions did not exert any effect on the sir4-42 mutant or its SIR4 parent (FIG. 12). In contrast, the sir3 disruption abolished the extension of life span conferred by sir4-42 (FIG. 13). This shortening of life span in the sir4-42 strain was specific because disruption of SIR3 did not alter the life span of the SIR4 parent (FIG. 13). Thus, the gain of function caused by sir4-42 appears to be an activity of the entire SIR complex, and not SIR4 alone.

Effects of the sir4-42 Mutation on Telomeres

Because the sir4-42 mutation results in a loss of activity at HM loci, it is possible that the mutation redirects the SIR complex to another chromosomal location, resulting in the observed extension in life span. One obvious possible location was telomeres, because loss of function mutations in SIR2, SIR3, or SIR4 relieve silencing at telomeres and also result in shorter telomeres (Aparicio, O. M. et al., *Cell* 66(6):1279–1287 (1991); Palladino, F. et al., *Cell* 75:543–555 (1993)). In mammalian cells, telomeres have been shown to shorten with age (Harley, C. B. et al., *Nature* 345:458–460 (1990)), and this shortening has been proposed as a causative agent of aging (Allsopp, R. C. et al., *PNAS USA* 89:10114–10118 (1992); Olovnikov, A. M. *J. Theor. Biol.* 41:181–190 (1973)). If telomere shortening imposed a limit to life span, then excessive recruitment of SIR complex might counter aging by lengthening telomeres. Therefore, the length of telomeres in 14c and its Δsir4 and sir4-42 mutant derivatives was determined. Total genomic DNA was isolated, digested with XhoI, and separated on a 0.7% agarose gel and transferred to a GeneScreen Plus Hybridization Transfer Membrane (NEN Research Products). Hybridization and wash conditions were as suggested by the manufacturer. A plasmid containing 600 base pairs located within the conserved Y' region of yeast telomeres, supplied by V. Zakian, was nick translated (GIBCO BRL) and used as a probe (Chan, C. S. M. and B. K. Tye, *Cell* 33:563–573 (1983)). This probe overlapped the XhoI site and thus hybridized to fragments both telomere-proximal and telomere-distal to the restriction site. Most yeast telomeres contain the Y' region (Walmsley, R. M. et al., *Nature* 310:157–160 (1984)). Deletion of SIR4 resulted in a shortening of telomeres by approximately 50–100 bases (Palladino, F. et al., *Cell* 75:543–555 (1993)). Surprisingly, the length of telomeres in the sir4-42 mutant was indistinguishable from the Δsir4 mutant, indicating that the mutant behaved like the deletion with respect to activity at telomeres. Separate experiments confirmed that silencing at telomeres was also alleviated in the sir4-42 mutant just as in the Δsir4 strain (data not shown). Thus, the sir4-42 exhibits a loss of function phenotype. However, because sir4-42 extends life span and Δsir4 does not, the lengthened life span is probably unrelated to telomere length or silencing.

Expression of the Carboxyl-terminus of SIR4 Extends Life Span

Figure 14:
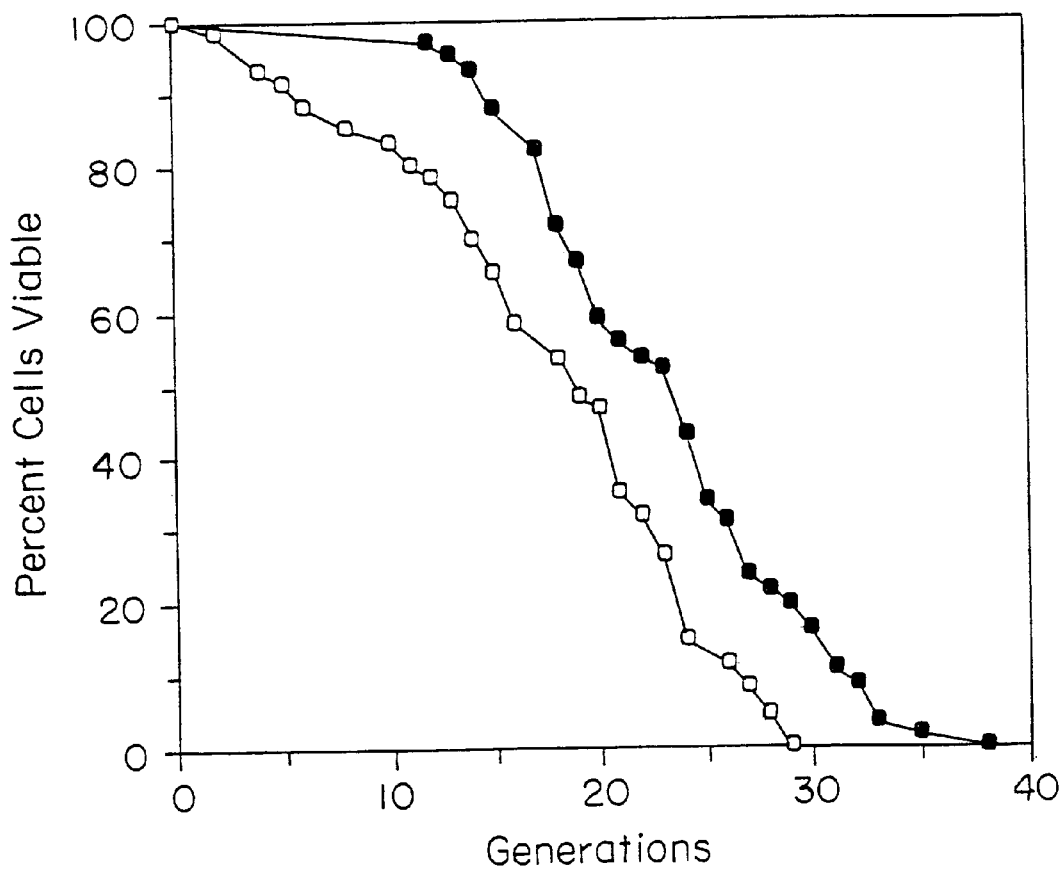
FIG. 14 is a graphic representation of the mortality curves for 14c (SIR4, open squares) and SIR4 plus anti-SIR4 (closed squares). Sample sizes were 50 cells (14c) and 46 cells. (SIR4+Anti-SIR4).

Since the sir4-42 mutation removes the carboxyl-terminus of the protein, it is possible that this fragment of SIR4 localized the complex to HM loci and telomeres. Thus, overexpression of a carboxyl-terminal fragment of SIR4 might compete with the wild type protein for recruitment to HM loci and telomeres. A construct expressing only the carboxyl 154 residues of SIR4 has been shown to behave as an anti-SIR4 dominant negative mutant. with respect to silencing at HM loci (Ivy, J. M. et al., *Mol. Cell.Biol.* 6:688–702 (1986); Marshall, M. et al., *Mol. Cell. Biol.* 7:4441–4452 (1987)). Therefore, a construct that expresses the carboxyl-terminal region of SIR4 (Ivy, J. et al., *Mol. Cell Biol.* 6:688–702 (1986)) was used to antagonize the native SIR4 protein and render cells sir4-. Transformation of this construct into 14c confirmed that it functioned as a dominant negative inhibitor of mating. The transformant was also stress resistant, as expected. Strikingly, the construct also extended the life span by about 30% (see FIG. 14). The strain labeled SIR4+Anti-SIR4 is 14c transformed with the plasmid pJH3A, a 2 μ plasmid containing the C-terminal 154 amino acids of the SIR4 gene (Ivy, J. et al., *Mol. Cell Biol.* 6:688–702 (1986)).

Summary of Yeast Strains Described Above

Table 2 depicts the strain and genotype of all yeast strains described herein. All strains were generated in this study except BWG1-7A which is described in Guarente, L. and T. Mason, *Cell* 32:1279–1286 (1983)), and the mating testers CKy20 and CKy21 which were gifts of C. Kaiser. The terminology LEU2/sir4-42 in the strain BKy107 means the sir4-42 allele has been integrated at the LEU2 locus, for example.

TABLE 2

Yeast Strains Used in this Study

| Strain | Genotype |
|---|---|
| BWG1-7A | Mata ade1-100 his4-519leu2-3,2-112 ura3-52 |
| PSY142 | Matα leu2-3,2-112lys2-801 ura3-52 |
| BKy1 | Mata  ade1-100  his4-519  leu2-3,2-112  LYS2      ura3-52 |
|  | Matα  ADE          HIS4      leu2-3,2-112  lys2-801  ura3-52 |
| BKy1-14a | Mata ade1-100 leu2-3,2-112 lys2-801 ura-3-52 |
| BKy1-14b | Matα leu2-3,2-112 ura3-52 |
| BKy1-14c | Matα ade1-100 his4-519 leu2-3,2-112 lys2-801 ura3-52 |
| BKy1-14d | Mata his4-519 leu2-3,2-112 ura3-52 |
| BKy5 | Mata ade1-100 his4-519 leu2-3,2-112 lys2-801 ura3-52 |
| BKy6 | Mata  ade1-100 his4-519 leu2-3,2-112 lvs2-801 ura3-52 |
|  | Matα ade1-100 his4-519 leu2-3,2-112 lys2-801 ura3-52 |
| BKy17 | Mata  ade1-100 his4-519 leu2-3,2-112 lys2-801 ura3-52 SIR4 |
|  | Matα ade1-100 his4-519 leu2-3,2-112 lys2-801 ura3-52 sir4-42 |
| BKy21 | Mata ade1-100 his4-519 leu2-3,2-112 lys2-801 ura3-52 sir4-42 |
| BKy28 | Mata  ade1-100 his4-519 leu2-3,2-112 lys2-801 ura3-52 sir4-42 |
|  | Matα ade1-100 his4-519 leu2-3,2-112 lys2-801 ura3-52 sir4-42 |
| BKy30 | Mata ade1-100 his4-519 leu2-3,2-112 lys2-801 ura 3-52 SIR4/LEU2 |
| Bky100 | Matα ade1-100 his4-519 leu2-3,2-112 lys2-801 ura3-52 Ste4::URA3 |
| BKy101 | Matα ade1-100 his4-519 leu2-3,2-112 lys2-801 ura3-52 ste12::URA3 |
| BKy102 | Matα ade1-100 his4-519 leu2-3,2-112 lys2-801 ura3-52 sir1::LEU2 |
| BKy103 | Matα ade1-100 his4-519 leu2-3,2-112 lys2-801 ura3-52 sir3::URA3 |
| BKy104 | Matα ade1-100 his4-519 leu2-3,2-112 lys2-801 ura3-52 sir4::URA3 |
| BKY105 | Matα ade1-100 his4-519 leu2-3,2-112 lys2-801 ura3-52 sir4-42 sir1::LEU2 |
| BKy106 | Matα ade1-100 his4-519 leu2-3,2-112 lys2-801 ura3-52 sir4-42 sir3::URA3 |
| Bky107 | Matα ade1-100 his4-519 lys2-801 ura3-52 sir4::URA3 LEU2/sir4-42 |
| BKy108 | Matα ade1-100 his4-519 leu2-3,2-112 ly2-801 sir4-42 URA3/SIR4 |
| CKy20 | Matα arg1 tsm11 |
| CKy21 | Mata arg1 tsm11 |

Framework for Relating Silencing, Aging, Stress, and Telomeres

Table 3 summarizes the effects of three mutant alleles of SIR4 that alleviate silencing and also promote stress resistance.

TABLE 3

Phenotypes of SIR4 Alleles

| Allele | Amino Acids | Mating | Stress Resistance | % Life Span Increase |
|---|---|---|---|---|
| SIR4 | 1–1358 | + | Sensitive | — |
| sir4–42 | 1–1237 | – | Resistant | 30–60% |
| sir4Δ | — | – | Resistant | none |
| SIR4 + Anti-SIR4 | 1–1358 + 1205–1358 | – | Resistant | 20–45% |

Deletion of SIR3 has effects indistinguishable from deletion of SIR4 (data not shown). Of all of these mutations, however, only sir4-42 extends life span. To explain these findings, it is proposed that a locus that is repressed by the SIR complex can promote resistance to stress when repression is eliminated. In principle, this locus could be linked to HML, HMR, a telomere, or reside at some other location. Linkage to HM loci is not plausible, however, because deletion of SIR1, which weakens repression at the HM loci, does not promote stress resistance. For simplicity, it is suggested that there is a telomere-linked, stress-resistant locus under SIR control.

It is further suggested that the lengthening of life span is due to a different locus, termed AGE, that is independent of effects at HM loci or telomeres. The repression of the "AGE" locus by SIR4 is essential to longevity, according to this view, and aging may result from a breakdown in the silencing of that locus. It is, of course, possible that silencing at more than one chromosomal region governs aging. In any case, the "AGE" locus is proposed to be unlinked to telomeres or HM loci because both the sir4-42 mutation and the Δsir4 eliminate silencing at HM loci and at telomeres, but only the sir4-42 allele extends life span. Further, the extension of life span by sir4-42 is semi-dominant in a strain also containing SIR4, indicating that it is a gain of function mutation with regard to life span. The function gained in the mutant must relate to the normal silencing activity of the SIR complex because the ability of sir4-42 to promote longevity requires the integrity of SIR3.

It is also suggested that the sir4-42 mutation prevents recruitment of the SIR complex to HML, HMR, and telomeres, rendering the complex more available for any other site of action in the cell. The carboxyl 121 residues that are missing in the sir4-42 mutant may be important in the recruitment of the SIR complex to these chromosomal sites. Consistent with the view that the carboxyl terminus of SIR4 helps localize the SIRs to HM loci and telomeres, overexpression of the carboxyl 163 residues of SIR4 is known to exert a dominant negative effect on repression at HM loci (Ivy, J. et al., *Mol. Cell Biol.* 6:688–702 (1986); Marshall, M. et al., *Mol. Cell. Biol.* 7:4441–4452 (1987)). Expression of this SIR4 fragment, in addition to blocking repression at HML and HMR, promoted longevity.

A breakdown in silencing by the SIR complex may be causally related to aging in *S. cerevisiae*. The identification of SIR4 as a gene that affects life span in yeast thus appears to relate telomeres and aging. However, as described above, telomeres in the sir4-42 strain, just as in the Δsir4 null mutant, are shorter than wild type. This suggests that telomere length is not causally related to aging. Nevertheless, it is theoretically possible that the mutation counters telomere shortening selectively in old cells.

Methods of Isolating Strains with Increased Life Span

The techniques described above can be used to isolate other yeast strains with increased life spans, and thereby to isolate other genes, from yeast and other cell types (e.g. vertebrate, mammalian) involved in senescence. Any budding yeast strain for which the life span is known can be utilized. The life span of the strain can be determined by calculating the mean number of generations before senescence in a sample of colonies of the strain of interest. A sample of the strain of interest is exposed to a mutagen, such as ethylmethane sulfonate (EMS), N-methyl-N'-nitro-N-nitrosoguanidine (MNNG), or ultraviolet irradiation. Mutants with increased life spans can then be isolated as follows.

Starvation-resistance method Yeast cells that have been exposed to mutagen are plated with minimal nutrients (including carbon and nitrogen sources, as well as the amino acids and nucleotides that are required by the particular strain for growth). The minimal plates are replica-plated to plates lacking vital nutrients, such as nitrogen and carbon (the starvation plates). After incubation of the starvation plates at a temperature appropriate for growth, for several days, the starvation plates are replicated back to rich media plates. The rare colonies containing living cells when plated back onto rich medium (the "starvation resistant" colonies) are then examined to determine whether the life span is extended. Life span is calculated as described above. This method is particularly appropriate for short-lived strains, which are more sensitive to starvation.

Cell surface labelling method This method takes advantage of the fact that the cell surface (including the cell membrane and cell wall) of a daughter cell in some budding yeast, such as *S. cerevisiae*, is fabricated entirely of new materials: when the cell surface of the mother cell is labelled, the surface of the daughter cells remains unlabelled. In one embodiment, the cell surface is labelled with biotin. When avidin linked to fluorescence is coupled to the biotin, the cell surface fluoresces. Alternatively, any other method of labelling the cell surface with a fluorescent marker is appropriate. Daughter cells remain unlabelled (will not fluoresce). Fluorescently labelled yeast cells are plated and cultured for a period of time greater than the life span of the non-mutant strain (as measured by time necessary for one cell division, multiplied by the number of divisions, or generations, in the life span). If desired, the yeast cells may be sampled at regular time intervals in order to monitor the plating efficiency of the cells; the efficiency will drop precipitously after the chronological life span has passed. The yeast cells are then subjected to fluorescence-activated cell sorting (FACS), to isolate the fluorescently labelled cells. The fluorescent cells are then replated; only mutants with increased life spans will grow.

Temperature-sensitive method A temperature-sensitive mutant strain, in which the daughter cells die at the non-permissive temperature, is utilized. For example, yeast cells with a mutation in the mdm2-2 gene (also known as the ole-1 gene) (McConnell, S. et al., *J. Cell Biol.* 111:967–976 (1990)) bud forth living daughter cells at 30° C., but not at 37° C., because of a failure in appropriate organelle segregation at the higher temperature (mitochondria are not put into daughter cells). In such a temperature-sensitive mutant, the daughter cells bud off from the mother cell and die at the non-permissive temperature; the dead daughter cells remain near the mother cell. Therefore, each mother cell grown at the non-permissive temperature generates a microcolony of N cells, where N is equal to the number of generations in the life span of the mother cell. Mutant strains will display microcolonies wherein the number of cells is greater than N.

To isolate mutants, cells are plated at the permissive temperature. A sample of cells from each colony is then transferred to a plate to be grown at the non-permissive temperature. Microcolonies with cell number greater than N are indicative of mutants; cells from the colonies which have been identified as mutant can be selected from the plates grown at the permissive temperature. Alternatively, cells are plated directly at the non-permissive temperature, and grown for a period of time greater than the life span as measured by time necessary for one cell division, multiplied by the number of divisions, or generations, in the life span. If desired, the yeast cells may be sampled at regular time intervals in order to monitor the plating efficiency of the cells; the efficiency will drop precipitously after the chronological life span has passed. After this time, the plates are shifted back to the permissive temperature. Only longer-lived mutants will grow after the temperature shift.

Methods of Identifying Agents Which Affect Life Span

The above-described methods for isolating mutant yeast cells with a longer life span can be employed to identify agents which alter the life span of a yeast strain. In this embodiment of the current invention, the yeast strain of interest, for which the life span is known or has been calculated, is exposed to the agent to be tested rather than subjected to a mutagen. The samples thus exposed are then examined for longer-lived colonies, using any of the methods described above. Colonies exhibiting a longer life span in the presence of the agent than in the absence of the agent are indicative of the ability of the agent to increase life span, or to postpone senescence. Agents include drugs, peptides, oligonucleotides, and genes encoding proteins that increase life span, such as genes isolated by the methods described below.

Methods of Isolating Genes Involved in Altering Life Span

Genes which contribute to senescence can be isolated by complementation analysis, or by isolation of DNA homologous to other genes known to contribute to senescence. In one embodiment of the current invention, cells from a budding yeast strain, such as 14c, in which the SIR4 gene has been mutated as described above, and which as a result have a longer life span, are utilized. The SIR4 gene can be mutated through site-specific mutagenesis, for example. A genomic DNA library generated from an organism of interest, including another yeast strain, bacteria, or mammals, is used to transform the yeast cells. The cells are then plated and grown. Those yeast cells which exhibit the usual life span of the yeast strain, rather than the longer life of the cells in which SIR4 is mutated, are selected. These cells contain DNA from the organism of interest which comprises a gene that contributes to senescence. The DNA from the organism of interest is then isolated from these yeast cells.

Genes which contribute to longer life span can also be isolated by complementation analysis, or by isolation of DNA homologous to other genes known to contribute to longer life span. In one embodiment of the current invention, cells from a budding yeast strain, such as 14c, are utilized. These cells should have a normal life span; i.e., the SIR4 gene should not be mutated. A genomic DNA library generated from an organism of interest, including another yeast strain, bacteria, or mammals, is used to transform the yeast cells. The cells are then plated and grown. Those yeast cells which exhibit a longer life span of the yeast strain, rather than the usual life span of the cells, are selected. These cells contain DNA from the organism of interest which comprises a gene that contributes to longer life span (i.e., a gene that increases life span). The DNA from the organism of interest is then isolated from these yeast cells. In another embodiment, genes in other organisms that are the functional equivalent of SIR4 in yeast can be investigated to determine whether a mutation corresponding to the SIR4 mutation (stop codon at amino acid 1237 of the encoded protein) results in a mutated gene that contributes to longer life span.

In another embodiment of the current invention, homologous genes can be isolated by hybridization. In one particular embodiment, a labelled DNA fragment comprising the SIR4 gene, the UTH1 gene or the UTH4 gene is used to probe cellular DNA from an organism of interest under high, medium or low hybridization stringency conditions, depending on the degree of homology sought. For description of appropriate stringency conditions, see Sambrook et al., eds., *Molecular Cloning: A Laboratory Manual*, 2nd ed., Cold Spring Harbor Laboratory Press, 1989, or Ausubel, F. M. et al., eds. *Current Protocols in Molecular Biology*, 1994. DNA hybridizing to the probe is isolated, and complementation analysis is performed to verify that the DNA comprises a gene which contributes to senescence. In one embodiment, DNA from an organism of interest is hybridized under high stringency conditions to DNA comprising a mutated SIR4 gene (i.e., a stop codon at amino acid 1237 of the encoded protein). Alternatively, labelled DNA comprising genes isolated by the complementation method described above can be used as the probe.

Homologous genes can also be found by computerized database searches to identify genes which include regions of homology to the SUN domains of the UTH1, NCA3 and SAG1 genes or to the repeating-box region of the UTH4, PUMILIO, YGL023, D13645 or D43951 genes. Homologous genes can also be found by the polymerase chain reaction (PCR) (see Sakai, R. K. et al., *Science* 230:1350–4 (1985), and Sakai, R. K. et al., *Science* 239: 487–91 (1988)). Synthetic oligonucleotide primers which comprise regions of the SIR4 gene or the UTH1 gene can be used. In one embodiment, synthetic oligonucleotide primers which comprise the region of the SIR4 gene that contains the mutation (the stop codon at amino acid 1237 of the encoded protein) are used. Alternatively, oligonucleotides can be patterned after any gene, such as those isolated by this method or any of the above methods, which contributes to senescence or to longer life span. The oligonucleotides are utilized in PCR to generate multiple copies of DNA of interest from a sample of genomic DNA from the organism of interest. The DNA multiplied in PCR is then isolated, and complementation analysis is performed to verify that the DNA comprises a functional gene which contributes to senescence or to longer life span. Once genes have been isolated using these methods, standard procedures can then be used to isolate the proteins encoded by the genes.

Methods of Increasing Life Span in Yeast

Because the sir4-42 mutation is a semi-dominant mutation, and because addition of "anti-SIR4" (residues 1205–1358 of SIR4) to yeast cells increases the life span by 20–45%, it is now possible to increase the life span of any cell by adding "anti-SIR4". For example, a plasmid which expresses residues 1205–1358 can be inserted into the cell of interest. Expression of the anti-SIR4 protein will increase the life span. The life span can also be increased by adding mutant SIR4 protein (protein produced by the mutated SIR4 gene, in which there is a stop codon at amino acid 1237 of the encoded protein). For example, a plasmid which expresses the mutant SIR4 protein can be inserted into the cell of interest. Alternatively, "anti-SIR4" protein or protein produced by the mutant SIR4 gene can be added to the cell, thereby increasing the cell's life span.

Equivalents

Those skilled in the art will recognize, or be able to ascertain using no more than routine experimentation, many equivalents to specific embodiments of the invention described specifically herein. Such equivalents are intended to be encompassed in the scope of the following claims.

The invention claimed is:

1. A method of isolating a gene which encodes a protein that contributes to senescence in an organism, comprising the steps of:
   a) generating a genomic DNA library from the organism of interest;
   b) transforming yeast cells from a budding yeast strain, in which the SIR4 gene has been mutated to generate a stop codon at amino acid 1237 of the encoded protein, with the library;
   c) plating the transformed yeast cells, and culturing them under conditions for growth of yeast cells;
   d) calculating the life span of the colonies of transformed yeast cells;
   e) selecting yeast cells from colonies in which the life span of the yeast cells is about equal to the life span of the yeast strain in which the SIR4 gene has not been mutated to generate a stop at codon 1237, thereby obtaining yeast cells containing senescence genes from the organism of interest; and
   i) isolating from the selected yeast cells the DNA from the organism of interest,
thereby obtaining a gene encoding a protein that contributes to senescence.

2. A gene which encodes a protein that contributes to senescence in an organism, isolated by the method of claim 1, wherein said gene is not the wild-type SIR4 gene.

3. A gene which encodes a protein that contributes to senescence in an organism, wherein said gene is not the wild-type SIR4 gene, and which hybridizes under conditions of high stringency to a gene isolated by the method of claim 1.

4. A method of isolating DNA which contributes to senescence in an organism comprising the steps of:
   a) generating a genomic DNA library from the organism of interest;
   b) contacting the library with a labeled probe comprising DNA encoding the SIR4 gene or the UTH1 gene, under conditions of high stringency; and
   c) isolating from the library DNA which hybridizes to the labeled probe.

5. Isolated DNA consisting essentially of a gene contributing to senescence in an organism, isolated by the method of claim 4, wherein said gene is not the wild-type SIR4 gene.

6. A mutant SIR4 gene having a stop codon at amino acid 1237 of the encoded protein.

7. A gene encoding a protein having the amino acid sequence encoded by a SIR4 gene having a stop codon at amino acid 1237 of the encoded protein.

8. DNA which encodes a protein that contributes to extended life span and which hybridizes under high stringency conditions to the gene of claim 6, wherein said DNA does not encode the wild-type SIR4 gene.

9. DNA which hybridizes under high stringency conditions to the UTH1 gene having the nucleotide sequence of SEQ ID. NO. 1.

10. A gene encoding a UTH1 protein having the amino acid sequence of SEQ. ID. NO. 2.

11. A method of isolating DNA which contributes to extended life span, comprising the steps of:
   a) exposing a sample of yeast cells from a budding yeast strain, for which the life span is known, to a mutagen;
   b) plating the sample of cells on minimal medium necessary for growth of yeast cells, thereby generating an original plate;
   c) replica-plating the original plate to a plate with a medium lacking nutrients necessary for growth of yeast cells, thereby generating a replica plate;
   d) culturing the original plate and the replica plate under conditions appropriate for growth of yeast cells;
   e) replica-plating the replica plate to enriched medium, thereby generating an enriched plate;
   f) culturing the enriched plates under conditions for growth of yeast cells, thereby generating colonies of yeast cells which are starvation resistant;
   g) calculating the life span of yeast cells in the starvation resistant colonies;
   h) selecting those yeast cells with a life span that is longer than the known life span of the yeast strain;
   i) isolating the DNA from the yeast cells with a life span that is longer than the known life span of the yeast strain; and
   j) isolating from the DNA of step (i) DNA which contributes to extended life span,
thereby isolating DNA which contributes to extended life span.

12. A method of isolating DNA which contributes to extended life span, comprising the steps of:
   a) exposing a sample of yeast cells from a budding yeast strain, for which the life span is known, to a mutagen;
   b) labelling the cell surface of the yeast cells with a fluorescent marker, thereby generating fluorescent yeast cells;
   c) culturing the yeast cells under conditions for growth of yeast cells, and for a period of time greater than the chronological life span of the strain;
   d) subjecting the yeast cells to fluorescence-activated cell sorting, thereby separating fluorescent yeast cells from non-fluorescent yeast cells;
   e) replating the fluorescent yeast cells, under conditions for growth of yeast cells, wherein the fluorescent yeast cells which grow after replating are mutant yeast cells having an increased life span;
   f) isolating the DNA from the fluorescent yeast cells which grow after replating; and
   g) isolating from the DNA of step (f) DNA which contributes to extended life span,
thereby isolating DNA which contributes to extended life span.

13. A method of isolating DNA which contributes to extended life span, comprising the steps of:
   a) exposing a sample of yeast cells from a temperature-sensitive budding yeast strain, in which the daughter cells die at the nonpermissive temperature, and for which the life span is known, to a mutagen;

b) plating the yeast cells, and cultivating the yeast cells at the permissive temperature and under conditions for growth of yeast cells;

c) transferring a sample of yeast cells from each colony of the plate at the permissive temperature to a second plate;

d) cultivating the yeast cells transferred to the second plate at the nonpermissive temperature, thereby generating microcolonies of yeast cells;

e) calculating the number of yeast cells in the microcolonies, wherein if a microcolony consists of a number of yeast cells that is greater than the number of generations in the life span of the yeast strain, the microcolony contains mutant yeast cells having an increased life span;

f) isolating the DNA from a microcolony consisting of a number of yeast cells that is greater than the number of generations in the life span of the yeast strain; and g) isolating from the DNA of step (f) DNA which contributes to extended life span, thereby isolating DNA which contributes to extended life span.

14. A method of isolating DNA which contributes to extended life span, comprising the steps of:

a) exposing a sample of yeast cells from a temperature-sensitive budding yeast strain, in which the daughter cells die at the nonpermissive temperature, and for which the life span is known, to a mutagen;

b) plating the yeast cells, and cultivating the yeast cells at the nonpermissive temperature for a period of time greater than the chronological life span of the strain, thereby generating microcolonies of yeast cells;

c) shifting the microcolonies to the permissive temperature, wherein the yeast cells which grow after the shift to the permissive temperature are mutant yeast cells having an increased life span;

d) isolating the DNA from yeast cells which grow after the shift to the permissive temperature; and e) isolating from the DNA of step (f) DNA which contributes to extended life span, thereby isolating DNA which contributes to extended life span.

15. DNA which contributes to extended life span isolated by the method of claim 11.

16. DNA which contributes to extended life span isolated by the method of claim 12.

17. DNA which contributes to extended life span isolated by the method of claim 13.

18. DNA which contributes to extended life span isolated by the method of claim 14.

19. DNA encoding a protein, said protein comprising the SUN domain region, or a region encoded by DNA which hybridizes under high stringency conditions to the DNA encoding the SUN domain region, said SUN domain region consisting of amino acid 123 through amino acid 337 of SEQ ID NO. 12.

* * * * *

SEQUENCE LISTING (1) GENERAL INFORMATION:

(iii) NUMBER OF SEQUENCES: 16

(2) INFORMATION FOR SEQ ID NO:1:

(i) SEQUENCE CHARACTERISTICS:
      (A) LENGTH: 1946 base pairs
      (B) TYPE: nucleic acid
      (C) STRANDEDNESS: double
      (D) TOPOLOGY: linear (ii) MOLECULE TYPE: DNA (genomic)

(ix) FEATURE:
      (A) NAME/KEY: CDS
      (B) LOCATION: 322..1671

(xi) SEQUENCE DESCRIPTION: SEQ ID NO:1:

```
TGAAAAAGTG GAACTAGACC CCACGTCAGC GGGCCTAGGC CCTTCAATGT GTTAGAATAC        60

ACAGCGTGCC TAGTTCCTGG TGCCTGGATC TCGAGGCCGC GGCACTGGAA AAGCCCTTTC       120

TTTTCCAGAT CGGGAAACCT AATGAGTCCA TAAAAAGAAA TGTAGAGGTG GTGTTGACGT       180

TTTGCCGCTT TTGGGCAAGT AGGTCTTTCT GCACGGCCCG GCCCGGGTCG TGCGGAAAAA       240

GAAAAAGCA GACAAAACAA AATTTTTCCT TTTTTTCGCC TTTGTTTCTC CTGATTCGGG       300

TATATAAGTG AATACCATCT A ATG TGT TTC CTT CTC GAG ACC TCG GCG TCT       351
```

|  |  |  |  |  |  |  |  |  |  |  |  |  |  |  |  |
|---|---|---|---|---|---|---|---|---|---|---|---|---|---|---|---|
|  |  |  |  | Met<br>1 | Cys | Phe | Leu | Leu<br>5 | Glu | Thr | Ser | Ala | Ser<br>10 |  |  |
| CCC<br>Pro | AGA<br>Arg | TCA<br>Ser | AAG<br>Lys<br>15 | CTC<br>Leu | AGC<br>Ser | AAA<br>Lys | GAT<br>Asp | TTT<br>Phe | AAA<br>Lys<br>20 | CCG<br>Pro | CAA<br>Gln | TTT<br>Phe | ACG<br>Thr | CTC<br>Leu<br>25 | CTT<br>Leu | 399 |
| TCA<br>Ser | TCG<br>Ser | GTA<br>Val | ACT<br>Thr<br>30 | AAG<br>Lys | AAG<br>Lys | AAA<br>Lys | AAA<br>Lys | AAA<br>Lys<br>35 | AAA<br>Lys | GTA<br>Val | CGA<br>Arg | CCA<br>Pro | CAC<br>His<br>40 | AAT<br>Asn | TTC<br>Phe | 447 |
| CAG<br>Gln | TGT<br>Cys | ATT<br>Ile<br>45 | CAT<br>His | TCC<br>Ser | TTA<br>Leu | AAC<br>Asn | TTC<br>Phe<br>50 | GTT<br>Val | TAT<br>Tyr | TTT<br>Phe | TTA<br>Leu | TTC<br>Phe<br>55 | ATT<br>Ile | CAT<br>His | TCA<br>Ser | 495 |
| TTT<br>Phe | TTA<br>Leu<br>60 | TTT<br>Phe | GAA<br>Glu | TAT<br>Tyr | AAC<br>Asn | CAA<br>Gln<br>65 | CTA<br>Leu | CTA<br>Leu | GTC<br>Val | CTT<br>Leu | CCT<br>Pro<br>70 | TTA<br>Leu | AAC<br>Asn | AAA<br>Lys | AAT<br>Asn | 543 |
| TTA<br>Leu<br>75 | CCC<br>Pro | TCC<br>Ser | CTT<br>Leu | AAT<br>Asn | TTT<br>Phe<br>80 | TCA<br>Ser | AGA<br>Arg | AAT<br>Asn | TCC<br>Ser | AGT<br>Ser<br>85 | ATG<br>Met | AAA<br>Lys | TTA<br>Leu | TCC<br>Ser | GCT<br>Ala<br>90 | 591 |
| CTA<br>Leu | TTA<br>Leu | GCT<br>Ala | TTA<br>Leu | TCA<br>Ser<br>95 | GCC<br>Ala | TCC<br>Ser | ACC<br>Thr | GCC<br>Ala | GTC<br>Val<br>100 | TTG<br>Leu | GCC<br>Ala | GCT<br>Ala | CCA<br>Pro | GCT<br>Ala<br>105 | GTC<br>Val | 639 |
| CAC<br>His | CAT<br>His | AGT<br>Ser | GAC<br>Asp | AAC<br>Asn<br>110 | CAC<br>His | CAC<br>His | CAC<br>His | AAC<br>Asn<br>115 | GAC<br>Asp | AAG<br>Lys | CGT<br>Arg | GCC<br>Ala | GTT<br>Val<br>120 | GTC<br>Val | ACC<br>Thr | 687 |
| GTT<br>Val | ACT<br>Thr | CAG<br>Gln<br>125 | TAC<br>Tyr | GTC<br>Val | AAC<br>Asn | GCA<br>Ala | GAC<br>Asp<br>130 | GGC<br>Gly | GCT<br>Ala | GTT<br>Val | GTT<br>Val | ATT<br>Ile<br>135 | CCA<br>Pro | GCT<br>Ala | GCC<br>Ala | 735 |
| ACC<br>Thr | ACC<br>Thr<br>140 | GCT<br>Ala | ACC<br>Thr | TCG<br>Ser | GCG<br>Ala<br>145 | GCT<br>Ala | GCT<br>Ala | GAT<br>Asp | GGA<br>Gly | AAG<br>Lys<br>150 | GTC<br>Val | GAG<br>Glu | TCT<br>Ser | GTT<br>Val | GCT<br>Ala | 783 |
| GCT<br>Ala<br>155 | GCC<br>Ala | ACC<br>Thr | ACT<br>Thr | ACT<br>Thr<br>160 | TTG<br>Leu | TCC<br>Ser | TCG<br>Ser | ACT<br>Thr | GCC<br>Ala<br>165 | GCC<br>Ala | GCC<br>Ala | GCT<br>Ala | ACT<br>Thr | ACC<br>Thr<br>170 | TCT<br>Ser | 831 |
| GCC<br>Ala | GCC<br>Ala | GCC<br>Ala | TCT<br>Ser<br>175 | TCT<br>Ser | TCC<br>Ser | TCC<br>Ser | TCT<br>Ser | TCC<br>Ser<br>180 | TCT<br>Ser | TCC<br>Ser | TCC<br>Ser | TCT<br>Ser | TCC<br>Ser<br>185 | TCT<br>Ser | TCT<br>Ser | 879 |
| TCC<br>Ser | TCT<br>Ser | GTT<br>Val<br>190 | GGT<br>Gly | TCT<br>Ser | GGA<br>Gly | GAT<br>Asp | TTT<br>Phe<br>195 | GAA<br>Glu | GAT<br>Asp | GGT<br>Gly | ACC<br>Thr | ATT<br>Ile<br>200 | TCC<br>Ser | TGT<br>Cys | TCT<br>Ser | 927 |
| GAT<br>Asp | TTC<br>Phe | CCA<br>Pro<br>205 | TCC<br>Ser | GGA<br>Gly | CAA<br>Gln | GGT<br>Gly<br>210 | GCT<br>Ala | GTC<br>Val | TCC<br>Ser | TTG<br>Leu | GAC<br>Asp<br>215 | TGG<br>Trp | TTA<br>Leu | GGT<br>Gly | CTA<br>Leu | 975 |
| GGC<br>Gly | GGC<br>Gly<br>220 | TGG<br>Trp | GCT<br>Ala | TCC<br>Ser | ATC<br>Ile<br>225 | ATG<br>Met | GAC<br>Asp | ATG<br>Met | AAC<br>Asn | GGT<br>Gly<br>230 | AAC<br>Asn | ACC<br>Thr | GCC<br>Ala | ACC<br>Thr | TCT<br>Ser | 1023 |
| TGT<br>Cys<br>235 | CAA<br>Gln | GAC<br>Asp | GGA<br>Gly | TAC<br>Tyr<br>240 | TAC<br>Tyr | TGT<br>Cys | TCT<br>Ser | TAC<br>Tyr | GCT<br>Ala<br>245 | TGT<br>Cys | TCT<br>Ser | CCA<br>Pro | GGT<br>Gly | TAC<br>Tyr<br>250 | GCT<br>Ala | 1071 |
| AAG<br>Lys | ACC<br>Thr | CAA<br>Gln | TGG<br>Trp<br>255 | CCT<br>Pro | TCT<br>Ser | GAA<br>Glu | CAA<br>Gln | CCT<br>Pro<br>260 | TCC<br>Ser | GAT<br>Asp | GGT<br>Gly | AGA<br>Arg | TCC<br>Ser<br>265 | GTT<br>Val | GGT<br>Gly | 1119 |
| GGT<br>Gly | TTA<br>Leu | TAC<br>Tyr<br>270 | TGT<br>Cys | AAG<br>Lys | AAC<br>Asn | GGT<br>Gly | AAA<br>Lys<br>275 | TTA<br>Leu | TAC<br>Tyr | CGT<br>Arg | TCC<br>Ser | AAC<br>Asn<br>280 | ACC<br>Thr | GAC<br>Asp | ACT<br>Thr | 1167 |
| AAC<br>Asn | AGT<br>Ser<br>285 | TTG<br>Leu | TGT<br>Cys | GTA<br>Val | GAA<br>Glu<br>290 | GGT<br>Gly | CAA<br>Gln | GGC<br>Gly | TCT<br>Ser | GCT<br>Ala<br>295 | CAA<br>Gln | GCT<br>Ala | GTT<br>Val | AAC<br>Asn | AAG<br>Lys | 1215 |
| GTC<br>Val<br>300 | TCC<br>Ser | GGC<br>Gly | TCC<br>Ser | ATT<br>Ile<br>305 | GCT<br>Ala | ATC<br>Ile | TGT<br>Cys | GGT<br>Gly | ACC<br>Thr<br>310 | GAT<br>Asp | TAT<br>Tyr | CCA<br>Pro | GGT<br>Gly | TCT<br>Ser | GAA<br>Glu | 1263 |
| AAC<br>Asn | ATG<br>Met | GTC<br>Val | GTT<br>Val | CCT<br>Pro | ACC<br>Thr | GTA<br>Val | GTT<br>Val | GGC<br>Gly | GCT<br>Ala | GGT<br>Gly | TCC<br>Ser | TCC<br>Ser | CAA<br>Gln | CCA<br>Pro | ATC<br>Ile | 1311 |

-continued

```
Asn Met Val Val Pro Thr Val Val Gly Ala Gly Ser Ser Gln Pro Ile
315                 320                 325                 330

AAC GTC ATC AAG GAG GAC TCC TAC TAT CAA TGG CAA GGT AAG AAG ACC    1359
Asn Val Ile Lys Glu Asp Ser Tyr Tyr Gln Trp Gln Gly Lys Lys Thr
                        335                 340                 345

TCT GCC CAA TAC TAC GTT AAC AAC GCT GGT GTC TCT GTG GAA GAT GGT    1407
Ser Ala Gln Tyr Tyr Val Asn Asn Ala Gly Val Ser Val Glu Asp Gly
                350                 355                 360

TGT ATC TGG GGT ACT GAG GGT TCC GGT GTC GGT AAC TGG GCC CCA GTT    1455
Cys Ile Trp Gly Thr Glu Gly Ser Gly Val Gly Asn Trp Ala Pro Val
            365                 370                 375

GTC TTG GGT GCT GGT TAC ACT GAT GGT ATC ACT TAC TTG TCC ATC ATT    1503
Val Leu Gly Ala Gly Tyr Thr Asp Gly Ile Thr Tyr Leu Ser Ile Ile
        380                 385                 390

CCA AAC CCA AAC AAC AAA GAA GCA CCA AAC TTT AAC ATC AAG ATC GTT    1551
Pro Asn Pro Asn Asn Lys Glu Ala Pro Asn Phe Asn Ile Lys Ile Val
395                 400                 405                 410

GCC ACC GAT GGC TCT ACC GTC AAT GGT GCT TGC TCT TAC GAA AAT GGT    1599
Ala Thr Asp Gly Ser Thr Val Asn Gly Ala Cys Ser Tyr Glu Asn Gly
                    415                 420                 425

GTC TAC TCT GGC TCT GGC TCT GAC GGT TGT ACT GTT TCA GTT ACT TCT    1647
Val Tyr Ser Gly Ser Gly Ser Asp Gly Cys Thr Val Ser Val Thr Ser
                430                 435                 440

GGT TCT GCT AAC TTT GTC TTC TAC TAGGCCTTTT TTCCTTGAAT ATTGCAAATA   1701
Gly Ser Ala Asn Phe Val Phe Tyr
            445             450

AGCTTTTGCT AGTACTTTTT TTACTCCGTT CATTTTATGG TTTATTTTTC AATTAGTTCG  1761

TTTTTCCACA ATACAAAAAA ACACAGTCCT TTGTACTATC CCTTTTATTT CATTATTTTT  1821

TCTTTTTTAA GATACCACTA GATATTATCA TATATAGCAT ATTATATAAC ATAAAAAGTC  1881

AAGAAAAAAA ATGTTTTTAT CACTTTCTAT AACTGCATAT CTTTTTTTGC ATTTCGAATG  1941

ATTGC                                                              1946
```

(2) INFORMATION FOR SEQ ID NO:2:

(i) SEQUENCE CHARACTERISTICS:
        (A) LENGTH: 450 amino acids
        (B) TYPE: amino acid
        (D) TOPOLOGY: linear (ii) MOLECULE TYPE: protein (xi) SEQUENCE DESCRIPTION: SEQ ID NO:2:

```
Met Cys Phe Leu Leu Glu Thr Ser Ala Ser Pro Arg Ser Lys Leu Ser
1               5                   10                  15

Lys Asp Phe Lys Pro Gln Phe Thr Leu Leu Ser Ser Val Thr Lys Lys
                20                  25                  30

Lys Lys Lys Lys Val Arg Pro His Asn Phe Gln Cys Ile His Ser Leu
            35                  40                  45

Asn Phe Val Tyr Phe Leu Phe Ile His Ser Phe Leu Phe Glu Tyr Asn
        50                  55                  60

Gln Leu Leu Val Leu Pro Leu Asn Lys Asn Leu Pro Ser Leu Asn Phe
65                  70                  75                  80

Ser Arg Asn Ser Ser Met Lys Leu Ser Ala Leu Leu Ala Leu Ser Ala
                85                  90                  95

Ser Thr Ala Val Leu Ala Ala Pro Ala Val His His Ser Asp Asn His
                100                 105                 110

His His Asn Asp Lys Arg Ala Val Val Thr Val Thr Gln Tyr Val Asn
            115                 120                 125
```

```
Ala Asp Gly Ala Val Val Ile Pro Ala Ala Thr Thr Ala Thr Ser Ala
    130                 135                 140
Ala Ala Asp Gly Lys Val Glu Ser Val Ala Ala Thr Thr Thr Leu
145                 150                 155                 160
Ser Ser Thr Ala Ala Ala Thr Thr Ser Ala Ala Ala Ser Ser Ser
                165                 170                 175
Ser Ser Ser Ser Ser Ser Ser Ser Ser Ser Val Gly Ser Gly
            180                 185                 190
Asp Phe Glu Asp Gly Thr Ile Ser Cys Ser Asp Phe Pro Ser Gly Gln
            195                 200                 205
Gly Ala Val Ser Leu Asp Trp Leu Gly Leu Gly Trp Ala Ser Ile
            210                 215                 220
Met Asp Met Asn Gly Asn Thr Ala Thr Ser Cys Gln Asp Gly Tyr Tyr
225                 230                 235                 240
Cys Ser Tyr Ala Cys Ser Pro Gly Tyr Ala Lys Thr Gln Trp Pro Ser
                245                 250                 255
Glu Gln Pro Ser Asp Gly Arg Ser Val Gly Gly Leu Tyr Cys Lys Asn
            260                 265                 270
Gly Lys Leu Tyr Arg Ser Asn Thr Asp Thr Asn Ser Leu Cys Val Glu
            275                 280                 285
Gly Gln Gly Ser Ala Gln Ala Val Asn Lys Val Ser Gly Ser Ile Ala
            290                 295                 300
Ile Cys Gly Thr Asp Tyr Pro Gly Ser Glu Asn Met Val Val Pro Thr
305                 310                 315                 320
Val Val Gly Ala Gly Ser Ser Gln Pro Ile Asn Val Ile Lys Glu Asp
                325                 330                 335
Ser Tyr Tyr Gln Trp Gln Gly Lys Lys Thr Ser Ala Gln Tyr Tyr Val
            340                 345                 350
Asn Asn Ala Gly Val Ser Val Glu Asp Gly Cys Ile Trp Gly Thr Glu
            355                 360                 365
Gly Ser Gly Val Gly Asn Trp Ala Pro Val Val Leu Gly Ala Gly Tyr
    370                 375                 380
Thr Asp Gly Ile Thr Tyr Leu Ser Ile Ile Pro Asn Pro Asn Asn Lys
385                 390                 395                 400
Glu Ala Pro Asn Phe Asn Ile Lys Ile Val Ala Thr Asp Gly Ser Thr
                405                 410                 415
Val Asn Gly Ala Cys Ser Tyr Glu Asn Gly Val Tyr Ser Gly Ser Gly
            420                 425                 430
Ser Asp Gly Cys Thr Val Ser Val Thr Ser Gly Ser Ala Asn Phe Val
            435                 440                 445
Phe Tyr
    450

(2) INFORMATION FOR SEQ ID NO:3:

(i) SEQUENCE CHARACTERISTICS:
        (A) LENGTH: 3455 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 663..3164

(xi) SEQUENCE DESCRIPTION: SEQ ID NO:3:
```

-continued

```
AAGCTTTAAC GGGATCTTCT AACAACAAAT AGCATAATAA CCAAAAACCA GCTTCAGTGG    60

GATCAGCCTA TCGACACGCC TTTTTTAGCG GTCTAACAAT CTCCGTTTAT GTCGTATGGA   120

ATTTCTATAC TTGACCCTAC CTTATTTCTC GAATATGCCT ATAAGGATTT TCTCGAAAGA   180

AGGGCTTCGG GAAAGAGGCG CCTCAGGCAA AAATGAGCAA AAAAAAAAAA AAAAAGAAAA   240

GATTCGAAGA TCTATGAAAA ATTTATGCAG ATTCGTTGAG AGTTATAAGG ATTTTACTCT   300

TTATGGTTAT AGGTTTCATT CTAAAATCAA GCATAAATTT TGTGTTTTGT CTTCCTCTTT   360

TCCTGTCCTC TTTTTTTGCC ATCCTCTGTC GCCATTGAAG TCGAACTTTA TAGATAGATT   420

TACTCTTGAT TCTCACGCAT CTCAGGCCAC CTGGACACTG TACATGGTTG TGATTGTTCT   480

CTTTCTCAGT TATCGAAATT GATCCTAGGC TTATACTCCA AAATCGGCTC TGCACACGCC   540

TTATTTTTGT GGTTTCACTT TACTAACACA ACATTCTTTT ATTCAATCAG ATCAATAACG   600

AACCATTTCC ATCTGCCGAC TCAGCATCGA TTTTAACTAC GTCTACATCA AATAACTCCT   660

TA ATG TCT TAC AAT CAT CAG CCT CAA CTA TCT ATT AAC TCC GTC CAA      707
   Met Ser Tyr Asn His Gln Pro Gln Leu Ser Ile Asn Ser Val Gln
   1               5                   10                  15

TCA CTC TTG GAG CCC GTG ACC CCT CCG CCT TTG GGC CAG ATG AAT AAC    755
Ser Leu Leu Glu Pro Val Thr Pro Pro Pro Leu Gly Gln Met Asn Asn
                20                  25                  30

AAA AGA AAC CAT CAA AAG GCT CAT TCG CTT GAT CTC TCT GGT TTT AAT    803
Lys Arg Asn His Gln Lys Ala His Ser Leu Asp Leu Ser Gly Phe Asn
            35                  40                  45

CAG TTC ATA TCA TCG ACA CAA TCT CCC TTG GCT TTG ATG AAT AAT ACA    851
Gln Phe Ile Ser Ser Thr Gln Ser Pro Leu Ala Leu Met Asn Asn Thr
        50                  55                  60

TCA ACA TCG AAT TCT GCT AAC TCT TTT TCC CCG AAT CCT AAT GCT GCT    899
Ser Thr Ser Asn Ser Ala Asn Ser Phe Ser Pro Asn Pro Asn Ala Ala
    65                  70                  75

AGC AAC TCC ACT GGG CTT TCA GCC TCA ATG GCA AAT CCT CCA GCC ATT    947
Ser Asn Ser Thr Gly Leu Ser Ala Ser Met Ala Asn Pro Pro Ala Ile
80                  85                  90                  95

CTA CCA TTA ATC AAT GAG TTT GAT CTG GAA ATG GAT GGT CCC AGG AGA    995
Leu Pro Leu Ile Asn Glu Phe Asp Leu Glu Met Asp Gly Pro Arg Arg
                100                 105                 110

AAA TCA AGC CAC GAT TTC ACG GTT GTT GCT CCT TCG AAC TCT GGT GTC   1043
Lys Ser Ser His Asp Phe Thr Val Val Ala Pro Ser Asn Ser Gly Val
            115                 120                 125

AAT ACC TCC AGT TTA ATT ATG GAA ACA CCA TCC TCT TCA GTG ACT CCT   1091
Asn Thr Ser Ser Leu Ile Met Glu Thr Pro Ser Ser Ser Val Thr Pro
        130                 135                 140

GCT GCA TCT CTC AGA AAT TTT AGC AAT AGT AAT AAT GCT GCT TCC AAA   1139
Ala Ala Ser Leu Arg Asn Phe Ser Asn Ser Asn Asn Ala Ala Ser Lys
    145                 150                 155

TGT GGA GTG GAT AAT TCG TCA TTT GGT TTG AGT AGC TCA ACG TCT TCA   1187
Cys Gly Val Asp Asn Ser Ser Phe Gly Leu Ser Ser Ser Thr Ser Ser
160                 165                 170                 175

TCT ATG GTC GAA ATC AGC GCA CTA CCC CTT AGA GAT CTG GAT TAT ATC   1235
Ser Met Val Glu Ile Ser Ala Leu Pro Leu Arg Asp Leu Asp Tyr Ile
                180                 185                 190

AAA CTT GCC ACT GAC CAG TTT GGC TGC CGT TTT CTT CAA AAA AAA TTA   1283
Lys Leu Ala Thr Asp Gln Phe Gly Cys Arg Phe Leu Gln Lys Lys Leu
            195                 200                 205

GAA ACC CCC AGT GAA TCC AAT ATG GTG AGA GAC TTG ATG TAT GAA CAA   1331
Glu Thr Pro Ser Glu Ser Asn Met Val Arg Asp Leu Met Tyr Glu Gln
        210                 215                 220

ATT AAG CCA TTT TTC TTG GAC CTT ATT TTG GAT CCG TTC GGT AAC TAT   1379
```

```
                                            -continued

Ile Lys Pro Phe Phe Leu Asp Leu Ile Leu Asp Pro Phe Gly Asn Tyr
    225                 230                 235

TTG GTT CAA AAA CTA TGC GAT TAT TTA ACT GCC GAG CAA AAG ACA TTA    1427
Leu Val Gln Lys Leu Cys Asp Tyr Leu Thr Ala Glu Gln Lys Thr Leu
240                 245                 250                 255

TTA ATA CAA ACA ATA TAT CCA AAT GTT TTC CAA ATA TCA ATC AAT CAG    1475
Leu Ile Gln Thr Ile Tyr Pro Asn Val Phe Gln Ile Ser Ile Asn Gln
                    260                 265                 270

TAC GGA ACT CGT TCC TTA CAG AAA ATT ATA GAC ACT GTC GAT AAC GAA    1523
Tyr Gly Thr Arg Ser Leu Gln Lys Ile Ile Asp Thr Val Asp Asn Glu
                275                 280                 285

GTT CAA ATC GAT CTC ATT ATT AAG GGA TTT TCC CAA GAA TTT ACT TCG    1571
Val Gln Ile Asp Leu Ile Ile Lys Gly Phe Ser Gln Glu Phe Thr Ser
            290                 295                 300

ATT GAG CAA GTG GTT ACT TTG ATA AAC GAT CTT AAT GGT AAC CAT GTG    1619
Ile Glu Gln Val Val Thr Leu Ile Asn Asp Leu Asn Gly Asn His Val
305                 310                 315

ATT CAA AAG TGT ATT TTC AAA TTC TCG CCA TCA AAA TTT GGT TTC ATC    1667
Ile Gln Lys Cys Ile Phe Lys Phe Ser Pro Ser Lys Phe Gly Phe Ile
320                 325                 330                 335

ATA GAT GCT ATT GTA GAA CAA AAT AAT ATC ATT ACC ATT TCT ACC CAT    1715
Ile Asp Ala Ile Val Glu Gln Asn Asn Ile Ile Thr Ile Ser Thr His
                340                 345                 350

AAA CAT GGT TGT TGC GTA CTA CAA AAA TTA CTA AGC GTT TGT ACT CTA    1763
Lys His Gly Cys Cys Val Leu Gln Lys Leu Leu Ser Val Cys Thr Leu
                355                 360                 365

CAA CAA ATT TTC AAA ATT TCT GTG AAA ATT GTG CAG TTC CTT CCT GGA    1811
Gln Gln Ile Phe Lys Ile Ser Val Lys Ile Val Gln Phe Leu Pro Gly
            370                 375                 380

TTA ATC AAC GAT CAG TTC GGT AAT TAT ATC ATC CAA TTT CTG TTA GAT    1859
Leu Ile Asn Asp Gln Phe Gly Asn Tyr Ile Ile Gln Phe Leu Leu Asp
385                 390                 395

ATC AAA GAA TTG GAC TTT TAC TTA TTG GCT GAG TTA TTT AAC CGT TTA    1907
Ile Lys Glu Leu Asp Phe Tyr Leu Leu Ala Glu Leu Phe Asn Arg Leu
400                 405                 410                 415

TCC AAT GAA TTA TGT CAA CTA TCT TGT TTG AAG TTC TCC TCA AAT GTT    1955
Ser Asn Glu Leu Cys Gln Leu Ser Cys Leu Lys Phe Ser Ser Asn Val
                420                 425                 430

GTG GAA AAA TTC ATT AAA AAA TTA TTT AGA ATC ATT ACT GGA TTT ATT    2003
Val Glu Lys Phe Ile Lys Lys Leu Phe Arg Ile Ile Thr Gly Phe Ile
                435                 440                 445

GTT AAT AAC AAT GGG GGT GCC TCC CAA AGG ACT GCA GTT GCT TCT GAT    2051
Val Asn Asn Asn Gly Gly Ala Ser Gln Arg Thr Ala Val Ala Ser Asp
            450                 455                 460

GAC GTG ATT AAT GCT TCT ATG AAC ATT CTT TTG ACT ACC ATT GAT ATA    2099
Asp Val Ile Asn Ala Ser Met Asn Ile Leu Leu Thr Thr Ile Asp Ile
465                 470                 475

TTC ACA GTC AAT TTA AAT GTG CTA ATC AGG GAT AAT TTT GGT AAT TAT    2147
Phe Thr Val Asn Leu Asn Val Leu Ile Arg Asp Asn Phe Gly Asn Tyr
480                 485                 490                 495

GCG TTA CAA ACG CTA TTA GAC GTT AAG AAT TAT TCT CCT CTG CTT GCT    2195
Ala Leu Gln Thr Leu Leu Asp Val Lys Asn Tyr Ser Pro Leu Leu Ala
                500                 505                 510

TAC AAC AAA AAT AGT AAC GCA ATT GGG CAA AAC AGC TCT AGT ACA TTG    2243
Tyr Asn Lys Asn Ser Asn Ala Ile Gly Gln Asn Ser Ser Ser Thr Leu
                515                 520                 525

AAT TAC GGT AAC TTT TGT AAC GAT TTT TCA TTG AAA ATT GGT AAC TTG    2291
Asn Tyr Gly Asn Phe Cys Asn Asp Phe Ser Leu Lys Ile Gly Asn Leu
            530                 535                 540

ATT GTC CTT ACA AAA GAA TTA CTT CCA AGT ATT AAA ACT ACA TCC TAT    2339
```

-continued

| | |
|---|---|
| Ile Val Leu Thr Lys Glu Leu Leu Pro Ser Ile Lys Thr Thr Ser Tyr<br>545 550 555 | |
| GCA AAG AAA ATT AAG TTG AAA GTT AAA GCT TAT GCA GAA GCC ACA GGT<br>Ala Lys Lys Ile Lys Leu Lys Val Lys Ala Tyr Ala Glu Ala Thr Gly<br>560 565 570 575 | 2387 |
| ATA CCA TTC ACT GAC ATA TCT CCT CAA GTC ACT GCA ATG AGT CAT AAC<br>Ile Pro Phe Thr Asp Ile Ser Pro Gln Val Thr Ala Met Ser His Asn<br>580 585 590 | 2435 |
| AAT CTT CAA ACG ATT AAC AAC GAA AAT AAG AAC CCC CAT AAC AAA AAT<br>Asn Leu Gln Thr Ile Asn Asn Glu Asn Lys Asn Pro His Asn Lys Asn<br>595 600 605 | 2483 |
| AGT CAT AAT CAT AAT CAT AAT CAT AAT CAT AAC CAT GCT CAC AAT AAT<br>Ser His Asn His Asn His Asn His Asn His Asn His Ala His Asn Asn<br>610 615 620 | 2531 |
| AAT AAC AAT AAT AAT CAA AAG AGT CAT ACC CGT CAT TTT TCT TTA CCA<br>Asn Asn Asn Asn Asn Gln Lys Ser His Thr Arg His Phe Ser Leu Pro<br>625 630 635 | 2579 |
| GCT AAT GCT TAC CAT AGA AGA AGT AAC AGC TCT GTA ACC AAT AAT TTC<br>Ala Asn Ala Tyr His Arg Arg Ser Asn Ser Ser Val Thr Asn Asn Phe<br>640 645 650 655 | 2627 |
| TCA AAC CAA TAT GCA CAA GAT CAG AAA ATT CAC TCT CCG CAA CAA ATT<br>Ser Asn Gln Tyr Ala Gln Asp Gln Lys Ile His Ser Pro Gln Gln Ile<br>660 665 670 | 2675 |
| ATG AAC TTC AAC CAA AAC GCA TAT CCC TCG ATG GGA GCA CCT TCT TTC<br>Met Asn Phe Asn Gln Asn Ala Tyr Pro Ser Met Gly Ala Pro Ser Phe<br>675 680 685 | 2723 |
| AAT TCT CAA ACT AAC CCA CCA TTG GTA AGC CAT AAC TCG TTA CAA AAC<br>Asn Ser Gln Thr Asn Pro Pro Leu Val Ser His Asn Ser Leu Gln Asn<br>690 695 700 | 2771 |
| TTC GAC AAC CGC CAG TTT GCA AAT TTA ATG GCA CAT CCT AAT TCT GCT<br>Phe Asp Asn Arg Gln Phe Ala Asn Leu Met Ala His Pro Asn Ser Ala<br>705 710 715 | 2819 |
| GCA CCA ATC CAT TCG TTC TCA TCA TCT AAC ATT ACC AAT GTG AAT CCT<br>Ala Pro Ile His Ser Phe Ser Ser Ser Asn Ile Thr Asn Val Asn Pro<br>720 725 730 735 | 2867 |
| AAT GTT TCA AGG GGA TTT AAG CAG CCT GGA TTT ATG ATG AAT GAA ACC<br>Asn Val Ser Arg Gly Phe Lys Gln Pro Gly Phe Met Met Asn Glu Thr<br>740 745 750 | 2915 |
| GAC AAA ATT AAT GCT AAT CAC TTC TCG CCA TAC TCT AAT GCA AAT AGT<br>Asp Lys Ile Asn Ala Asn His Phe Ser Pro Tyr Ser Asn Ala Asn Ser<br>755 760 765 | 2963 |
| CAA AAC TTC AAT GAA TCT TTT GTG CCT CGT ATG CAA TAT CAA ACG GAA<br>Gln Asn Phe Asn Glu Ser Phe Val Pro Arg Met Gln Tyr Gln Thr Glu<br>770 775 780 | 3011 |
| GGT GCA AAC TGG GAT TCA AGT TTG TCA ATG AAG TCG CAG CAT ATT GGT<br>Gly Ala Asn Trp Asp Ser Ser Leu Ser Met Lys Ser Gln His Ile Gly<br>785 790 795 | 3059 |
| CAA GGC CCA TAT AAT CAA GTT AAT ATG AGC CGC AAC GCT AGT ATT TCC<br>Gln Gly Pro Tyr Asn Gln Val Asn Met Ser Arg Asn Ala Ser Ile Ser<br>800 805 810 815 | 3107 |
| AAT ATG CCT GCC ATG AAT ACC GCT AGA ACA TCT GAT GAA CTT CAA TTC<br>Asn Met Pro Ala Met Asn Thr Ala Arg Thr Ser Asp Glu Leu Gln Phe<br>820 825 830 | 3155 |
| ACT TTG CCA TAATACTTTT TTTTCTTTCT TTTCTTTCC TTCTTACTGT<br>Thr Leu Pro | 3204 |
| ACAAATATTT TACGCAGAAA TCAAAGACAA AAGAAAAATA AAAATAAAAA AATAAAAAAT | 3264 |
| TCAACTAAGC AATGACGTCC TACTAAAGTC CCAAAATTTG AGCCGGAAAA AAATGGTAAA | 3324 |
| GCAAACTATT GCCATCTTTA TATTTTGTAT TCTGTTTCCG AACACGTATC CAAAATCCTC | 3384 |
| CCACTGCCTT TGCAGGGTTA GCATTGCTCC CTACCAAAAT GATCTAATTT TTTTTTGAAT | 3444 |

-continued

```
CGTTTTTTGT C                                                3455
```

(2) INFORMATION FOR SEQ ID NO:4:

(i) SEQUENCE CHARACTERISTICS:
        (A) LENGTH: 834 amino acids
        (B) TYPE: amino acid
        (D) TOPOLOGY: linear (ii) MOLECULE TYPE: protein (xi) SEQUENCE DESCRIPTION: SEQ ID NO:4:

```
Met Ser Tyr Asn His Gln Pro Gln Leu Ser Ile Asn Ser Val Gln Ser
  1               5                  10                  15

Leu Leu Glu Pro Val Thr Pro Pro Leu Gly Gln Met Asn Asn Lys
             20                  25                  30

Arg Asn His Gln Lys Ala His Ser Leu Asp Leu Ser Gly Phe Asn Gln
             35                  40                  45

Phe Ile Ser Ser Thr Gln Ser Pro Leu Ala Leu Met Asn Asn Thr Ser
 50                  55                  60

Thr Ser Asn Ser Ala Asn Ser Phe Ser Pro Asn Pro Asn Ala Ala Ser
 65                  70                  75                  80

Asn Ser Thr Gly Leu Ser Ala Ser Met Ala Asn Pro Ala Ile Leu
             85                  90                  95

Pro Leu Ile Asn Glu Phe Asp Leu Glu Met Asp Gly Pro Arg Arg Lys
            100                 105                 110

Ser Ser His Asp Phe Thr Val Val Ala Pro Ser Asn Ser Gly Val Asn
            115                 120                 125

Thr Ser Ser Leu Ile Met Glu Thr Pro Ser Ser Ser Val Thr Pro Ala
            130                 135                 140

Ala Ser Leu Arg Asn Phe Ser Asn Ser Asn Asn Ala Ala Ser Lys Cys
145                 150                 155                 160

Gly Val Asp Asn Ser Ser Phe Gly Leu Ser Ser Ser Thr Ser Ser Ser
                165                 170                 175

Met Val Glu Ile Ser Ala Leu Pro Leu Arg Asp Leu Asp Tyr Ile Lys
                180                 185                 190

Leu Ala Thr Asp Gln Phe Gly Cys Arg Phe Leu Gln Lys Lys Leu Glu
                195                 200                 205

Thr Pro Ser Glu Ser Asn Met Val Arg Asp Leu Met Tyr Glu Gln Ile
            210                 215                 220

Lys Pro Phe Phe Leu Asp Leu Ile Leu Asp Pro Phe Gly Asn Tyr Leu
225                 230                 235                 240

Val Gln Lys Leu Cys Asp Tyr Leu Thr Ala Glu Gln Lys Thr Leu Leu
                245                 250                 255

Ile Gln Thr Ile Tyr Pro Asn Val Phe Gln Ile Ser Ile Asn Gln Tyr
                260                 265                 270

Gly Thr Arg Ser Leu Gln Lys Ile Ile Asp Thr Val Asp Asn Glu Val
                275                 280                 285

Gln Ile Asp Leu Ile Ile Lys Gly Phe Ser Gln Glu Phe Thr Ser Ile
            290                 295                 300

Glu Gln Val Val Thr Leu Ile Asn Asp Leu Asn Gly Asn His Val Ile
305                 310                 315                 320

Gln Lys Cys Ile Phe Lys Phe Ser Pro Ser Lys Phe Gly Phe Ile Ile
                325                 330                 335

Asp Ala Ile Val Glu Gln Asn Asn Ile Ile Thr Ile Ser Thr His Lys
                340                 345                 350
```

-continued

```
His Gly Cys Cys Val Leu Gln Lys Leu Leu Ser Val Cys Thr Leu Gln
            355                 360                 365

Gln Ile Phe Lys Ile Ser Val Lys Ile Val Gln Phe Leu Pro Gly Leu
            370                 375                 380

Ile Asn Asp Gln Phe Gly Asn Tyr Ile Ile Gln Phe Leu Leu Asp Ile
385                 390                 395                 400

Lys Glu Leu Asp Phe Tyr Leu Leu Ala Glu Leu Phe Asn Arg Leu Ser
                405                 410                 415

Asn Glu Leu Cys Gln Leu Ser Cys Leu Lys Phe Ser Ser Asn Val Val
            420                 425                 430

Glu Lys Phe Ile Lys Lys Leu Phe Arg Ile Ile Thr Gly Phe Ile Val
            435                 440                 445

Asn Asn Asn Gly Gly Ala Ser Gln Arg Thr Ala Val Ala Ser Asp Asp
            450                 455                 460

Val Ile Asn Ala Ser Met Asn Ile Leu Leu Thr Thr Ile Asp Ile Phe
465                 470                 475                 480

Thr Val Asn Leu Asn Val Leu Ile Arg Asp Asn Phe Gly Asn Tyr Ala
                485                 490                 495

Leu Gln Thr Leu Leu Asp Val Lys Asn Tyr Ser Pro Leu Leu Ala Tyr
            500                 505                 510

Asn Lys Asn Ser Asn Ala Ile Gly Gln Asn Ser Ser Thr Leu Asn
            515                 520                 525

Tyr Gly Asn Phe Cys Asn Asp Phe Ser Leu Lys Ile Gly Asn Leu Ile
            530                 535                 540

Val Leu Thr Lys Glu Leu Leu Pro Ser Ile Lys Thr Ser Tyr Ala
545                 550                 555                 560

Lys Lys Ile Lys Leu Lys Val Lys Ala Tyr Ala Glu Ala Thr Gly Ile
                565                 570                 575

Pro Phe Thr Asp Ile Ser Pro Gln Val Thr Ala Met Ser His Asn Asn
            580                 585                 590

Leu Gln Thr Ile Asn Asn Glu Asn Lys Asn Pro His Asn Lys Asn Ser
            595                 600                 605

His Asn His Asn His Asn His Asn His Ala His Asn Asn Asn
            610                 615                 620

Asn Asn Asn Asn Gln Lys Ser His Thr Arg His Phe Ser Leu Pro Ala
625                 630                 635                 640

Asn Ala Tyr His Arg Arg Ser Asn Ser Ser Val Thr Asn Asn Phe Ser
                645                 650                 655

Asn Gln Tyr Ala Gln Asp Gln Lys Ile His Ser Pro Gln Gln Ile Met
            660                 665                 670

Asn Phe Asn Gln Asn Ala Tyr Pro Ser Met Gly Ala Pro Ser Phe Asn
            675                 680                 685

Ser Gln Thr Asn Pro Pro Leu Val Ser His Asn Ser Leu Gln Asn Phe
            690                 695                 700

Asp Asn Arg Gln Phe Ala Asn Leu Met Ala His Pro Asn Ser Ala Ala
705                 710                 715                 720

Pro Ile His Ser Phe Ser Ser Asn Ile Thr Asn Val Asn Pro Asn
                725                 730                 735

Val Ser Arg Gly Phe Lys Gln Pro Gly Phe Met Met Asn Glu Thr Asp
            740                 745                 750

Lys Ile Asn Ala Asn His Phe Ser Pro Tyr Ser Asn Ala Asn Ser Gln
            755                 760                 765

Asn Phe Asn Glu Ser Phe Val Pro Arg Met Gln Tyr Gln Thr Glu Gly
```

```
                770              775              780
Ala Asn Trp Asp Ser Ser Leu Ser Met Lys Ser Gln His Ile Gly Gln
785              790              795              800

Gly Pro Tyr Asn Gln Val Asn Met Ser Arg Asn Ala Ser Ile Ser Asn
            805              810              815

Met Pro Ala Met Asn Thr Ala Arg Thr Ser Asp Glu Leu Gln Phe Thr
            820              825              830

Leu Pro
```

(2) INFORMATION FOR SEQ ID NO:5:

(i) SEQUENCE CHARACTERISTICS:
        (A) LENGTH: 4000 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 717..3380

(xi) SEQUENCE DESCRIPTION: SEQ ID NO:5:

```
GTGTCTTCCA TGGAGTGAAT TGTGATTTGT GAATTATATC TGTCCAATAC CGTTGCCTTG      60

TTGGGAGCTC AGATAGAAAA GACATCTTAA TTCCAGACAG TCTATTCTCT GTCTATTTCT     120

CTTTGTGACT GCAAATTTTA ATTTGTGACG CCTTTTCTTA TTACTCATGT ATTTGTCACT     180

CTTGACGATT GTTTTTTTTC TATATTTTTT TTGTTCTGGG GTCCTCCAGA GAATAAAAAA     240

TAATGATCAA TATAGTAGAT AGTATAGTTA TATTCTTATT CGTTGCACCT TGTTTAACAA     300

ATCACTCAGA CTCAAAGAGA ATATCGGTTG GTTATCTCTC TCCGAAGGTG AACAGCAAAC     360

AGTACCTCAC GTCTTTTTTT TGAATAGTTT TTTTTTTTGT TGAAACAGAA AAAAAACTTT     420

CTTCCGTATA TTACATTGTA CATTATTTTT ATTGTATTTT AGTTTCCAAC GTTAGGATTT     480

GAGCCGTCAT TAATATATT CGTTTTTGTA CACTATTCCA GACGATTTAT TTTTAGTACA     540

CTTAAAATTC CTGTTGATAT TGTCCACTAG TTCTCTTTTC ATATTTTATT TTCGCTTATT     600

CTTTAGGTTC TTTTAAGAGT CTCTGTTCAT TTTCCGTTCT TACTGTTTCT TTGTCCTCGA     660

TATCTTTTAA GAAAGAGAGA ACTAAGCGCT GTAACATTTT TAAGTGGACC TACGTT        716

ATG TCT ACA AAA GGT TTG AAA GAA GAA ATC GAT GAT GTA CCA TCA GTA      764
Met Ser Thr Lys Gly Leu Lys Glu Glu Ile Asp Asp Val Pro Ser Val
 1               5                  10                  15

GAC CCT GTC GTT TCA GAA ACA GTC AAT TCT GCT TTA GAG CAG TTG CAA      812
Asp Pro Val Val Ser Glu Thr Val Asn Ser Ala Leu Glu Gln Leu Gln
            20                  25                  30

CTA GAT GAT CCA GAG GAA AAC GCC ACC TCT AAT GCA TTT GCG AAT AAA      860
Leu Asp Asp Pro Glu Glu Asn Ala Thr Ser Asn Ala Phe Ala Asn Lys
        35                  40                  45

GTT TCT CAA GAT TCT CAA TTC GCT AAT GGC CCT CCG TCG CAA ATG TTT      908
Val Ser Gln Asp Ser Gln Phe Ala Asn Gly Pro Pro Ser Gln Met Phe
    50                  55                  60

CCA CAT CCA CAA ATG ATG GGT GGA ATG GGC TTC ATG CCC TAC TCT CAA      956
Pro His Pro Gln Met Met Gly Gly Met Gly Phe Met Pro Tyr Ser Gln
65                  70                  75                  80

ATG ATG CAG GTT CCT CAT AAT CCT TGT CCA TTT TTT CCG CCC CCT GAT     1004
Met Met Gln Val Pro His Asn Pro Cys Pro Phe Phe Pro Pro Pro Asp
                85                  90                  95

TTT AAT GAT CCA ACA GCA CCA TTG AGT AGC TCG CCC TTG AAT GCA GGC     1052
Phe Asn Asp Pro Thr Ala Pro Leu Ser Ser Ser Pro Leu Asn Ala Gly
```

-continued

|  | 100 | | | | 105 | | | | | 110 | | | |
|---|---|---|---|---|---|---|---|---|---|---|---|---|---|

```
GGT CCA CCA ATG TTA TTC AAG AAT GAC TCA CTT CCA TTT CAA ATG CTG      1100
Gly Pro Pro Met Leu Phe Lys Asn Asp Ser Leu Pro Phe Gln Met Leu
        115                 120                 125

TCT TCG GGT GCT GCG GTA GCA ACT CAA GGT GGA CAA AAT CTA AAC CCA      1148
Ser Ser Gly Ala Ala Val Ala Thr Gln Gly Gly Gln Asn Leu Asn Pro
130                 135                 140

TTG ATA AAT GAC AAT TCA ATG AAG GTA TTG CCA ATC GCA TCG GCT GAT      1196
Leu Ile Asn Asp Asn Ser Met Lys Val Leu Pro Ile Ala Ser Ala Asp
145                 150                 155                 160

CCG TTA TGG ACT CAT TCA AAC GTA CCA GGA TCA GCA TCT GTA GCC ATT      1244
Pro Leu Trp Thr His Ser Asn Val Pro Gly Ser Ala Ser Val Ala Ile
            165                 170                 175

GAA GAA ACC ACC GCT ACT CTA CAA GAA AGC CTA CCA TCT AAG GGC AGG      1292
Glu Glu Thr Thr Ala Thr Leu Gln Glu Ser Leu Pro Ser Lys Gly Arg
                180                 185                 190

GAG TCT AAT AAT AAG GCT AGT TCG TTC AGA AGA CAA ACT TTT CAT GCT      1340
Glu Ser Asn Asn Lys Ala Ser Ser Phe Arg Arg Gln Thr Phe His Ala
                    195                 200                 205

TTA TCA CCA ACT GAC CTT ATC AAT GCG GCC AAC AAT GTA ACC TTG TCA      1388
Leu Ser Pro Thr Asp Leu Ile Asn Ala Ala Asn Asn Val Thr Leu Ser
210                 215                 220

AAG GAC TTC CAA TCT GAC ATG CAG AAT TTT TCT AAG GCT AAG AAA CCG      1436
Lys Asp Phe Gln Ser Asp Met Gln Asn Phe Ser Lys Ala Lys Lys Pro
225                 230                 235                 240

TCT GTA GGA GCT AAC AAT ACT GCA AAA ACC AGA ACT CAA TCC ATA TCT      1484
Ser Val Gly Ala Asn Asn Thr Ala Lys Thr Arg Thr Gln Ser Ile Ser
            245                 250                 255

TTT GAT AAT ACT CCC TCC TCA ACG TCA TTT ATA CCC CCA ACC AAT AGT      1532
Phe Asp Asn Thr Pro Ser Ser Thr Ser Phe Ile Pro Pro Thr Asn Ser
                260                 265                 270

GTT TCT GAG AAA TTA TCC GAT TTC AAA ATA GAA ACC TCG AAG GAG GAT      1580
Val Ser Glu Lys Leu Ser Asp Phe Lys Ile Glu Thr Ser Lys Glu Asp
                    275                 280                 285

TTG ATT AAT AAA ACT GCA CCA GCT AAA AAA GAG AGT CCT ACA ACT TAT      1628
Leu Ile Asn Lys Thr Ala Pro Ala Lys Lys Glu Ser Pro Thr Thr Tyr
290                 295                 300

GGT GCA GCA TAT CCA TAT GGG GGA CCT TTA CTT CAA CCA AAT CCT ATT      1676
Gly Ala Ala Tyr Pro Tyr Gly Gly Pro Leu Leu Gln Pro Asn Pro Ile
305                 310                 315                 320

ATG CCA GGC CAC CCA CAT AAT ATA TCC TCC CCT ATC TAT GGT ATT AGA      1724
Met Pro Gly His Pro His Asn Ile Ser Ser Pro Ile Tyr Gly Ile Arg
            325                 330                 335

TCA CCT TTT CCT AAT TCT TAT GAA ATG GGC GCG CAA TTT CAA CCT TTC      1772
Ser Pro Phe Pro Asn Ser Tyr Glu Met Gly Ala Gln Phe Gln Pro Phe
                340                 345                 350

TCT CCG ATT TTA AAT CCT ACG AGT CAT TCA CTA AAT GCA AAT TCT CCA      1820
Ser Pro Ile Leu Asn Pro Thr Ser His Ser Leu Asn Ala Asn Ser Pro
                    355                 360                 365

ATT CCT CTA ACC CAA TCG CCA ATT CAT CTT GCA CCA GTT TTA AAC CCT      1868
Ile Pro Leu Thr Gln Ser Pro Ile His Leu Ala Pro Val Leu Asn Pro
370                 375                 380

AGT TCA AAT TCT GTT GCC TTT TCA GAT ATG AAG AAT GAT GGT GGT AAG      1916
Ser Ser Asn Ser Val Ala Phe Ser Asp Met Lys Asn Asp Gly Gly Lys
385                 390                 395                 400

CCC ACC ACC GAT AAC GAC AAG GCG GGT CCA AAT GTT AGG ATG GAT TTA      1964
Pro Thr Thr Asp Asn Asp Lys Ala Gly Pro Asn Val Arg Met Asp Leu
            405                 410                 415

ATA AAT CCT AAT CTT GGG CCA TCA ATG CAA CCT TTC CAC ATA TTA CCT      2012
Ile Asn Pro Asn Leu Gly Pro Ser Met Gln Pro Phe His Ile Leu Pro
```

-continued

```
                   420                  425                    430
CCC CAG CAA AAC ACC CCC CCT CCT CCC TGG CTT TAT AGC ACT CCA CCT        2060
Pro Gln Gln Asn Thr Pro Pro Pro Pro Trp Leu Tyr Ser Thr Pro Pro
        435                 440                 445

CCC TTC AAC GCA ATG GTT CCG CCT CAT TTG TTG GCT CAA AAT CAT ATG        2108
Pro Phe Asn Ala Met Val Pro Pro His Leu Leu Ala Gln Asn His Met
    450                 455                 460

CCG TTA ATG AAT AGC GCC AAT AAT AAA CAT CAT GGT CGT AAT AAC AAT        2156
Pro Leu Met Asn Ser Ala Asn Asn Lys His His Gly Arg Asn Asn Asn
465                 470                 475                 480

AGC ATG TCA AGT CAT AAT GAC AAT GAC AAC ATT GGT AAT TCT AAT TAC        2204
Ser Met Ser Ser His Asn Asp Asn Asp Asn Ile Gly Asn Ser Asn Tyr
            485                 490                 495

AAC AAT AAA GAC ACA GGT CGT TCT AAC GTT GGT AAA ATG AAA AAT ATG        2252
Asn Asn Lys Asp Thr Gly Arg Ser Asn Val Gly Lys Met Lys Asn Met
                500                 505                 510

AAA AAC AGT TAT CAT GGC TAC TAT AAT AAC AAT AAT AAT AAT AAT AAT        2300
Lys Asn Ser Tyr His Gly Tyr Tyr Asn Asn Asn Asn Asn Asn Asn Asn
            515                 520                 525

AAT AAC AAT AAT AAT AAT AAC AGT AAT GCT ACC AAC AGC AAC AGC GCG        2348
Asn Asn Asn Asn Asn Asn Ser Asn Ala Thr Asn Ser Asn Ser Ala
530                 535                 540

GAA AAA CAA CGT AAA ATT GAG GAG TCG TCG AGA TTT GCG GAC GCA GTT        2396
Glu Lys Gln Arg Lys Ile Glu Glu Ser Ser Arg Phe Ala Asp Ala Val
545                 550                 555                 560

TTA GAC CAA TAT ATC GGA AGT ATT CAC TCA TTG TGT AAA GAC CAA CAT        2444
Leu Asp Gln Tyr Ile Gly Ser Ile His Ser Leu Cys Lys Asp Gln His
            565                 570                 575

GGT TGT CGT TTT CTG CAA AAG CAG TTG GAT ATT CTC GGC AGT AAG GCG        2492
Gly Cys Arg Phe Leu Gln Lys Gln Leu Asp Ile Leu Gly Ser Lys Ala
                580                 585                 590

GCG GAC CGA ATT TTT GAA GAA ACT AAG GAT TAT ACG GTT GAA TTG ATG        2540
Ala Asp Arg Ile Phe Glu Glu Thr Lys Asp Tyr Thr Val Glu Leu Met
            595                 600                 605

ACT GAT TCA TTC GGT AAT TAT TTG ATC CAG AAG CTA TTG GAA GAG GTT        2588
Thr Asp Ser Phe Gly Asn Tyr Leu Ile Gln Lys Leu Leu Glu Glu Val
        610                 615                 620

ACC ACA GAA CAA AGA ATC GTA CTC ACA AAA ATA TCT TCC CCT CAT TTT        2636
Thr Thr Glu Gln Arg Ile Val Leu Thr Lys Ile Ser Ser Pro His Phe
625                 630                 635                 640

GTC GAA ATT TCC TTA AAC CCT CAT GGT ACT AGG GCA TTA CAA AAA CTC        2684
Val Glu Ile Ser Leu Asn Pro His Gly Thr Arg Ala Leu Gln Lys Leu
            645                 650                 655

ATT GAA TGC ATC AAA ACA GAT GAA GAA GCA CAG ATT GTT GTT GAT TCT        2732
Ile Glu Cys Ile Lys Thr Asp Glu Glu Ala Gln Ile Val Val Asp Ser
                660                 665                 670

TTA CGC CCT TAT ACT GTC CAG TTG AGT AAG GAT TTA AAT GGT AAT CAT        2780
Leu Arg Pro Tyr Thr Val Gln Leu Ser Lys Asp Leu Asn Gly Asn His
            675                 680                 685

GTT ATT CAA AAA TGT TTG CAA AGG TTG AAG CCT GAA AAC TTC CAG TTT        2828
Val Ile Gln Lys Cys Leu Gln Arg Leu Lys Pro Glu Asn Phe Gln Phe
        690                 695                 700

ATC TTT GAC GCA ATC TCT GAT AGC TGT ATT GAT ATT GCT ACT CAT AGA        2876
Ile Phe Asp Ala Ile Ser Asp Ser Cys Ile Asp Ile Ala Thr His Arg
705                 710                 715                 720

CAC GGG TGT TGC GTT TTG CAA CGT TGT CTA GAT CAT GGG ACT ACA GAA        2924
His Gly Cys Cys Val Leu Gln Arg Cys Leu Asp His Gly Thr Thr Glu
            725                 730                 735

CAA TGT GAC AAT CTG TGT GAT AAG TTG CTA GCC CTT GTT GAT AAA TTA        2972
Gln Cys Asp Asn Leu Cys Asp Lys Leu Leu Ala Leu Val Asp Lys Leu
```

```
                740                 745                 750
ACT TTG GAT CCA TTT GGC AAC TAT GTG GTG CAA TAT ATA ATT ACC AAA        3020
Thr Leu Asp Pro Phe Gly Asn Tyr Val Val Gln Tyr Ile Ile Thr Lys
            755                 760                 765

GAG GCT GAG AAG AAC AAA TAT GAT TAT ACG CAT AAA ATT GTC CAC CTG        3068
Glu Ala Glu Lys Asn Lys Tyr Asp Tyr Thr His Lys Ile Val His Leu
        770                 775                 780

TTG AAA CCA AGA GCC ATC GAA CTT TCT ATC CAT AAA TTT GGA TCA AAT        3116
Leu Lys Pro Arg Ala Ile Glu Leu Ser Ile His Lys Phe Gly Ser Asn
785                 790                 795                 800

GTG ATT GAA AAA ATC TTG AAG ACA GCT ATT GTT TCG GAG CCA ATG ATT        3164
Val Ile Glu Lys Ile Leu Lys Thr Ala Ile Val Ser Glu Pro Met Ile
                805                 810                 815

CTG GAA ATT TTA AAT AAT GGT GGC GAG ACG GGT ATT CAA TCA TTG TTG        3212
Leu Glu Ile Leu Asn Asn Gly Gly Glu Thr Gly Ile Gln Ser Leu Leu
            820                 825                 830

AAT GAT AGC TAC GGA AAT TAC GTT TTA CAG ACA GCA TTA GAC ATT TCT        3260
Asn Asp Ser Tyr Gly Asn Tyr Val Leu Gln Thr Ala Leu Asp Ile Ser
        835                 840                 845

CAT AAG CAA AAT GAC TAT CTC TAT AAA AGA CTA TCA GAG ATT GTG GCG        3308
His Lys Gln Asn Asp Tyr Leu Tyr Lys Arg Leu Ser Glu Ile Val Ala
850                 855                 860

CCT TTA CTG GTG GGC CCC ATA AGA AAT ACA CCT CAT GGT AAA AGA ATC        3356
Pro Leu Leu Val Gly Pro Ile Arg Asn Thr Pro His Gly Lys Arg Ile
865                 870                 875                 880

ATC GGA ATG TTA CAT TTA GAT TCA TAGTTGATAC ATATATCCTC AGTTTAGCTT       3410
Ile Gly Met Leu His Leu Asp Ser
                885

TTTTTACGTT AGCCTCATAT AATATCTTTT GTACAATACT AAAATACATC ATTTTTTTT       3470

TCGTTGAGGA TCAAATGAAT ATCCAAAGCA AAAAAAATAG GAATTTTCAC TTTATGGTAT      3530

ACTGGTAAAT AGTGTTGAAG AAATAAGAGA AGGAGATCGC CCTAGAAAAC AGAATGTTCT      3590

TATTTAAATA AGTAAACTCA AAAGAAAAA AAAAGGAAGG AAGTTTTTGA GAACTTTTAT       3650

CTATACAAAC GTATACGTTT AACTATCTGG ATAAACGTCG CTCCACAGGA TACTGTAGAG      3710

GTCCTCAAGA TCACCGTTAT TAACAAATTC ATCTAGTGTC CCCAAATTAA AACTAGTTGC      3770

AGAAAAATTG TTACTGTTGT TGTTGTTAAT ATTGTTAATA TTGTTTTTAT TGTTGTTGTT      3830

GTTGATTTCA TTTGTGTTCA TAAATGGTAC TTGTACTGAA GTGGGTATTT GCTGCTGAGC      3890

ATTGATTGGT TTATTAGATT GGACTTGCGA ATTATTTTGC CCATTTGTTG GTTGCGCGTA      3950

ATCGGGATTG ATCATATCAG ACACGGATAA TGACCTAAAT GAAGGCAATT                4000

(2) INFORMATION FOR SEQ ID NO:6:

(i) SEQUENCE CHARACTERISTICS:
        (A) LENGTH: 888 amino acids
        (B) TYPE: amino acid
        (D) TOPOLOGY: linear (ii) MOLECULE TYPE: protein (xi) SEQUENCE DESCRIPTION: SEQ ID NO:6:

Met Ser Thr Lys Gly Leu Lys Glu Glu Ile Asp Asp Val Pro Ser Val
 1               5                  10                  15

Asp Pro Val Val Ser Glu Thr Val Asn Ser Ala Leu Glu Gln Leu Gln
                20                  25                  30

Leu Asp Asp Pro Glu Glu Asn Ala Thr Ser Asn Ala Phe Ala Asn Lys
        35                  40                  45

Val Ser Gln Asp Ser Gln Phe Ala Asn Gly Pro Pro Ser Gln Met Phe
```

```
            50                  55                  60
Pro His Pro Gln Met Met Gly Gly Met Gly Phe Met Pro Tyr Ser Gln
 65                  70                  75                  80

Met Met Gln Val Pro His Asn Pro Cys Pro Phe Phe Pro Pro Pro Asp
                 85                  90                  95

Phe Asn Asp Pro Thr Ala Pro Leu Ser Ser Pro Leu Asn Ala Gly
                100                 105                 110

Gly Pro Pro Met Leu Phe Lys Asn Asp Ser Leu Pro Phe Gln Met Leu
            115                 120                 125

Ser Ser Gly Ala Ala Val Ala Thr Gln Gly Gly Gln Asn Leu Asn Pro
        130                 135                 140

Leu Ile Asn Asp Asn Ser Met Lys Val Leu Pro Ile Ala Ser Ala Asp
145                 150                 155                 160

Pro Leu Trp Thr His Ser Asn Val Pro Gly Ser Ala Ser Val Ala Ile
                165                 170                 175

Glu Glu Thr Thr Ala Thr Leu Gln Glu Ser Leu Pro Ser Lys Gly Arg
                180                 185                 190

Glu Ser Asn Asn Lys Ala Ser Ser Phe Arg Arg Gln Thr Phe His Ala
                195                 200                 205

Leu Ser Pro Thr Asp Leu Ile Asn Ala Ala Asn Asn Val Thr Leu Ser
        210                 215                 220

Lys Asp Phe Gln Ser Asp Met Gln Asn Phe Ser Lys Ala Lys Lys Pro
225                 230                 235                 240

Ser Val Gly Ala Asn Asn Thr Ala Lys Thr Arg Thr Gln Ser Ile Ser
                245                 250                 255

Phe Asp Asn Thr Pro Ser Ser Thr Ser Phe Ile Pro Pro Thr Asn Ser
                260                 265                 270

Val Ser Glu Lys Leu Ser Asp Phe Lys Ile Glu Thr Ser Lys Glu Asp
                275                 280                 285

Leu Ile Asn Lys Thr Ala Pro Ala Lys Lys Glu Ser Pro Thr Thr Tyr
        290                 295                 300

Gly Ala Ala Tyr Pro Tyr Gly Gly Pro Leu Leu Gln Pro Asn Pro Ile
305                 310                 315                 320

Met Pro Gly His Pro His Asn Ile Ser Ser Pro Ile Tyr Gly Ile Arg
                325                 330                 335

Ser Pro Phe Pro Asn Ser Tyr Glu Met Gly Ala Gln Phe Gln Pro Phe
                340                 345                 350

Ser Pro Ile Leu Asn Pro Thr Ser His Ser Leu Asn Ala Asn Ser Pro
            355                 360                 365

Ile Pro Leu Thr Gln Ser Pro Ile His Leu Ala Pro Val Leu Asn Pro
        370                 375                 380

Ser Ser Asn Ser Val Ala Phe Ser Asp Met Lys Asn Asp Gly Gly Lys
385                 390                 395                 400

Pro Thr Thr Asp Asn Asp Lys Ala Gly Pro Asn Val Arg Met Asp Leu
                405                 410                 415

Ile Asn Pro Asn Leu Gly Pro Ser Met Gln Pro Phe His Ile Leu Pro
                420                 425                 430

Pro Gln Gln Asn Thr Pro Pro Pro Trp Leu Tyr Ser Thr Pro Pro
            435                 440                 445

Pro Phe Asn Ala Met Val Pro Pro His Leu Leu Ala Gln Asn His Met
        450                 455                 460

Pro Leu Met Asn Ser Ala Asn Asn Lys His His Gly Arg Asn Asn Asn
465                 470                 475                 480
```

```
Ser Met Ser Ser His Asn Asp Asn Asp Asn Ile Gly Asn Ser Asn Tyr
            485                 490                 495

Asn Asn Lys Asp Thr Gly Arg Ser Asn Val Gly Lys Met Lys Asn Met
            500                 505                 510

Lys Asn Ser Tyr His Gly Tyr Tyr Asn Asn Asn Asn Asn Asn Asn Asn
            515                 520                 525

Asn Asn Asn Asn Asn Asn Ser Asn Ala Thr Asn Ser Asn Ser Ala
530                 535                 540

Glu Lys Gln Arg Lys Ile Glu Ser Ser Arg Phe Ala Asp Ala Val
545                 550                 555                 560

Leu Asp Gln Tyr Ile Gly Ser Ile His Ser Leu Cys Lys Asp Gln His
            565                 570                 575

Gly Cys Arg Phe Leu Gln Lys Gln Leu Asp Ile Leu Gly Ser Lys Ala
            580                 585                 590

Ala Asp Arg Ile Phe Glu Glu Thr Lys Asp Tyr Thr Val Glu Leu Met
            595                 600                 605

Thr Asp Ser Phe Gly Asn Tyr Leu Ile Gln Lys Leu Leu Glu Glu Val
            610                 615                 620

Thr Thr Glu Gln Arg Ile Val Leu Thr Lys Ile Ser Ser Pro His Phe
625                 630                 635                 640

Val Glu Ile Ser Leu Asn Pro His Gly Thr Arg Ala Leu Gln Lys Leu
            645                 650                 655

Ile Glu Cys Ile Lys Thr Asp Glu Glu Ala Gln Ile Val Val Asp Ser
            660                 665                 670

Leu Arg Pro Tyr Thr Val Gln Leu Ser Lys Asp Leu Asn Gly Asn His
            675                 680                 685

Val Ile Gln Lys Cys Leu Gln Arg Leu Lys Pro Glu Asn Phe Gln Phe
            690                 695                 700

Ile Phe Asp Ala Ile Ser Asp Ser Cys Ile Asp Ile Ala Thr His Arg
705                 710                 715                 720

His Gly Cys Cys Val Leu Gln Arg Cys Leu Asp His Gly Thr Thr Glu
            725                 730                 735

Gln Cys Asp Asn Leu Cys Asp Lys Leu Leu Ala Leu Val Asp Lys Leu
            740                 745                 750

Thr Leu Asp Pro Phe Gly Asn Tyr Val Val Gln Tyr Ile Ile Thr Lys
            755                 760                 765

Glu Ala Glu Lys Asn Lys Tyr Asp Tyr Thr His Lys Ile Val His Leu
770                 775                 780

Leu Lys Pro Arg Ala Ile Glu Leu Ser Ile His Lys Phe Gly Ser Asn
785                 790                 795                 800

Val Ile Glu Lys Ile Leu Lys Thr Ala Ile Val Ser Glu Pro Met Ile
            805                 810                 815

Leu Glu Ile Leu Asn Asn Gly Gly Glu Thr Gly Ile Gln Ser Leu Leu
            820                 825                 830

Asn Asp Ser Tyr Gly Asn Tyr Val Leu Gln Thr Ala Leu Asp Ile Ser
            835                 840                 845

His Lys Gln Asn Asp Tyr Leu Tyr Lys Arg Leu Ser Glu Ile Val Ala
            850                 855                 860

Pro Leu Leu Val Gly Pro Ile Arg Asn Thr Pro His Gly Lys Arg Ile
865                 870                 875                 880

Ile Gly Met Leu His Leu Asp Ser
            885
```

(2) INFORMATION FOR SEQ ID NO:7:

(i) SEQUENCE CHARACTERISTICS:
    (A) LENGTH: 5319 base pairs
    (B) TYPE: nucleic acid
    (C) STRANDEDNESS: double
    (D) TOPOLOGY: linear (ii) MOLECULE TYPE: DNA (genomic)

(ix) FEATURE:
    (A) NAME/KEY: CDS
    (B) LOCATION: 57..3614

(xi) SEQUENCE DESCRIPTION: SEQ ID NO:7:

```
GAAGATCGGG GGGCTGAAAT CCATCTTCAT CCTACCGCTC CGCCCGTGTT GGTGGA                    56

ATG AGC GTT GCA TGT GTC TTG AAG AGA AAA GCA GTG CTT TGG CAG GAC                 104
Met Ser Val Ala Cys Val Leu Lys Arg Lys Ala Val Leu Trp Gln Asp
  1               5                  10                  15

TCT TTC AGC CCC CAC CTG AAA CAT CAC CCT CAA GAA CCA GCT AAT CCC                 152
Ser Phe Ser Pro His Leu Lys His His Pro Gln Glu Pro Ala Asn Pro
             20                  25                  30

AAC ATG CCT GTT GTT TTG ACA TCT GGA ACA GGG TCG CAA GCG CAG CCA                 200
Asn Met Pro Val Val Leu Thr Ser Gly Thr Gly Ser Gln Ala Gln Pro
         35                  40                  45

CAA CCA GCT GCA AAT CAG GCT CTT GCA GCT GGG ACT CAC TCC AGC CCT                 248
Gln Pro Ala Ala Asn Gln Ala Leu Ala Ala Gly Thr His Ser Ser Pro
     50                  55                  60

GTC CCA GGA TCT ATA GGA GTT GCA GGC CGT TCC CAG GAC GAC GCT ATG                 296
Val Pro Gly Ser Ile Gly Val Ala Gly Arg Ser Gln Asp Asp Ala Met
 65                  70                  75                  80

GTG GAC TAC TTC TTT CAG AGG CAG CAT GGT GAG CAG CTT GGG GGA GGA                 344
Val Asp Tyr Phe Phe Gln Arg Gln His Gly Glu Gln Leu Gly Gly Gly
                 85                  90                  95

GGA AGT GGA GGA GGC GGC TAT AAT AAT AGC AAA CAT CGA TGG CCT ACT                 392
Gly Ser Gly Gly Gly Gly Tyr Asn Asn Ser Lys His Arg Trp Pro Thr
            100                 105                 110

GGG GAT AAC ATT CAT GCA GAA CAT CAG GTG CGT TCC ATG GAT GAA CTG                 440
Gly Asp Asn Ile His Ala Glu His Gln Val Arg Ser Met Asp Glu Leu
        115                 120                 125

AAT CAT GAT TTT CAA GCA CTT GCT CTG GAG GGA AGA GCG ATG GGA GAG                 488
Asn His Asp Phe Gln Ala Leu Ala Leu Glu Gly Arg Ala Met Gly Glu
    130                 135                 140

CAG CTC TTG CCA GGT AAA AAG TTT TGG GAA ACA GAT GAA TCC AGC AAA                 536
Gln Leu Leu Pro Gly Lys Lys Phe Trp Glu Thr Asp Glu Ser Ser Lys
145                 150                 155                 160

GAT GGA CCA AAA GGA ATA TTC CTG GGT GAT CAA TGG CGA GAC AGT GCC                 584
Asp Gly Pro Lys Gly Ile Phe Leu Gly Asp Gln Trp Arg Asp Ser Ala
                165                 170                 175

TGG GGA ACA TCA GAT CAT TCA GTT TCC CAG CCA ATC ATG GTG CAG AGA                 632
Trp Gly Thr Ser Asp His Ser Val Ser Gln Pro Ile Met Val Gln Arg
            180                 185                 190

AGA CCT GGT CAG AGT TTC CAT GTG AAC AGT GAG GTC AAT TCT GTA CTG                 680
Arg Pro Gly Gln Ser Phe His Val Asn Ser Glu Val Asn Ser Val Leu
        195                 200                 205

TCC CCA CGA TCG GAG AGT GGG GGA CTA GGC GTT AGC ATG GTG GAG TAT                 728
Ser Pro Arg Ser Glu Ser Gly Gly Leu Gly Val Ser Met Val Glu Tyr
    210                 215                 220

GTG TTG AGC TCA TCC CCG GGC GAT TCC TGT CTA AGA AAA GGA GGA TTT                 776
Val Leu Ser Ser Ser Pro Gly Asp Ser Cys Leu Arg Lys Gly Gly Phe
225                 230                 235                 240

GGC CCA AGG GAT GCA GAC AGT GAT GAA AAC GAC AAA GGT GAA AAG AAG                 824
Gly Pro Arg Asp Ala Asp Ser Asp Glu Asn Asp Lys Gly Glu Lys Lys
                245                 250                 255
```

```
AAC AAG GGT ACG TTT GAT GGA GAT AAG CTA GGA GAT TTG AAG GAG GAG           872
Asn Lys Gly Thr Phe Asp Gly Asp Lys Leu Gly Asp Leu Lys Glu Glu
            260                 265                 270

GGT GAT GTG ATG GAC AAG ACC AAT GGT TTA CCA GTG CAG AAT GGG ATT           920
Gly Asp Val Met Asp Lys Thr Asn Gly Leu Pro Val Gln Asn Gly Ile
        275                 280                 285

GAT GCA GAC GTC AAA GAT TTT AGC CGT ACC CCT GGT AAT TGC CAG AAC           968
Asp Ala Asp Val Lys Asp Phe Ser Arg Thr Pro Gly Asn Cys Gln Asn
    290                 295                 300

TCT GCT AAT GAA GTG GAT CTT CTG GGT CCA AAC CAG AAT GGT TCT GAG          1016
Ser Ala Asn Glu Val Asp Leu Leu Gly Pro Asn Gln Asn Gly Ser Glu
305                 310                 315                 320

GGC TTA GCC CAG CTG ACC AGC ACC AAT GGT GCC AAG CCT GTG GAG GAT          1064
Gly Leu Ala Gln Leu Thr Ser Thr Asn Gly Ala Lys Pro Val Glu Asp
                325                 330                 335

TTC TCC AAC ATG GAG TCC CAG AGT GTC CCC TTG GAC CCC ATG GAA CAT          1112
Phe Ser Asn Met Glu Ser Gln Ser Val Pro Leu Asp Pro Met Glu His
            340                 345                 350

GTG GGC ATG GAG CCT CTT CAG TTT GAT TAT TCA GGC ACG CAG GTA CCT          1160
Val Gly Met Glu Pro Leu Gln Phe Asp Tyr Ser Gly Thr Gln Val Pro
        355                 360                 365

GTG GAC TCA GCA GCA GCA ACT GTG GGA CTT TTT GAC TAC AAT TCT CAA          1208
Val Asp Ser Ala Ala Ala Thr Val Gly Leu Phe Asp Tyr Asn Ser Gln
    370                 375                 380

CAA CAG CTG TTC CAA AGA CCT AAT GCG CTT GCT GTC CAG CAG TTG ACA          1256
Gln Gln Leu Phe Gln Arg Pro Asn Ala Leu Ala Val Gln Gln Leu Thr
385                 390                 395                 400

GCT GCT CAG CAG CAG CAG TAT GCA CTG GCA GCT GCT CAT CAG CCG CAC          1304
Ala Ala Gln Gln Gln Gln Tyr Ala Leu Ala Ala Ala His Gln Pro His
                405                 410                 415

ATC GGT TTA GCT CCC GCT GCG TTT GTC CCC AAT CCA TAC ATC ATC AGC          1352
Ile Gly Leu Ala Pro Ala Ala Phe Val Pro Asn Pro Tyr Ile Ile Ser
            420                 425                 430

GCT GCT CCC CCA GGG ACG GAC CCC TAC ACA GCT GGA TTG GCT GCA GCA          1400
Ala Ala Pro Pro Gly Thr Asp Pro Tyr Thr Ala Gly Leu Ala Ala Ala
        435                 440                 445

GCG ACA CTA GGC CCA GCT GTG GTC CCT CAC CAG TAT TAT GGA GTT ACT          1448
Ala Thr Leu Gly Pro Ala Val Val Pro His Gln Tyr Tyr Gly Val Thr
    450                 455                 460

CCC TGG GGA GTC TAC CCT GCC AGT CTT TTC CAG CAG CAA GCT GCC GCT          1496
Pro Trp Gly Val Tyr Pro Ala Ser Leu Phe Gln Gln Gln Ala Ala Ala
465                 470                 475                 480

GCC GCT GCA GCA ACT AAT TCA GCT AAT CAA CAG ACC ACC CCA CAG GCT          1544
Ala Ala Ala Ala Thr Asn Ser Ala Asn Gln Gln Thr Thr Pro Gln Ala
                485                 490                 495

CAG CAA GGA CAG CAG CAG GTT CTC CGT GGA GGA GCC AGC CAA CGT CCT          1592
Gln Gln Gly Gln Gln Gln Val Leu Arg Gly Gly Ala Ser Gln Arg Pro
            500                 505                 510

TTG ACC CCA AAC CAG AAC CAG CAG GGA CAG CAA ACG GAT CCC CTT GTG          1640
Leu Thr Pro Asn Gln Asn Gln Gln Gly Gln Gln Thr Asp Pro Leu Val
        515                 520                 525

GCA GCT GCA GCA GTG AAT TCT GCC CTT GCA TTT GGA CAA GGT CTG GCA          1688
Ala Ala Ala Ala Val Asn Ser Ala Leu Ala Phe Gly Gln Gly Leu Ala
    530                 535                 540

GCA GGC ATG CCA GGT TAT CCG GTG TTG GCT CCT GCT GCT TAC TAT GAC          1736
Ala Gly Met Pro Gly Tyr Pro Val Leu Ala Pro Ala Ala Tyr Tyr Asp
545                 550                 555                 560

CAA ACT GGT GCC CTT GTA GTG AAT GCA GGC GCG AGA AAT GGT CTT GGA          1784
Gln Thr Gly Ala Leu Val Val Asn Ala Gly Ala Arg Asn Gly Leu Gly
                565                 570                 575
```

-continued

| | |
|---|---|
| GCT CCT GTT CGA CTT GTA GCT CCT GCC CCA GTC ATC ATT AGT TCC TCA<br>Ala Pro Val Arg Leu Val Ala Pro Ala Pro Val Ile Ile Ser Ser Ser<br>580 585 590 | 1832 |
| GCT GCA CAA GCA GCT GTT GCA GCA GCC GCA GCT TCA GCA AAT GGA GCA<br>Ala Ala Gln Ala Ala Val Ala Ala Ala Ala Ala Ser Ala Asn Gly Ala<br>595 600 605 | 1880 |
| GCT GGT GGT CTT GCT GGA ACA ACA AAT GGA CCA TTT CGC CCT TTA GGA<br>Ala Gly Gly Leu Ala Gly Thr Thr Asn Gly Pro Phe Arg Pro Leu Gly<br>610 615 620 | 1928 |
| ACA CAG CAG CCT CAG CCC CAG CCC CAG CAG CAG CCC AAT AAC AAC CTG<br>Thr Gln Gln Pro Gln Pro Gln Pro Gln Gln Gln Pro Asn Asn Asn Leu<br>625 630 635 640 | 1976 |
| GCA TCC AGT TCT TTC TAC GGC AAC AAC TCT CTG AAC AGC AAT TCA CAG<br>Ala Ser Ser Ser Phe Tyr Gly Asn Asn Ser Leu Asn Ser Asn Ser Gln<br>645 650 655 | 2024 |
| AGC AGC TCC CTC TTC TCC CAG GGC TCT GCC CAG CCT GCC AAC ACA TCC<br>Ser Ser Ser Leu Phe Ser Gln Gly Ser Ala Gln Pro Ala Asn Thr Ser<br>660 665 670 | 2072 |
| TTG GGA TTC GGA AGT AGC AGT TCT CTC GGC GCC ACC CTG GGA TCC GCC<br>Leu Gly Phe Gly Ser Ser Ser Ser Leu Gly Ala Thr Leu Gly Ser Ala<br>675 680 685 | 2120 |
| CTT GGA GGG TTT GGA ACA GCA GTT GCA AAC TCC AAC ACT GGC AGT GGC<br>Leu Gly Gly Phe Gly Thr Ala Val Ala Asn Ser Asn Thr Gly Ser Gly<br>690 695 700 | 2168 |
| TCC CGC CGT GAC TCC CTG ACT GGC AGC AGT GAC CTT TAT AAG AGG ACA<br>Ser Arg Arg Asp Ser Leu Thr Gly Ser Ser Asp Leu Tyr Lys Arg Thr<br>705 710 715 720 | 2216 |
| TCG AGC AGC TTG ACC CCC ATT GGA CAC AGT TTT TAT AAC GGC CTT AGC<br>Ser Ser Ser Leu Thr Pro Ile Gly His Ser Phe Tyr Asn Gly Leu Ser<br>725 730 735 | 2264 |
| TTT TCC TCC TCT CCT GGA CCC GTG GGC ATG CCT CTC CCT AGT CAG GGA<br>Phe Ser Ser Ser Pro Gly Pro Val Gly Met Pro Leu Pro Ser Gln Gly<br>740 745 750 | 2312 |
| CCA GGA CAT TCA CAG ACA CCA CCT CCT TCC CTC TCT TCA CAT GGA TCC<br>Pro Gly His Ser Gln Thr Pro Pro Pro Ser Leu Ser Ser His Gly Ser<br>755 760 765 | 2360 |
| TCT TCA AGC TTA AAC CTG GGA GGA CTC ACG AAT GGC AGT GGA AGA TAC<br>Ser Ser Ser Leu Asn Leu Gly Gly Leu Thr Asn Gly Ser Gly Arg Tyr<br>770 775 780 | 2408 |
| ATC TCT GCT GCT CCA GGC GCT GAA GCC AAG TAC CGC AGT GCA AGC AGC<br>Ile Ser Ala Ala Pro Gly Ala Glu Ala Lys Tyr Arg Ser Ala Ser Ser<br>785 790 795 800 | 2456 |
| GCC TCC AGC CTC TTC AGC CCG AGC AGC ACT CTT TTC TCT TCC TCT CGT<br>Ala Ser Ser Leu Phe Ser Pro Ser Ser Thr Leu Phe Ser Ser Ser Arg<br>805 810 815 | 2504 |
| TTG CGA TAT GGA ATG TCT GAT GTC ATG CCT TCT GGC AGG AGC AGG CTT<br>Leu Arg Tyr Gly Met Ser Asp Val Met Pro Ser Gly Arg Ser Arg Leu<br>820 825 830 | 2552 |
| TTG GAA GAT TTT CGA AAC AAC CGG TAC CCC AAT TTA CAA CTG CGG GAG<br>Leu Glu Asp Phe Arg Asn Asn Arg Tyr Pro Asn Leu Gln Leu Arg Glu<br>835 840 845 | 2600 |
| ATT GCT GGA CAT ATA ATG GAA TTT TCC CAA GAC CAG CAT GGG TCC AGA<br>Ile Ala Gly His Ile Met Glu Phe Ser Gln Asp Gln His Gly Ser Arg<br>850 855 860 | 2648 |
| TTC ATT CAG CTG AAA CTG GAG CGT GCC ACA CCA GCT GAG CGC CAG CTT<br>Phe Ile Gln Leu Lys Leu Glu Arg Ala Thr Pro Ala Glu Arg Gln Leu<br>865 870 875 880 | 2696 |
| GTC TTC AAT GAA ATC CTC CAG GCT GCC TAC CAA CTC ATG GTG GAT GTG<br>Val Phe Asn Glu Ile Leu Gln Ala Ala Tyr Gln Leu Met Val Asp Val<br>885 890 895 | 2744 |

```
TTT GGT AAT TAC GTC ATT CAG AAG TTC TTT GAA TTT GGC AGT CTT GAA    2792
Phe Gly Asn Tyr Val Ile Gln Lys Phe Phe Glu Phe Gly Ser Leu Glu
            900                 905                 910

CAG AAG CTG GCT TTG GCA GAA CGG ATT CGA GGC CAC GTC CTG TCA TTG    2840
Gln Lys Leu Ala Leu Ala Glu Arg Ile Arg Gly His Val Leu Ser Leu
            915                 920                 925

GCA CTA CAG ATG TAT GGC TGC CGT GTT ATC CAG AAA GCT CTT GAG TTT    2888
Ala Leu Gln Met Tyr Gly Cys Arg Val Ile Gln Lys Ala Leu Glu Phe
            930                 935                 940

ATT CCT TCA GAC CAG CAG AAT GAG ATG GTT CGG GAA CTA GAT GGC CAT    2936
Ile Pro Ser Asp Gln Gln Asn Glu Met Val Arg Glu Leu Asp Gly His
945                 950                 955                 960

GTC TTG AAG TGT GTG AAA GAT CAG AAT GGC AAT CAC GTG GTT CAG AAA    2984
Val Leu Lys Cys Val Lys Asp Gln Asn Gly Asn His Val Val Gln Lys
                965                 970                 975

TGC ATT GAA TGT GTA CAG CCC CAG TCT TTG CAA TTT ATC ATC GAT GCG    3032
Cys Ile Glu Cys Val Gln Pro Gln Ser Leu Gln Phe Ile Ile Asp Ala
            980                 985                 990

TTT AAG GGA CAG GTA TTT GCC TTA TCC ACA CAT CCT TAT GGC TGC CGA    3080
Phe Lys Gly Gln Val Phe Ala Leu Ser Thr His Pro Tyr Gly Cys Arg
            995                 1000                1005

GTG ATT CAG AGA ATC CTG GAG CAC TGT CTC CCT GAC CAG ACA CTC CCT    3128
Val Ile Gln Arg Ile Leu Glu His Cys Leu Pro Asp Gln Thr Leu Pro
            1010                1015                1020

ATT TTA GAG GAG CTT CAC CAG CAC ACA GAG CAG CTT GTA CAG GAT CAA    3176
Ile Leu Glu Glu Leu His Gln His Thr Glu Gln Leu Val Gln Asp Gln
1025                1030                1035                1040

TAT GGA AAT TAT GTA ATC CAA CAT GTA CTG GAG CAC GGT CGT CCT GAG    3224
Tyr Gly Asn Tyr Val Ile Gln His Val Leu Glu His Gly Arg Pro Glu
            1045                1050                1055

GAT AAA AGC AAA ATT GTA GCA GAA ATC CGA GGC AAT GTA CTT GTA TTG    3272
Asp Lys Ser Lys Ile Val Ala Glu Ile Arg Gly Asn Val Leu Val Leu
            1060                1065                1070

AGT CAG CAC AAA TTT GCA AGC AAT GTT GTG GAG AAG TGT GTT ACT CAC    3320
Ser Gln His Lys Phe Ala Ser Asn Val Val Glu Lys Cys Val Thr His
            1075                1080                1085

GCC TCA CGT ACG GAG CGC GCT GTG CTC ATC GAT GAG GTG TGC ACC ATG    3368
Ala Ser Arg Thr Glu Arg Ala Val Leu Ile Asp Glu Val Cys Thr Met
            1090                1095                1100

AAC GAC GGT CCC CAC AGT GCC TTA TAC ACC ATG ATG AAG GAC CAG TAT    3416
Asn Asp Gly Pro His Ser Ala Leu Tyr Thr Met Met Lys Asp Gln Tyr
1105                1110                1115                1120

GCC AAC TAC GTG GTC CAG AAG ATG ATT GAC GTG GCG GAG CCA GGC CAG    3464
Ala Asn Tyr Val Val Gln Lys Met Ile Asp Val Ala Glu Pro Gly Gln
            1125                1130                1135

CGG AAG ATC GTC ATG CAT AAG ATC CGG CCC CAC ATC GCA ACT CTT CGT    3512
Arg Lys Ile Val Met His Lys Ile Arg Pro His Ile Ala Thr Leu Arg
            1140                1145                1150

AAG TAC ACC TAT GGC AAG CAC ATT CTG GCC AAG CTG GAG AAG TAC TAC    3560
Lys Tyr Thr Tyr Gly Lys His Ile Leu Ala Lys Leu Glu Lys Tyr Tyr
            1155                1160                1165

ATG AAG AAC GGT GTT GAC TTA GGG CCC ATC TGT GGC CCC CCT AAT GGT    3608
Met Lys Asn Gly Val Asp Leu Gly Pro Ile Cys Gly Pro Pro Asn Gly
            1170                1175                1180

ATC ATC TGAGGCAGTG TCACCCGCTG TTCCCTCATT CCCGCTGACC TCACTGGCCC     3664
Ile Ile
1185

ACTGGCAAAT CCAACCAGCA ACCAGAAATG TTCTAGTGTA GAGTCTGAGA CGGGCAAGTG   3724

GTTGCTCCAG GATTACTCCC TCCTCCAAAA AAGGAATCAA ATCCACGAGT GGAAAAGCCT   3784
```

```
TTGTAAATTT AATTTTATTA CACATAACAT GTACTATTTT TTTTAATTGA CTAATTGCCC    3844

TGCTGTTTTA CTGGTGTATA GGATACTTGT ACATAGGTAA CCAATGTACA TGGGAGGCCA    3904

CATATTTTGT TCACTGTTGT ATCTATATTT CACATGTGGA AACTTTCAGG GTGGTTGGTT    3964

TAACAAAAAA AAAAAGCTTT AAAAAAAAAA GAAAAAAAGG AAAAGGTTTT TAGCTCATTT    4024

GCCTGGCCGG CAAGTTTTGC AAATAGCTCT TCCCCACCTC CTCATTTTAG TAAAAAACAA    4084

ACAAAAACAA AAAACCTGA GAAGTTTGAA TTGTAGTTAA ATGACCCCAA ACTGGCATTT     4144

AACACTGTTT ATAAAAAATA TATATATATA TATATATATA TAATGAAAAA GGTTTCAGAG    4204

TTGCTAAAGC TTCAGTTTGT GACATTAAGT TTATGAAATT CTAAAAAATG CCTTTTTTGG    4264

AGACTATATT ATGCTGAAGA AGGCTGTTCG TGAGGAGGAG ATGCGAGCAC CCAGAACGTC    4324

TTTTGAGGCT GGGCGGGTGT GATTGTTTAC TGCCTACTGG ATTTTTTTCT ATTAACATTG    4384

AAAGGTAAAA TCTGATTATT TAGCATGAGA AAAAAAATCC AACTCTGCTT TTGGTCTTGC    4444

TTCTATAAAT ATATAGTGTA TACTTGGTGT AGACTTTGCA TATATACAAA TTTGTAGTAT    4504

TTTCTTGTTT TGATGTCTAA TCTGTATCTA TAATGTACCC TAGTAGTCGA ACATACTTTT    4564

GATTGTACAA TTGTACATTT GTATACCTGT AATGTAAATG TGGAGAAGTT TGAATCAACA    4624

TAAACACGTT TTTTGGTAAG AAAAGAGAAT TAGCCAGCCC TGTGCATTCA GTGTATATTC    4684

TCACCTTTTA TGGTCGTAGC ATATAGTGTT GTATATTGTA AATTGTAATT TCAACCAGAA    4744

GTAAATTTTT TTGTTTTGAA GGAATAAATG TTCTTTATAC AGCCTAGTTA ATGTTTAAAA    4804

AGAAAAAAAT AGCTTGGTTT TATTTGTCAT CTAGTCTCAA GTATAGCGAG ATTCTTTCTA    4864

AATGTTATTC AAGATTGAGT TCTCACTAGT GTTTTTTTAA TCCTAAAAAA GTAATGTTTT    4924

GATTTTGTGA CAGTCAAAAG GACGTGCAAA AGTCTAGCCT TGCCCGAGCT TTCCTTACAA    4984

TCAGAGCCCC TCTCACCTTG TAAAGTGTGA ATCGCCCTTC CCTTTTGTAC AGAAGATGAA    5044

CTGTATTTTG CATTTTGTCT ACTTGTAAGT GAATGTAACA TACTGTCAAT TTTCCTTGTT    5104

TGAATATAGA ATTGTAACAC TACACGGTGT ACATTTCCAG AGCCTTGTGT ATATTTCCAA    5164

TGAACTTTTT TGCAAGCACA CTTGTAACCA TATGTGTATA ATTAACAAAC CTGTGTATGC    5224

TTATGCCTGG GCAACTATTT TTTGTAACTC TTGTGTAGAT TGTCTCTAAA CAATGTGTGA    5284

TCTTTATTTT GAAAAATACA GAACTTTGGA ATCTG                               5319

(2) INFORMATION FOR SEQ ID NO:8:

(i) SEQUENCE CHARACTERISTICS:
        (A) LENGTH: 1186 amino acids
        (B) TYPE: amino acid
        (D) TOPOLOGY: linear (ii) MOLECULE TYPE: protein (xi) SEQUENCE DESCRIPTION: SEQ ID NO:8:

Met Ser Val Ala Cys Val Leu Lys Arg Lys Ala Val Leu Trp Gln Asp
1               5                  10                  15

Ser Phe Ser Pro His Leu Lys His His Pro Gln Glu Pro Ala Asn Pro
            20                  25                  30

Asn Met Pro Val Val Leu Thr Ser Gly Thr Gly Ser Gln Ala Gln Pro
        35                  40                  45

Gln Pro Ala Ala Asn Gln Ala Leu Ala Ala Gly Thr His Ser Ser Pro
    50                  55                  60

Val Pro Gly Ser Ile Gly Val Ala Gly Arg Ser Gln Asp Asp Ala Met
65                  70                  75                  80
```

```
Val Asp Tyr Phe Phe Gln Arg Gln His Gly Glu Gln Leu Gly Gly Gly
            85                  90                  95

Gly Ser Gly Gly Gly Gly Tyr Asn Asn Ser Lys His Arg Trp Pro Thr
            100                 105                 110

Gly Asp Asn Ile His Ala Glu His Gln Val Arg Ser Met Asp Glu Leu
            115                 120                 125

Asn His Asp Phe Gln Ala Leu Ala Leu Glu Gly Arg Ala Met Gly Glu
130                 135                 140

Gln Leu Leu Pro Gly Lys Lys Phe Trp Glu Thr Asp Glu Ser Ser Lys
145                 150                 155                 160

Asp Gly Pro Lys Gly Ile Phe Leu Gly Asp Gln Trp Arg Asp Ser Ala
                    165                 170                 175

Trp Gly Thr Ser Asp His Ser Val Ser Gln Pro Ile Met Val Gln Arg
            180                 185                 190

Arg Pro Gly Gln Ser Phe His Val Asn Ser Glu Val Asn Ser Val Leu
            195                 200                 205

Ser Pro Arg Ser Glu Ser Gly Gly Leu Gly Val Ser Met Val Glu Tyr
            210                 215                 220

Val Leu Ser Ser Ser Pro Gly Asp Ser Cys Leu Arg Lys Gly Gly Phe
225                 230                 235                 240

Gly Pro Arg Asp Ala Asp Ser Asp Glu Asn Asp Lys Gly Glu Lys Lys
                    245                 250                 255

Asn Lys Gly Thr Phe Asp Gly Asp Lys Leu Gly Asp Leu Lys Glu Glu
            260                 265                 270

Gly Asp Val Met Asp Lys Thr Asn Gly Leu Pro Val Gln Asn Gly Ile
            275                 280                 285

Asp Ala Asp Val Lys Asp Phe Ser Arg Thr Pro Gly Asn Cys Gln Asn
            290                 295                 300

Ser Ala Asn Glu Val Asp Leu Leu Gly Pro Asn Gln Asn Gly Ser Glu
305                 310                 315                 320

Gly Leu Ala Gln Leu Thr Ser Thr Asn Gly Ala Lys Pro Val Glu Asp
                    325                 330                 335

Phe Ser Asn Met Glu Ser Gln Ser Val Pro Leu Asp Pro Met Glu His
            340                 345                 350

Val Gly Met Glu Pro Leu Gln Phe Asp Tyr Ser Gly Thr Gln Val Pro
            355                 360                 365

Val Asp Ser Ala Ala Thr Val Gly Leu Phe Asp Tyr Asn Ser Gln
370                 375                 380

Gln Gln Leu Phe Gln Arg Pro Asn Ala Leu Ala Val Gln Gln Leu Thr
385                 390                 395                 400

Ala Ala Gln Gln Gln Gln Tyr Ala Leu Ala Ala His Gln Pro His
                    405                 410                 415

Ile Gly Leu Ala Pro Ala Ala Phe Val Pro Asn Pro Tyr Ile Ile Ser
            420                 425                 430

Ala Ala Pro Pro Gly Thr Asp Pro Tyr Thr Ala Gly Leu Ala Ala Ala
            435                 440                 445

Ala Thr Leu Gly Pro Ala Val Val Pro His Gln Tyr Tyr Gly Val Thr
            450                 455                 460

Pro Trp Gly Val Tyr Pro Ala Ser Leu Phe Gln Gln Ala Ala Ala
465                 470                 475                 480

Ala Ala Ala Ala Thr Asn Ser Ala Asn Gln Gln Thr Thr Pro Gln Ala
                    485                 490                 495

Gln Gln Gly Gln Gln Gln Val Leu Arg Gly Gly Ala Ser Gln Arg Pro
            500                 505                 510
```

```
Leu Thr Pro Asn Gln Asn Gln Gln Gly Gln Gln Thr Asp Pro Leu Val
        515                 520                 525

Ala Ala Ala Ala Val Asn Ser Ala Leu Ala Phe Gly Gln Gly Leu Ala
    530                 535                 540

Ala Gly Met Pro Gly Tyr Pro Val Leu Ala Pro Ala Ala Tyr Tyr Asp
545                 550                 555                 560

Gln Thr Gly Ala Leu Val Val Asn Ala Gly Ala Arg Asn Gly Leu Gly
                565                 570                 575

Ala Pro Val Arg Leu Val Ala Pro Ala Pro Val Ile Ile Ser Ser Ser
            580                 585                 590

Ala Ala Gln Ala Ala Val Ala Ala Ala Ala Ser Ala Asn Gly Ala
        595                 600                 605

Ala Gly Gly Leu Ala Gly Thr Thr Asn Gly Pro Phe Arg Pro Leu Gly
    610                 615                 620

Thr Gln Gln Pro Gln Pro Gln Pro Gln Gln Pro Asn Asn Asn Leu
625                 630                 635                 640

Ala Ser Ser Ser Phe Tyr Gly Asn Asn Ser Leu Asn Ser Asn Ser Gln
                645                 650                 655

Ser Ser Ser Leu Phe Ser Gln Gly Ser Ala Gln Pro Ala Asn Thr Ser
            660                 665                 670

Leu Gly Phe Gly Ser Ser Ser Leu Gly Ala Thr Leu Gly Ser Ala
        675                 680                 685

Leu Gly Gly Phe Gly Thr Ala Val Ala Asn Ser Asn Thr Gly Ser Gly
    690                 695                 700

Ser Arg Arg Asp Ser Leu Thr Gly Ser Ser Asp Leu Tyr Lys Arg Thr
705                 710                 715                 720

Ser Ser Ser Leu Thr Pro Ile Gly His Ser Phe Tyr Asn Gly Leu Ser
                725                 730                 735

Phe Ser Ser Pro Gly Pro Val Gly Met Pro Leu Pro Ser Gln Gly
            740                 745                 750

Pro Gly His Ser Gln Thr Pro Pro Ser Leu Ser Ser His Gly Ser
        755                 760                 765

Ser Ser Ser Leu Asn Leu Gly Gly Leu Thr Asn Gly Ser Gly Arg Tyr
    770                 775                 780

Ile Ser Ala Ala Pro Gly Ala Glu Ala Lys Tyr Arg Ser Ala Ser Ser
785                 790                 795                 800

Ala Ser Ser Leu Phe Ser Pro Ser Ser Thr Leu Phe Ser Ser Ser Arg
                805                 810                 815

Leu Arg Tyr Gly Met Ser Asp Val Met Pro Ser Gly Arg Ser Arg Leu
            820                 825                 830

Leu Glu Asp Phe Arg Asn Asn Arg Tyr Pro Asn Leu Gln Leu Arg Glu
        835                 840                 845

Ile Ala Gly His Ile Met Glu Phe Ser Gln Asp Gln His Gly Ser Arg
    850                 855                 860

Phe Ile Gln Leu Lys Leu Glu Arg Ala Thr Pro Ala Glu Arg Gln Leu
865                 870                 875                 880

Val Phe Asn Glu Ile Leu Gln Ala Ala Tyr Gln Leu Met Val Asp Val
                885                 890                 895

Phe Gly Asn Tyr Val Ile Gln Lys Phe Phe Glu Phe Gly Ser Leu Glu
            900                 905                 910

Gln Lys Leu Ala Leu Ala Glu Arg Ile Arg Gly His Val Leu Ser Leu
        915                 920                 925

Ala Leu Gln Met Tyr Gly Cys Arg Val Ile Gln Lys Ala Leu Glu Phe
```

```
         930             935             940
Ile Pro Ser Asp Gln Gln Asn Glu Met Val Arg Glu Leu Asp Gly His
945                 950             955                 960

Val Leu Lys Cys Val Lys Asp Gln Asn Gly Asn His Val Val Gln Lys
                965             970             975

Cys Ile Glu Cys Val Gln Pro Gln Ser Leu Gln Phe Ile Ile Asp Ala
            980             985             990

Phe Lys Gly Gln Val Phe Ala Leu Ser Thr His Pro Tyr Gly Cys Arg
        995             1000            1005

Val Ile Gln Arg Ile Leu Glu His Cys Leu Pro Asp Gln Thr Leu Pro
    1010            1015            1020

Ile Leu Glu Glu Leu His Gln His Thr Glu Gln Leu Val Gln Asp Gln
1025            1030            1035            1040

Tyr Gly Asn Tyr Val Ile Gln His Val Leu Glu His Gly Arg Pro Glu
                1045            1050            1055

Asp Lys Ser Lys Ile Val Ala Glu Ile Arg Gly Asn Val Leu Val Leu
            1060            1065            1070

Ser Gln His Lys Phe Ala Ser Asn Val Val Glu Lys Cys Val Thr His
        1075            1080            1085

Ala Ser Arg Thr Glu Arg Ala Val Leu Ile Asp Glu Val Cys Thr Met
    1090            1095            1100

Asn Asp Gly Pro His Ser Ala Leu Tyr Thr Met Met Lys Asp Gln Tyr
1105            1110            1115            1120

Ala Asn Tyr Val Val Gln Lys Met Ile Asp Val Ala Glu Pro Gly Gln
                1125            1130            1135

Arg Lys Ile Val Met His Lys Ile Arg Pro His Ile Ala Thr Leu Arg
            1140            1145            1150

Lys Tyr Thr Tyr Gly Lys His Ile Leu Ala Lys Leu Glu Lys Tyr Tyr
        1155            1160            1165

Met Lys Asn Gly Val Asp Leu Gly Pro Ile Cys Gly Pro Pro Asn Gly
    1170            1175            1180

Ile Ile
1185

(2) INFORMATION FOR SEQ ID NO:9:

(i) SEQUENCE CHARACTERISTICS:
        (A) LENGTH: 2112 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 419..1942

(xi) SEQUENCE DESCRIPTION: SEQ ID NO:9:

GGAAGTTAAA GGGAAAAAGC AATTCACAGG AAAGAGTACA AAGACAGCAC AAGAAAAAAA      60

CAGATTTCAT AAAAATAGTG ATTCTGGTTC TTCAAAGACA TTTCCAACAA GGAAAGTTGC     120

TAAAGAAGGT GGACCTAAAG TCACATCTAG GAACTTTGAG AAAAGTATCA CAAAACTTGG     180

GAAAAAGGGT GTAAAGCAGT TCAAGAATAA GCAGCAAGGG GACAAATCAC CAAAGAACAA     240

ATTCCAGCCG GCAAATAAAT TCAACAAGAA GAGAAAATTC CAGCCAGATG GTAGAAGCGA     300

TGAATCAGCA GCCAAGAAGC CCAAATGGGA TGACTTCAAA AAGAAGAAGA AAGAACTGAA     360

GCAAAGCAGA CAACTCAGTG ATAAAACCAA CTATGACATT GTTGTTCGGG CAAAGCAG       418
```

```
ATG TGG GAG ATT TTA AGA AGA AAA GAC TGT GAC AAA GAA AAA AGA GTA      466
Met Trp Glu Ile Leu Arg Arg Lys Asp Cys Asp Lys Glu Lys Arg Val
 1               5                  10                  15

AAG TTA ATG AGT GAT TTG CAG AAG TTG ATT CAA GGG AAA ATT AAA ACT      514
Lys Leu Met Ser Asp Leu Gln Lys Leu Ile Gln Gly Lys Ile Lys Thr
            20                  25                  30

ATT GCA TTT GCA CAC GAT TCA ACT CGT GTG ATC CAG TGT TAC ATT CAG      562
Ile Ala Phe Ala His Asp Ser Thr Arg Val Ile Gln Cys Tyr Ile Gln
                35                  40                  45

TAT GGT AAT GAA GAA CAG AGA AAA CAG GCT TTT GAA GAA TTG CGA GAT      610
Tyr Gly Asn Glu Glu Gln Arg Lys Gln Ala Phe Glu Glu Leu Arg Asp
        50                  55                  60

GAT TTG GTT GAG TTA AGT AAA GCC AAA TAT TCG AGA AAT ATT GTT AAG      658
Asp Leu Val Glu Leu Ser Lys Ala Lys Tyr Ser Arg Asn Ile Val Lys
 65                 70                  75                  80

AAA TTT CTC ATG TAT GGA AGT AAA CCA CAG ATT GCA GAG ATA ATC AGA      706
Lys Phe Leu Met Tyr Gly Ser Lys Pro Gln Ile Ala Glu Ile Ile Arg
                85                  90                  95

AGT TTT AAA GGC CAC GTG AGG AAG ATG CTG CGG CAT GCG GAA GCA TCA      754
Ser Phe Lys Gly His Val Arg Lys Met Leu Arg His Ala Glu Ala Ser
            100                 105                 110

GCC ATC GTG GAG TAC GCA TAC AAT GAC AAA GCC ATT TTG GAG CAG AGG      802
Ala Ile Val Glu Tyr Ala Tyr Asn Asp Lys Ala Ile Leu Glu Gln Arg
                115                 120                 125

AAC ATG CTG ACG GAA GAG CTC TAT GGG AAC ACA TTT CAG CTT TAC AAG      850
Asn Met Leu Thr Glu Glu Leu Tyr Gly Asn Thr Phe Gln Leu Tyr Lys
130                 135                 140

TCA GCA GAT CAC CGA ACT CTG GAC AAA GTG TTA GAG GTA CAG CCA GAA      898
Ser Ala Asp His Arg Thr Leu Asp Lys Val Leu Glu Val Gln Pro Glu
145                 150                 155                 160

AAA TTA GAA CTT ATT ATG GAT GAA ATG AAA CAG ATT CTA ACT CCA ATG      946
Lys Leu Glu Leu Ile Met Asp Glu Met Lys Gln Ile Leu Thr Pro Met
                165                 170                 175

GCC CAA AAG GAA GCT GTG ATT AAG CAC TCA TTG GTG CAT AAA GTA TTC      994
Ala Gln Lys Glu Ala Val Ile Lys His Ser Leu Val His Lys Val Phe
            180                 185                 190

TTG GAC TTT TTT ACC TAT GCA CCC CCC AAA CTC AGA TCA GAA ATG ATT     1042
Leu Asp Phe Phe Thr Tyr Ala Pro Pro Lys Leu Arg Ser Glu Met Ile
                195                 200                 205

GAA GCC ATC CGC GAA GCG GTG GTC TAC CTG GCA CAC ACA CAC GAT GGC     1090
Glu Ala Ile Arg Glu Ala Val Val Tyr Leu Ala His Thr His Asp Gly
210                 215                 220

GCC AGA GTG GCC ATG CAC TGC CTG TGG CAT GGC ACG CCC AAG GAC AGG     1138
Ala Arg Val Ala Met His Cys Leu Trp His Gly Thr Pro Lys Asp Arg
225                 230                 235                 240

AAA GTG ATT GTG AAA ACA ATG AAG ACT TAT GTT GAA AAG GTG GCT AAT     1186
Lys Val Ile Val Lys Thr Met Lys Thr Tyr Val Glu Lys Val Ala Asn
                245                 250                 255

GGC CAA TAC TCC CAT TTG GTT TTA CTG GCG GCA TTT GAT TGT ATT GAT     1234
Gly Gln Tyr Ser His Leu Val Leu Leu Ala Ala Phe Asp Cys Ile Asp
            260                 265                 270

GAT ACT AAG CTT GTG AAG CAG ATA ATC ATA TCA GAA ATT ATC AGT TCA     1282
Asp Thr Lys Leu Val Lys Gln Ile Ile Ile Ser Glu Ile Ile Ser Ser
            275                 280                 285

TTG CCT AGC ATA GTA AAT GAC AAA TAT GGA AGG AAG GTC CTA TTG TAC     1330
Leu Pro Ser Ile Val Asn Asp Lys Tyr Gly Arg Lys Val Leu Leu Tyr
        290                 295                 300

TTA CTA AGC CCC AGA GAT CCT GCA CAT ACA GTA CGA GAA ATC ATT GAA     1378
Leu Leu Ser Pro Arg Asp Pro Ala His Thr Val Arg Glu Ile Ile Glu
305                 310                 315                 320
```

```
GTT CTG CAA AAA GGA GAT GGA AAT GCA CAC AGT AAG AAA GAT ACA GAG      1426
Val Leu Gln Lys Gly Asp Gly Asn Ala His Ser Lys Lys Asp Thr Glu
                325                 330                 335

GTC CGC AGA CGG GAG CTC CTA GAA TCC ATT TCT CCA GCT TTG TTA AGC      1474
Val Arg Arg Arg Glu Leu Leu Glu Ser Ile Ser Pro Ala Leu Leu Ser
            340                 345                 350

TAC CTG CAA GAA CAC GCC CAA GAA GTG GTG CTA GAT AAG TCT GCG TGT      1522
Tyr Leu Gln Glu His Ala Gln Glu Val Val Leu Asp Lys Ser Ala Cys
        355                 360                 365

GTG TTG GTG TCT GAC ATT CTG GGA TCT GCC ACT GGA GAC GTT CAG CCT      1570
Val Leu Val Ser Asp Ile Leu Gly Ser Ala Thr Gly Asp Val Gln Pro
    370                 375                 380

ACC ATG AAT GCC ATC GCC AGC TTG GCA GCA ACA GGA CTG CAT CCT GGT      1618
Thr Met Asn Ala Ile Ala Ser Leu Ala Ala Thr Gly Leu His Pro Gly
385                 390                 395                 400

GGC AAG GAC GGA GAG CTT CAC ATT GCA GAA CAT CCT GCA GGA CAT CTA      1666
Gly Lys Asp Gly Glu Leu His Ile Ala Glu His Pro Ala Gly His Leu
                405                 410                 415

GTT CTG AAG TGG TTA ATA GAG CAA GAT AAA AAG ATG AAA GAA AAT GGG      1714
Val Leu Lys Trp Leu Ile Glu Gln Asp Lys Lys Met Lys Glu Asn Gly
            420                 425                 430

AGA GAA GGT TGT TTT GCA AAA ACA CTT GTA GAG CAT GTT GGT ATG AAG      1762
Arg Glu Gly Cys Phe Ala Lys Thr Leu Val Glu His Val Gly Met Lys
        435                 440                 445

AAC CTG AAG TCC TGG GCT AGT GTA AAT CGA GGT GCC ATT ATT CTT TCT      1810
Asn Leu Lys Ser Trp Ala Ser Val Asn Arg Gly Ala Ile Ile Leu Ser
    450                 455                 460

AGC CTC CTC CAG AGT TGT GAC CTG GAA GTT GCA AAC AAA GTC AAA GCT      1858
Ser Leu Leu Gln Ser Cys Asp Leu Glu Val Ala Asn Lys Val Lys Ala
465                 470                 475                 480

GCA CTG AAA AGC TTG ATT CCT ACA CTG GAA AAA ACC AAA AGC ACC AGC      1906
Ala Leu Lys Ser Leu Ile Pro Thr Leu Glu Lys Thr Lys Ser Thr Ser
                485                 490                 495

AAA GGA ATA GAA ATT CTA CTT GAA AAA CTG AGC ACA TAGGTGGAAA           1952
Lys Gly Ile Glu Ile Leu Leu Glu Lys Leu Ser Thr
                500                 505

GAGTTAAGAG CAAGATGGAA TGATTTTTTC TGTTCTCTGT TCTGTTTCCC AATGCAGAAA    2012

AGAAGGGGTA GGGTCCACCA TACTGGTAAT TGGGGTACTC TGTATATGTG TTTCTTCTTT    2072

GTATACGAAT CTATTTATAT AAATTGTTTT TTTAAATGGT                          2112

(2) INFORMATION FOR SEQ ID NO:10:

(i) SEQUENCE CHARACTERISTICS:
        (A) LENGTH: 508 amino acids
        (B) TYPE: amino acid
        (D) TOPOLOGY: linear (ii) MOLECULE TYPE: protein (xi) SEQUENCE DESCRIPTION: SEQ ID NO:10:

Met Trp Glu Ile Leu Arg Arg Lys Asp Cys Asp Lys Glu Lys Arg Val
1               5                   10                  15

Lys Leu Met Ser Asp Leu Gln Lys Leu Ile Gln Gly Lys Ile Lys Thr
            20                  25                  30

Ile Ala Phe Ala His Asp Ser Thr Arg Val Ile Gln Cys Tyr Ile Gln
        35                  40                  45

Tyr Gly Asn Glu Glu Gln Arg Lys Gln Ala Phe Glu Glu Leu Arg Asp
    50                  55                  60

Asp Leu Val Glu Leu Ser Lys Ala Lys Tyr Ser Arg Asn Ile Val Lys
```

-continued

```
                65                  70                  75                  80
Lys Phe Leu Met Tyr Gly Ser Lys Pro Gln Ile Ala Glu Ile Ile Arg
                            85                  90                  95
Ser Phe Lys Gly His Val Arg Lys Met Leu Arg His Ala Glu Ala Ser
                100                 105                 110
Ala Ile Val Glu Tyr Ala Tyr Asn Asp Lys Ala Ile Leu Glu Gln Arg
                115                 120                 125
Asn Met Leu Thr Glu Glu Leu Tyr Gly Asn Thr Phe Gln Leu Tyr Lys
            130                 135                 140
Ser Ala Asp His Arg Thr Leu Asp Lys Val Leu Glu Val Gln Pro Glu
145                 150                 155                 160
Lys Leu Glu Leu Ile Met Asp Glu Met Lys Gln Ile Leu Thr Pro Met
                165                 170                 175
Ala Gln Lys Glu Ala Val Ile Lys His Ser Leu Val His Lys Val Phe
                180                 185                 190
Leu Asp Phe Phe Thr Tyr Ala Pro Pro Lys Leu Arg Ser Glu Met Ile
            195                 200                 205
Glu Ala Ile Arg Glu Ala Val Val Tyr Leu Ala His Thr His Asp Gly
210                 215                 220
Ala Arg Val Ala Met His Cys Leu Trp His Gly Thr Pro Lys Asp Arg
225                 230                 235                 240
Lys Val Ile Val Lys Thr Met Lys Thr Tyr Val Glu Lys Val Ala Asn
                245                 250                 255
Gly Gln Tyr Ser His Leu Val Leu Ala Ala Phe Asp Cys Ile Asp
                260                 265                 270
Asp Thr Lys Leu Val Lys Gln Ile Ile Ser Glu Ile Ile Ser Ser
            275                 280                 285
Leu Pro Ser Ile Val Asn Asp Lys Tyr Gly Arg Lys Val Leu Leu Tyr
            290                 295                 300
Leu Leu Ser Pro Arg Asp Pro Ala His Thr Val Arg Glu Ile Ile Glu
305                 310                 315                 320
Val Leu Gln Lys Gly Asp Gly Asn Ala His Ser Lys Lys Asp Thr Glu
                325                 330                 335
Val Arg Arg Arg Glu Leu Leu Glu Ser Ile Ser Pro Ala Leu Leu Ser
                340                 345                 350
Tyr Leu Gln Glu His Ala Gln Glu Val Val Leu Asp Lys Ser Ala Cys
            355                 360                 365
Val Leu Val Ser Asp Ile Leu Gly Ser Ala Thr Gly Asp Val Gln Pro
            370                 375                 380
Thr Met Asn Ala Ile Ala Ser Leu Ala Ala Thr Gly Leu His Pro Gly
385                 390                 395                 400
Gly Lys Asp Gly Glu Leu His Ile Ala Glu His Pro Ala Gly His Leu
                405                 410                 415
Val Leu Lys Trp Leu Ile Glu Gln Asp Lys Met Lys Glu Asn Gly
                420                 425                 430
Arg Glu Gly Cys Phe Ala Lys Thr Leu Val Glu His Val Gly Met Lys
            435                 440                 445
Asn Leu Lys Ser Trp Ala Ser Val Asn Arg Gly Ala Ile Ile Leu Ser
450                 455                 460
Ser Leu Leu Gln Ser Cys Asp Leu Glu Val Ala Asn Lys Val Lys Ala
465                 470                 475                 480
Ala Leu Lys Ser Leu Ile Pro Thr Leu Glu Lys Thr Lys Ser Thr Ser
                485                 490                 495
```

Lys Gly Ile Glu Ile Leu Leu Glu Lys Leu Ser Thr
          500                     505

(2) INFORMATION FOR SEQ ID NO:11:

(i) SEQUENCE CHARACTERISTICS:
        (A) LENGTH: 2457 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 645..1655

(xi) SEQUENCE DESCRIPTION: SEQ ID NO:11:

| | |
|---|---|
| GGATCCCTCT GTGAGGCCGA TTATGCAGGC CTAGACCCGC ACGTGACCAC TTCGAGAGCA | 60 |
| AGTTGCCTGC GAGTTTCTCT GCCCGAGGAA AAAGAAATGG AGGCAATTTA CTTAATATGG | 120 |
| TATGAGAGGA TCTTTTGACG GCAAATAGAT GCGCCATCTC CGAGAAAAAA TCTAGACAAT | 180 |
| AACAGCGACA ATTAACCTAA AGAGGATAGA AGATCGAGCA AAAAAATTTT TTAATATGGG | 240 |
| GTCAGTGGCG ATATTATACT ATAGGAGTTA AAGAGTAAGT TGAGTGTAAG GTGGTAGAAT | 300 |
| TATGATTGAA CTCCGAAACT AAGCGCCGAT TATGGGTGGC AAAGCGGACA GCTTTTGATA | 360 |
| TATAATCGAT CGCTCTCGTA GTTGATATCC TCTCTCTTGC TTATCTTTTC CTGTATATAG | 420 |
| TATATGTGTA CATACAGATA CGAATATACC TCAGTTAGTT TGTTTTAACA TTAAATATTC | 480 |
| AACAGTTGCC AGTAGCAAAA AGAATATATC CATTCATTTC GAGCTTTTTC GTCTCATTAC | 540 |
| TGATATCCAA CTAACAGTCT CCTCATAGAC GGTACCTTAC TTTCCTTTAA TATTAAAATA | 600 |
| CTAGTATAGT CGCACATACT TAACTCGTCT CTCTCTAACA CATA ATG AAA ATT TCC | 656 |
|                                                                             Met Lys Ile Ser<br>                                                                             1 | |
| GCA GCT TTA ATA TTG TCT TCC CTT TCT TCT GTC GCA TTT TCT GCC CCT<br>Ala Ala Leu Ile Leu Ser Ser Leu Ser Ser Val Ala Phe Ser Ala Pro<br> 5                      10                   15                 20 | 704 |
| GCA CCT GCT CCA GCG GAC AGT CAT CAT GAA GAT CAT CAC AAA GAT GAA<br>Ala Pro Ala Pro Ala Asp Ser His His Glu Asp His His Lys Asp Glu<br>                   25                   30                   35 | 752 |
| AAA CCA GCG GTT GTC ACT GTC ACT CAA TAC ATA GAT TCC AAT GCC GCT<br>Lys Pro Ala Val Val Thr Val Thr Gln Tyr Ile Asp Ser Asn Ala Ala<br>                 40                   45                   50 | 800 |
| ACT AGT ACT GTA GAA TCT GCT GCT ACT ACC ACT ACA TTG TCC TCA TCT<br>Thr Ser Thr Val Glu Ser Ala Ala Thr Thr Thr Thr Leu Ser Ser Ser<br>        55                   60                   65 | 848 |
| GAG AAG GAT ACC TCT GAA CAG AAG CGT GAT GGC GGA TTC CAA GAT GGT<br>Glu Lys Asp Thr Ser Glu Gln Lys Arg Asp Gly Gly Phe Gln Asp Gly<br> 70                     75                   80 | 896 |
| ACT GTC AAA TGT TCG GAC TTC CCT TCT GTA AAC GGT ATA GTT TCC TTG<br>Thr Val Lys Cys Ser Asp Phe Pro Ser Val Asn Gly Ile Val Ser Leu<br>85                   90                   95                 100 | 944 |
| GAC TGG CTA GGA TTT GGT GGA TGG GCC TCT GTC ATG GAC ATG GAT GCC<br>Asp Trp Leu Gly Phe Gly Gly Trp Ala Ser Val Met Asp Met Asp Ala<br>                 105                 110                 115 | 992 |
| AAC ACT TCG TCC GAA TGT AAG GAT GGC TAC TAC TGT TCT TAT GCA TGT<br>Asn Thr Ser Ser Glu Cys Lys Asp Gly Tyr Tyr Cys Ser Tyr Ala Cys<br>             120                 125                 130 | 1040 |
| GAA CCT GGA ATG TCA AAG ACT CAA TGG CCT TCT GAC CAA CCA AGC GAT<br>Glu Pro Gly Met Ser Lys Thr Gln Trp Pro Ser Asp Gln Pro Ser Asp<br>        135                 140                 145 | 1088 |

-continued

| | | |
|---|---|---|
| GGT AAA TCT GTT GGT GGT CTT TAT TGT AAA AAT GGT TAC TTG TAC CGT<br>Gly Lys Ser Val Gly Gly Leu Tyr Cys Lys Asn Gly Tyr Leu Tyr Arg<br>150              155                  160 | 1136 |
| ACC AAC ACT GAT ACC AGC GAT TTA TGT TCT ACG GAT GAA ACA TCT GCT<br>Thr Asn Thr Asp Thr Ser Asp Leu Cys Ser Thr Asp Glu Thr Ser Ala<br>165                  170                  175                  180 | 1184 |
| AAG GCC ATT AAC AAA AAG TCT GAC TCC ATT GCT CTA TGT AGG ACG GAT<br>Lys Ala Ile Asn Lys Lys Ser Asp Ser Ile Ala Leu Cys Arg Thr Asp<br>                 185                  190                  195 | 1232 |
| TAC CCA GGA TCT GAA AAC ATG GTG ATT CCC ACA GTG GTT GAT GGT GGA<br>Tyr Pro Gly Ser Glu Asn Met Val Ile Pro Thr Val Val Asp Gly Gly<br>                 200                  205                  210 | 1280 |
| GAT TCA CAA CCA ATT TCA GTC GTT GAT GAA GAC ACT TAT TAT CAA TGG<br>Asp Ser Gln Pro Ile Ser Val Val Asp Glu Asp Thr Tyr Tyr Gln Trp<br>                 215                  220                  225 | 1328 |
| CAG GGT AAA AAG ACT TCT GCT CAG TAC TAT ATT AAC AAC GCC GGT GTA<br>Gln Gly Lys Lys Thr Ser Ala Gln Tyr Tyr Ile Asn Asn Ala Gly Val<br>230                  235                  240 | 1376 |
| TCT GCA GAA GAT GGG TGC ATT TGG GGT ACT TCT GGT TCG GAT GTC GGC<br>Ser Ala Glu Asp Gly Cys Ile Trp Gly Thr Ser Gly Ser Asp Val Gly<br>245                  250                  255                  260 | 1424 |
| AAC TGG GCT CCA CTA GTG TTA GGT GCT GGT TCC ACT AAT GGA GAA ACA<br>Asn Trp Ala Pro Leu Val Leu Gly Ala Gly Ser Thr Asn Gly Glu Thr<br>                 265                  270                  275 | 1472 |
| TAC TTG TCG TTG ATT CCA AAC CCC AAC AGT AAC CAA GCT GCC AAC TTT<br>Tyr Leu Ser Leu Ile Pro Asn Pro Asn Ser Asn Gln Ala Ala Asn Phe<br>                 280                  285                  290 | 1520 |
| AAC GTT AAA ATA GTT GCA TCC GAT GGC GCT AAC GTT CAG GGC AGC TGT<br>Asn Val Lys Ile Val Ala Ser Asp Gly Ala Asn Val Gln Gly Ser Cys<br>                 295                  300                  305 | 1568 |
| GCG TAT GAA GAT GGC TCT TTC ACC GGA GAT GGT TCC GAT GGT TGC ACA<br>Ala Tyr Glu Asp Gly Ser Phe Thr Gly Asp Gly Ser Asp Gly Cys Thr<br>310                  315                  320 | 1616 |
| GTT TCT GTT TTA TCT GGA TCT GCT GAA TTT GTT TTC TAT TAAGTCACTC<br>Val Ser Val Leu Ser Gly Ser Ala Glu Phe Val Phe Tyr<br>325                  330                  335 | 1665 |
| TTCTTTTCGG TAAAAGAATG TCTTGTATTT TGATACCCTC AATTCCCCTT ATTATTCTTT | 1725 |
| TTCTTCCGCT CTCTATTTAT TATTATACAT TGGGATTCCG TTATATTTTT CTCCTTTCAG | 1785 |
| TTCATTTTAC TTCTTAAAAA GTTTCGTTGA TCGCTATTAT GCTATGGATT CAAAGATTTT | 1845 |
| CTTTTCTCTC TCTTCAAGGT GTACTCTGCA TTACGGTTTT CTTTAGTTCG TTTATTTTTT | 1905 |
| TTTTGTTAAC AAGGTGTTTG TATACATATA TATAAATATA TGGAAATATT ATAGTGTTTA | 1965 |
| TTTTGTTACT TCCTGCGAGT TGCAACAGAA CTAACAAGAT GCCATGCTGT TTTTTTTCAT | 2025 |
| TTTTTGGCTA TAAAAATAAC AGTATCCTAG TCCTTGTGTT CGGCTTTAAA ATGGAATTGC | 2085 |
| AAACCCCATA ATTCCTTCTT CACACCGAAC AAACCGCCTA GTAGTCGATT TTCAGAGACT | 2145 |
| CTAATGCTTT GAATATAATT TTTTTCTTCA AAAATTTCCT TAAGCGTGCT ATCGAATGAG | 2205 |
| TAGACATCAA TCAAGAGTTT CATGGTCTCC CCGTATTTGC CGCTGCTTCT AATATTTTTG | 2265 |
| GAGTGTAGCA TAGCCCAATC AATCAAATCT TCGATAATGC CACTTTTTAC ATATACACGA | 2325 |
| CGACAACCCA CAGTAGTAAC ACTCATGACT AAATTTTCAT CAGTACTTAA TGTCATGTTA | 2385 |
| GGGGCTAACG AAATCAATGC AATGGGCGTT TCTCTATAAA CGATGATATG CGTATTGTTC | 2445 |
| ACCACTGGAT CC | 2457 |

(2) INFORMATION FOR SEQ ID NO:12:

(i) SEQUENCE CHARACTERISTICS:

(A) LENGTH: 337 amino acids
(B) TYPE: amino acid
(D) TOPOLOGY: linear (ii) MOLECULE TYPE: protein (xi) SEQUENCE DESCRIPTION: SEQ ID NO:12:

```
Met Lys Ile Ser Ala Ala Leu Ile Leu Ser Ser Leu Ser Ser Val Ala
 1               5                  10                  15

Phe Ser Ala Pro Ala Pro Ala Asp Ser His His Glu Asp His
             20                  25                  30

His Lys Asp Glu Lys Pro Ala Val Val Thr Val Thr Gln Tyr Ile Asp
             35                  40                  45

Ser Asn Ala Ala Thr Ser Thr Val Glu Ser Ala Ala Thr Thr Thr Thr
     50                  55                  60

Leu Ser Ser Ser Glu Lys Asp Thr Ser Glu Gln Lys Arg Asp Gly Gly
 65                  70                  75                  80

Phe Gln Asp Gly Thr Val Lys Cys Ser Asp Phe Pro Ser Val Asn Gly
                 85                  90                  95

Ile Val Ser Leu Asp Trp Leu Gly Phe Gly Trp Ala Ser Val Met
            100                 105                 110

Asp Met Asp Ala Asn Thr Ser Ser Glu Cys Lys Asp Gly Tyr Tyr Cys
            115                 120                 125

Ser Tyr Ala Cys Glu Pro Gly Met Ser Lys Thr Gln Trp Pro Ser Asp
    130                 135                 140

Gln Pro Ser Asp Gly Lys Ser Val Gly Gly Leu Tyr Cys Lys Asn Gly
145                 150                 155                 160

Tyr Leu Tyr Arg Thr Asn Thr Asp Thr Ser Asp Leu Cys Ser Thr Asp
                165                 170                 175

Glu Thr Ser Ala Lys Ala Ile Asn Lys Lys Ser Asp Ser Ile Ala Leu
            180                 185                 190

Cys Arg Thr Asp Tyr Pro Gly Ser Glu Asn Met Val Ile Pro Thr Val
            195                 200                 205

Val Asp Gly Gly Asp Ser Gln Pro Ile Ser Val Val Asp Glu Asp Thr
    210                 215                 220

Tyr Tyr Gln Trp Gln Gly Lys Lys Thr Ser Ala Gln Tyr Tyr Ile Asn
225                 230                 235                 240

Asn Ala Gly Val Ser Ala Glu Asp Gly Cys Ile Trp Gly Thr Ser Gly
                245                 250                 255

Ser Asp Val Gly Asn Trp Ala Pro Leu Val Leu Gly Ala Gly Ser Thr
            260                 265                 270

Asn Gly Glu Thr Tyr Leu Ser Leu Ile Pro Asn Pro Asn Ser Asn Gln
            275                 280                 285

Ala Ala Asn Phe Asn Val Lys Ile Val Ala Ser Asp Gly Ala Asn Val
            290                 295                 300

Gln Gly Ser Cys Ala Tyr Glu Asp Gly Ser Phe Thr Gly Asp Gly Ser
305                 310                 315                 320

Asp Gly Cys Thr Val Ser Val Leu Ser Gly Ser Ala Glu Phe Val Phe
                325                 330                 335

Tyr
```

(2) INFORMATION FOR SEQ ID NO:13:

(i) SEQUENCE CHARACTERISTICS:
(A) LENGTH: 2150 base pairs
(B) TYPE: nucleic acid
(C) STRANDEDNESS: double -continued (D) TOPOLOGY: linear (ii) MOLECULE TYPE: DNA (genomic)

(ix) FEATURE:
    (A) NAME/KEY: CDS
    (B) LOCATION: 563..1987

(xi) SEQUENCE DESCRIPTION: SEQ ID NO:13:

```
TGTTTAGTGC TACCCAACTA CTTACATTCC TTTAAAAACC ACAATATTTA AGTTAACCTG    60

AGCTTTATTT TTAGTAAGTT ATTTACCACA ATTTTTCTCA TACACCTTTA CAATCCGTAT   120

TGCCATGAAT ACCAAGGCTT GCTCAGCTTC TGCAGCAGTT CAACCCTTTC CAATACCGCC   180

AATGCGTCCT CAAAACGTTA GTTTAGTCGT GCTCAACCGC TATTTTTGGT TTTATCTTCG   240

TTTCTTTCTC CTGAACGACA TTCGTCACGA AAATTGCGGC GGAAAATTTC CTGATGCGGA   300

CACTTTTTCC CGATCCGGAC ATGCCTTTTT TTGGCGTTTC GCGTCAGTCA ATAGAAGTTT   360

CAGATCTACA TTAGGAAGAA CCAGAAAATA GCCATTAATG CTTTCAGCAT AGCACAGCAT   420

AGCAGCTGTG TATATCTTAA ATAAGATGTA GACTGGTTTG CATTTGGAAA GGTTTTGTGT   480

AAGAAAAGCA ATACTTGAGG TAAAACAAGA GAAAAAAAAA CACTTTACTA ACTAATATCC   540

AATCCTTTAT TTTTTTGCAG AA ATG AAA TTC TCA ACT GCC GTT ACT ACG TTG    592
                         Met Lys Phe Ser Thr Ala Val Thr Thr Leu
                          1               5                  10

ATT AGT TCT GGT GCC ATC GTG TCT GCT TTA CCA CAC GTG GAT GTT CAC    640
Ile Ser Ser Gly Ala Ile Val Ser Ala Leu Pro His Val Asp Val His
                15                  20                  25

CAA GAA GAT GCC CAC CAA CAT AAG AGG GCC GTT GCG TAC AAA TAC GTT    688
Gln Glu Asp Ala His Gln His Lys Arg Ala Val Ala Tyr Lys Tyr Val
         30                  35                  40

TAC GAA ACT GTT GTT GTC GAT TCT GAT GGC CAC ACT GTA ACT CCT GCT    736
Tyr Glu Thr Val Val Val Asp Ser Asp Gly His Thr Val Thr Pro Ala
     45                  50                  55

GCT TCA GAA GTC GCT ACT GCT GCT ACC TCT GCT ATC ATT ACA ACA TCT    784
Ala Ser Glu Val Ala Thr Ala Ala Thr Ser Ala Ile Ile Thr Thr Ser
 60                  65                  70

GTG TTG GCT CCA ACC TCC TCC GCA GCC GCT GGG ATA GCC GCT TCC ATT    832
Val Leu Ala Pro Thr Ser Ser Ala Ala Ala Gly Ile Ala Ala Ser Ile
             75                  80                  85                  90

GCT GTT TCA TCT GCT GCC TTA GCC AAG AAT GAG AAA ATC TCT GAT GCC    880
Ala Val Ser Ser Ala Ala Leu Ala Lys Asn Glu Lys Ile Ser Asp Ala
                 95                 100                 105

GCT GCA TCT GCC ACT GCC TCA ACA TCT CAA GGG GCA TCC TCC TCC TCC    928
Ala Ala Ser Ala Thr Ala Ser Thr Ser Gln Gly Ala Ser Ser Ser Ser
             110                 115                 120

TCC TCC TCC TCG GCA ACT TCT ACC CTA GAA AGC AGC TCT GTT TCT TCA    976
Ser Ser Ser Ser Ala Thr Ser Thr Leu Glu Ser Ser Ser Val Ser Ser
         125                 130                 135

TCT AGT GAA GAA GCT GCT CCA ACA TCT ACT GTC GTG TCA ACT TCT TCC   1024
Ser Ser Glu Glu Ala Ala Pro Thr Ser Thr Val Val Ser Thr Ser Ser
 140                 145                 150

GCA ACC CAA TCT AGT GCT TCT TCT GCC ACT AAA TCT AGT ACT TCT TCC   1072
Ala Thr Gln Ser Ser Ala Ser Ser Ala Thr Lys Ser Ser Thr Ser Ser
155                 160                 165                 170

ACT TCA CCA TCT ACT TCT ACT TCT ACT TCC ACT TCT TCT ACT TCC TCT   1120
Thr Ser Pro Ser Thr Ser Thr Ser Thr Ser Thr Ser Ser Thr Ser Ser
                 175                 180                 185

TCC TCT TCC TCC TCC TCC TCC TCT TCT TCT TCT TCT TCT GGC AGT GGT   1168
Ser Ser Ser Ser Ser Ser Ser Ser Ser Ser Ser Ser Ser Gly Ser Gly
             190                 195                 200
```

-continued

```
AGT ATC TAC GGT GAT TTG GCC GAC TTT TCA GGC CCA AGT GAG AAA TTC    1216
Ser Ile Tyr Gly Asp Leu Ala Asp Phe Ser Gly Pro Ser Glu Lys Phe
    205                 210                 215

CAA GAC GGC ACT ATT CCA TGT GAC AAA TTC CCA TCT GGT CAA GGT GTC    1264
Gln Asp Gly Thr Ile Pro Cys Asp Lys Phe Pro Ser Gly Gln Gly Val
220                 225                 230

ATT TCT ATT GAC TGG ATT GGC GAG GGT GGA TGG TCC GGT GTG GAA AAC    1312
Ile Ser Ile Asp Trp Ile Gly Glu Gly Gly Trp Ser Gly Val Glu Asn
235                 240                 245                 250

ACC GAC ACT TCC ACT GGC GGT TCA TGC AAG GAG GGG TCC TAC TGT TCC    1360
Thr Asp Thr Ser Thr Gly Gly Ser Cys Lys Glu Gly Ser Tyr Cys Ser
                255                 260                 265

TAC TCC TGC CAA CCA GGT ATG TCT AAG ACC CAA TGG CCA TCC GAT CAA    1408
Tyr Ser Cys Gln Pro Gly Met Ser Lys Thr Gln Trp Pro Ser Asp Gln
            270                 275                 280

CCA TCT GAC GGT AGA TCT GTC GGG GGT TTG TTG TGT AAA AAT GGT TAT    1456
Pro Ser Asp Gly Arg Ser Val Gly Gly Leu Leu Cys Lys Asn Gly Tyr
        285                 290                 295

TTG TAC CGT TCT AAC ACT GAC GCG GAT TAC TTA TGT GAA TGG GGT GTC    1504
Leu Tyr Arg Ser Asn Thr Asp Ala Asp Tyr Leu Cys Glu Trp Gly Val
    300                 305                 310

GAG GCT GCC TAT GTT GTT TCT AAA CTA AGC AAG GGT GTC GCC ATT TGC    1552
Glu Ala Ala Tyr Val Val Ser Lys Leu Ser Lys Gly Val Ala Ile Cys
315                 320                 325                 330

AGA ACC GAC TAC CCG GGC ACT GAA AAC ATG GTT ATC CCA ACC TAT GTT    1600
Arg Thr Asp Tyr Pro Gly Thr Glu Asn Met Val Ile Pro Thr Tyr Val
                335                 340                 345

GAA GGG GGT AGC TCT TTG CCA TTG ACC GTT GTT GAC CAA GAT ACT TAC    1648
Glu Gly Gly Ser Ser Leu Pro Leu Thr Val Val Asp Gln Asp Thr Tyr
            350                 355                 360

TTT ACT TGG GAA GGC AAA AAG ACA TCT GCT CAA TAC TAC GTT AAT AAC    1696
Phe Thr Trp Glu Gly Lys Lys Thr Ser Ala Gln Tyr Tyr Val Asn Asn
        365                 370                 375

GCC GGC GTC TCA GTT GAA GAT GGG TGT ATC TGG GGT ACT TCT GGA TCT    1744
Ala Gly Val Ser Val Glu Asp Gly Cys Ile Trp Gly Thr Ser Gly Ser
    380                 385                 390

GGT ATT GGT AAC TGG GCA CCA TTA AAC TTT GGT GCT GGC TCC ACT GGT    1792
Gly Ile Gly Asn Trp Ala Pro Leu Asn Phe Gly Ala Gly Ser Thr Gly
395                 400                 405                 410

GGA GTG ACA TAC TTA TCA TTG ATT CCT AAC CCA AAC AAC AGC GAC GCA    1840
Gly Val Thr Tyr Leu Ser Leu Ile Pro Asn Pro Asn Asn Ser Asp Ala
                415                 420                 425

TTG AAC TAC AAC GTC AAG ATA GTT GCT GCT GAT GAT TCA TCC AAT GTC    1888
Leu Asn Tyr Asn Val Lys Ile Val Ala Ala Asp Asp Ser Ser Asn Val
            430                 435                 440

ATC GGT GAA TGT GTT TAC GAA AAT GGT GAG TTC TCT GGC GGT GCT GAC    1936
Ile Gly Glu Cys Val Tyr Glu Asn Gly Glu Phe Ser Gly Gly Ala Asp
        445                 450                 455

GGG TGT ACC GTC TCT GTT ACT TCC GGT AAA GCT CAT TTC GTC TTA TAC    1984
Gly Cys Thr Val Ser Val Thr Ser Gly Lys Ala His Phe Val Leu Tyr
    460                 465                 470

AAT TAAGCTACGT GACTACTACT TTTCCTTTTT TTTTTCTTTT TTCGAACACA         2037
Asn

475

TCTCACCCCC TATACCTCAC ACAATCACTA TGGTCCCCTT TTCTTTTTAC CGATATTTAT  2097

ACTGTCCACC TTTTTCTTTT CGTTAATGGC CTCAATGTTT CTGTACCATT ATC         2150
```

(2) INFORMATION FOR SEQ ID NO:14:

-continued (i) SEQUENCE CHARACTERISTICS:
    (A) LENGTH: 475 amino acids
    (B) TYPE: amino acid
    (D) TOPOLOGY: linear (ii) MOLECULE TYPE: protein (xi) SEQUENCE DESCRIPTION: SEQ ID NO:14:

```
Met Lys Phe Ser Thr Ala Val Thr Thr Leu Ile Ser Ser Gly Ala Ile
 1               5                  10                  15

Val Ser Ala Leu Pro His Val Asp Val His Gln Glu Asp Ala His Gln
                20                  25                  30

His Lys Arg Ala Val Ala Tyr Lys Tyr Val Tyr Glu Thr Val Val Val
            35                  40                  45

Asp Ser Asp Gly His Thr Val Thr Pro Ala Ala Ser Glu Val Ala Thr
        50                  55                  60

Ala Ala Thr Ser Ala Ile Ile Thr Thr Ser Val Leu Ala Pro Thr Ser
65                  70                  75                  80

Ser Ala Ala Ala Gly Ile Ala Ala Ser Ile Ala Val Ser Ser Ala Ala
                85                  90                  95

Leu Ala Lys Asn Glu Lys Ile Ser Asp Ala Ala Ser Ala Thr Ala
                100                 105                 110

Ser Thr Ser Gln Gly Ala Ser Ser Ser Ser Ser Ser Ser Ala Thr
            115                 120                 125

Ser Thr Leu Glu Ser Ser Ser Val Ser Ser Ser Glu Glu Ala Ala
        130                 135                 140

Pro Thr Ser Thr Val Val Ser Thr Ser Ser Ala Thr Gln Ser Ser Ala
145                 150                 155                 160

Ser Ser Ala Thr Lys Ser Ser Thr Ser Ser Thr Ser Pro Ser Thr Ser
                165                 170                 175

Thr Ser Thr Ser Thr Ser Ser Thr Ser Ser Ser Ser Ser Ser Ser Ser
            180                 185                 190

Ser Ser Ser Ser Ser Ser Ser Gly Ser Gly Ser Ile Tyr Gly Asp Leu
        195                 200                 205

Ala Asp Phe Ser Gly Pro Ser Glu Lys Phe Gln Asp Gly Thr Ile Pro
    210                 215                 220

Cys Asp Lys Phe Pro Ser Gly Gln Gly Val Ile Ser Ile Asp Trp Ile
225                 230                 235                 240

Gly Glu Gly Gly Trp Ser Gly Val Glu Asn Thr Asp Thr Ser Thr Gly
                245                 250                 255

Gly Ser Cys Lys Glu Gly Ser Tyr Cys Ser Tyr Ser Cys Gln Pro Gly
            260                 265                 270

Met Ser Lys Thr Gln Trp Pro Ser Asp Gln Pro Ser Asp Gly Arg Ser
        275                 280                 285

Val Gly Gly Leu Leu Cys Lys Asn Gly Tyr Leu Tyr Arg Ser Asn Thr
    290                 295                 300

Asp Ala Asp Tyr Leu Cys Glu Trp Gly Val Glu Ala Ala Tyr Val Val
305                 310                 315                 320

Ser Lys Leu Ser Lys Gly Val Ala Ile Cys Arg Thr Asp Tyr Pro Gly
                325                 330                 335

Thr Glu Asn Met Val Ile Pro Thr Tyr Val Glu Gly Gly Ser Ser Leu
            340                 345                 350

Pro Leu Thr Val Val Asp Gln Asp Thr Tyr Phe Thr Trp Glu Gly Lys
        355                 360                 365

Lys Thr Ser Ala Gln Tyr Tyr Val Asn Asn Ala Gly Val Ser Val Glu
    370                 375                 380
```

```
Asp Gly Cys Ile Trp Gly Thr Ser Gly Ser Gly Ile Gly Asn Trp Ala
385                 390                 395                 400

Pro Leu Asn Phe Gly Ala Gly Ser Thr Gly Gly Val Thr Tyr Leu Ser
            405                 410                 415

Leu Ile Pro Asn Pro Asn Ser Asp Ala Leu Asn Tyr Asn Val Lys
                420                 425                 430

Ile Val Ala Ala Asp Asp Ser Ser Asn Val Ile Gly Glu Cys Val Tyr
            435                 440                 445

Glu Asn Gly Glu Phe Ser Gly Gly Ala Asp Gly Cys Thr Val Ser Val
            450                 455                 460

Thr Ser Gly Lys Ala His Phe Val Leu Tyr Asn
465                 470                 475
```

(2) INFORMATION FOR SEQ ID NO:15:

(i) SEQUENCE CHARACTERISTICS:
        (A) LENGTH: 145 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:15:

```
Thr Asp Tyr Pro Gly Xaa Glu Asn Met Val Xaa Pro Thr Xaa Val Xaa
1               5                   10                  15

Xaa Gly Xaa Ser Xaa Pro Xaa Xaa Val Xaa Xaa Xaa Asp Xaa Tyr Xaa
            20                  25                  30

Xaa Trp Xaa Gly Lys Lys Thr Ser Ala Gln Tyr Tyr Xaa Asn Asn Xaa
            35                  40                  45

Gly Val Ser Xaa Glu Asp Gly Cys Ile Trp Gly Thr Xaa Gly Ser Xaa
            50                  55                  60

Xaa Gly Asn Trp Ala Pro Xaa Xaa Xaa Gly Ala Xaa Xaa Thr Xaa Gly
65                  70                  75                  80

Xaa Thr Tyr Leu Ser Xaa Ile Pro Asn Pro Asn Xaa Xaa Xaa Ala Xaa
            85                  90                  95

Asn Xaa Asn Xaa Lys Ile Val Ala Xaa Asp Xaa Xaa Xaa Xaa Val Xaa
            100                 105                 110

Gly Xaa Cys Xaa Tyr Glu Xaa Gly Xaa Xaa Xaa Gly Xaa Gly Xaa Asp
            115                 120                 125

Gly Cys Thr Val Ser Val Xaa Ser Gly Xaa Ala Xaa Phe Val Xaa Tyr
            130                 135                 140

Xaa
145
```

(2) INFORMATION FOR SEQ ID NO:16:

(i) SEQUENCE CHARACTERISTICS:
        (A) LENGTH: 60 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:16:

```
Ser Leu Ile Pro Asn Pro Asn Asn Gly Asn Ala Leu Asn Phe Asn Val
1               5                   10                  15

Lys Ile Val Ala Ala Asp Asp Ser Ser Thr Val Asn Gly Glu Cys Ile
            20                  25                  30
```

```
Tyr Glu Asn Gly Ser Phe Ser Ser Gly Gly Ser Asp Gly Cys Thr Val
         35                  40                  45

Ser Val Thr Ala Gly Lys Ala Lys Phe Val Leu Tyr
 50              55                  60
```